(12) United States Patent
D'Elia et al.

(10) Patent No.: US 7,030,233 B2
(45) Date of Patent: Apr. 18, 2006

(54) KETOGULONIGENIUM ENDOGENEOUS PLASMIDS

(75) Inventors: John D'Elia, Champaign, IL (US); Steven F Stoddard, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 424 days.

(21) Appl. No.: 10/261,481

(22) Filed: Oct. 2, 2002

(65) Prior Publication Data

US 2003/0077830 A1    Apr. 24, 2003

Related U.S. Application Data

(62) Division of application No. 09/826,191, filed on Apr. 5, 2001, now abandoned.

(60) Provisional application No. 60/194,627, filed on Apr. 5, 2000.

(51) Int. Cl.
    C07H 21/04    (2006.01)
    C12N 15/70    (2006.01)
    C12N 15/74    (2006.01)

(52) U.S. Cl. .................. 536/23.1; 435/320.1; 435/243; 435/252.3; 435/252.33; 435/252.8

(58) Field of Classification Search ............. 435/320.1, 435/243, 252.1, 252.3; 536/23.1, 24.1
    See application file for complete search history.

(56) References Cited

U.S. PATENT DOCUMENTS

| | | |
|---|---|---|
| 2,421,611 A | 6/1947 | Gray |
| 3,043,749 A | 7/1962 | Huang |
| 3,234,105 A | 2/1966 | Motizuki et al. |
| 3,907,639 A | 9/1975 | Makover et al. |
| 3,912,592 A | 10/1975 | Makover et al. |
| 4,876,195 A | 10/1989 | Shirafuji et al. |
| 4,877,735 A | 10/1989 | Nogami et al. |
| 4,892,823 A | 1/1990 | Imai et al. |
| 4,933,289 A | 6/1990 | Imai et al. |
| 4,935,359 A | 6/1990 | Yin et al. |
| 4,945,048 A | 7/1990 | Uchihori et al. |
| 4,960,695 A | 10/1990 | Hoshino et al. |
| 4,994,382 A | 2/1991 | Ameyama et al. |
| 5,082,785 A | 1/1992 | Manning et al. |
| 5,312,741 A | 5/1994 | Hoshino et al. |
| 5,344,768 A | 9/1994 | Urakami |
| 5,399,496 A | 3/1995 | Fujiwara et al. |
| 5,437,989 A | 8/1995 | Asakura et al. |
| 5,474,924 A | 12/1995 | Nogami et al. |
| 5,541,108 A | 7/1996 | Fujiwara et al. |
| 5,580,782 A | 12/1996 | Beppu et al. |
| 5,834,231 A | 11/1998 | Stoddard et al. |
| 5,989,891 A | 11/1999 | Liaw et al. |
| 6,127,156 A | 10/2000 | Hoshino et al. |
| 6,127,174 A | 10/2000 | Tonouchi et al. |
| 6,316,231 B1 | 11/2001 | Stoddard et al. |
| 6,319,699 B1 | 11/2001 | Stoddard et al. |
| 6,503,748 B1 | 1/2003 | Schmidt et al. |
| 6,506,583 B1 | 1/2003 | Stoddard |
| 6,511,820 B1 | 1/2003 | Stoddard |
| 6,541,239 B1 | 4/2003 | Stoddard et al. |
| 6,562,584 B1 | 5/2003 | Stoddard et al. |
| 2002/0039761 A1 | 4/2002 | D'Elia |

FOREIGN PATENT DOCUMENTS

| | | |
|---|---|---|
| CN | 1081470 A | 2/1994 |
| EP | 0 206 471 B1 | 12/1986 |
| EP | 0 213 591 B1 | 3/1987 |
| EP | 0 221 707 B1 | 5/1987 |
| EP | 0 276 832 A2 | 8/1988 |
| EP | 0 278 447 B1 | 8/1988 |
| EP | 0 276 832 A3 | 7/1989 |
| EP | 0 381 027 A3 | 5/1990 |
| EP | 0 381 027 A1 | 8/1990 |
| EP | 0 448 969 A2 | 10/1991 |
| EP | 0 448 969 A3 | 1/1992 |
| EP | 0 518 136 A2 | 12/1992 |
| EP | 0 518 136 A3 | 3/1994 |
| EP | 0 832 974 A2 | 4/1998 |
| EP | 0 832 974 A3 | 4/1998 |
| EP | 1 076 094 A2 | 2/2001 |
| JP | 41-159 | 1/1966 |
| JP | 41-160 | 1/1966 |
| JP | 41-5907 | 3/1966 |
| JP | 59-113896 | 6/1984 |
| JP | 3-294281 | 12/1991 |
| JP | 7-67673 | 3/1995 |
| JP | 7-250671 | 10/1995 |
| JP | 8-245702 | 9/1996 |
| SU | 526660 | 10/1976 |
| WO | WO 98/17819 A1 | 4/1998 |
| WO | WO 98/17819 A3 | 4/1998 |

(Continued)

OTHER PUBLICATIONS

Everett et al. Pendred syndrome is caused by mutations in a putative sulphate transporter gene (PDS). Nature Genetics 17: 411-422, 1997.*

Scott et al. The pendred syndrome gene encodes a chloride-iodide trasnport protein. Nature Genetics 21: 440-443, 1999.*

(Continued)

Primary Examiner—James Ketter
Assistant Examiner—David A. Lambertson
(74) Attorney, Agent, or Firm—Kirkpatrick & Lockhart Nicholson Graham LLP

(57) ABSTRACT

The present invention relates, in general, to a genus of bacteria known as *Ketogulonigenium*. The present invention further relates to transformed *Ketogulonigenium*, and methods of transforming *Ketogulonigenium*. The present invention also relates to nucleic acid molecules, and vectors.

20 Claims, 34 Drawing Sheets

FOREIGN PATENT DOCUMENTS

| | | |
|---|---|---|
| WO | WO 98/33885 A1 | 8/1998 |
| WO | WO 98/33885 A3 | 8/1998 |
| WO | WO 00/15827 A1 | 3/2000 |
| WO | WO 00/15827 A3 | 7/2000 |

OTHER PUBLICATIONS

Altschul, S.F., et al., "Gapped BLAST and PSI-BLAST: a new generation of protein database search programs," *Nucl. Acids Res.* 25:3389-3402, Oxford University Press (1997).

Delic, V., et al., "Microbial Reactions for the Synthesis of Vitamin C (L-Ascorbic Acid)," in *Biotechnology of Vitamins, Pigments and Growth Factors*, Vandamme, E.J., ed., Elsevier Applied Science (London & New York) pp. 299-336 (1989).

Helinski, D.R., et al., "Replication Control and Other Stable Maintenance Mechanisms of Plasmids," *Escherichia coli and Salmonella: Cellular and Molecular Biology*, Ch. 122, vol. 2, 2nd edition, Neidhardt, F.C., ed., pp. 2295-2324, ASM Press (1996).

Lonsdale, D.M., et al., "pFC1 to pFC7: A Novel Family of Combinatorial Cloning Vectors," *Plant Biol. Reporter* 13: 343-345, Transaction Periodicals Consortium (1995).

Pearson, W.L., and Lipman, D.J., "Improved tools for biological sequence comparison," *Proc. Natl. Acad. Sci. USA* 85:2444-2448, National Academy of Sciences of the USA (1988).

Sugisawa, H., et al., "Microbial Production of 2-Keto-L-Gulonic Acid from L-Sorbose and D-Sorbitol by *Gluconobacter melanogenus,*" *Agric. Biol. Chem.* 54:1201-1209, Japan Society for Bioscience, Biotechnology, and Agrochemistry (1990).

Follettie, M. T., "DNA Technology for *Corynebacterium glutamicum*: Isolation and Characterization of Amino Acid Biosynthetic Genes," Ph. D. Thesis, Massachusetts Institute of Technology (1989).

Kieslich, K., "Biotransformations," *Biotechnology, A Comprehensive Treatise in 8 Volumes*, Deerfield Beach, Florida 6A:436-437, Verlag Chemie, (1984).

Martin, C.K.A., and Perlman, D., "Conversion of L-Sorbose to 2-Keo-L-gulonic Acid by Mixtures of Immobilized Cells of Gluconobacter melanogenus IFO 3293 and Pseudomonas Species," *Eur. J. Appl. Microbiol*, 3:91-95, Springer-Verlag (1976).

"The Genetic Improvement of Product Formation," in *Molecular Biology and Biotechnology*, Walker, J.M., and Gingold, E.B., eds., Royal Society of Chemistry, London, Great Britain, pp. 15-20, The Royal Society of Chemistry (1988).

Tsukada, Y., and Perlman, D., "The Fermentation of L-Sorbose by Gluconobacter melanogenus. I. General Characteristics of the Fermentation," *Biotechnology and Bioengineering XIV*: 799-810, John Wiley & Sons, Inc. (1972).

Urbance, J.M., et al., "Taxonomic characterization of *Ketogulonigenium vulgare* gen. nov., sp. nov. and *Ketogulonigenium robustum* sp. nov., which oxidize L-sorbose to 2-keto-L-gulonic acid," *Int. J. Systematic Evol. Microbial.* 51:1059-1070, International Union of Microbiological Societies (May 2001).

Vandamme, E.J., "Production of Vitamins, Coenzymes and Related Biochemicals by Biotechnological Processes," *J. Chem. Tech. Biotechnol.* 53:313-327, Elsevier Applied Science (1992).

Yin, G.-L., et al., "Studies on the Production of Vitamin C Precursor 2-Keto-L-Gluconic Acid from L-Sorbose by Fermentation. I. Isolation, Screening and Identification of 2-Keto-L-Gluconic Acid Producing Bacteria," *Acta Microbiologica Sinica* 20 (*3*): 246-251, Welshengwu Xuebao (1980).

Yin, G.-L., et al., "Studies on Production of Vitamin C Precursor 2-Keto-L-Gluconic Acid From L-Sorbose By Fermentation," *Acta Microbiologica Sinica 21* (*2*): 185-191, Weishengwu Xuebao (1981).

\* cited by examiner

SEQ ID NO:1

```
   1  GCCATTTCTG CGCTGCACTT CGCTAAGGGT TCAAGGGAAA CGCAGGGTTC
  51  CCTTGCCCAC ACAAACGCGC AGCGTTTGTA TAAGTGGGCA CTTCGTGTTT
 101  GACACGCTAT CCACTACGCG GCACAAATTC AACTCTTGTA ACGAGGAAGG
 151  GCGGTAGAAT GGCGCGCACC ATCGACCAGC AGATCGCAGA TGCGCAAGCG
 201  AAGCTGGCGC GGCTCAAAAC CCGTCAGAAA GCCAGCGACA CCCGCCGAAA
 251  GATCATCGTC GGCGCCATCG TCACCACCGA GGCCCTGAAA GACCCCAAGA
 301  TTTCCAAATG GCTGGCATCT ACCCTGCGCA AGAACGCAAC CCGGGACGTG
 351  GACCAGAAGG AAATCGCCGG GCTGCTGGCC GACCTCGATG CCAGGGCGCA
 401  AAGCGCCGGG GCGGGTGAGG CATGAGCGGC AGCACCGATC CGTTTCTGGT
 451  TCTGGTCGAT GATATTGGCG CGCTGCGCCG CCAGATCGAG AACCTGCAAC
 501  GCACCAGCCT CGACAGGGAC GAGGCCGAAC ATCTCAACGC GACCATCGCC
 551  CAGAGCCTCG ACAACATGGC GCAAACCGGA AAACGGCTGG AACAGCGCCT
 601  TGAGGGCCAG TTGCAGCTCG CCACCGCCAA AACCCACAGG GACGCCATAG
 651  AAGCCGCTCA GGGGGCCGCC AGAGCGGCTA TCAGGGAATC CCATGCCGAG
 701  ATCCTCCAAA CGGCCAGGAG CCTCTCACAG GCCGCAGGAG AGGCCCGCAG
 751  AGAGGCGTGG CGCTGGTTCG GCGGGTTCTG GGTCTGGCTG GCCTCGATCG
 801  GGGCCGCAGG GGCGCTTGTC GGCGCGCTGG CCGTGTTCTG GCTCCAGGGC
 851  CGCGCCGATG CCAAAGCCTT CGGACAGTAT CCCAGCATCT ACTGCACCAC
 901  CGCAGGCGGG GCATTCGCCG ATCAGCGCGA CGGAAGCCGA TACTGCATCT
 951  TCATGATTTC ACCGCCGACA CAGCCAGACG GGAATGACG GCTTACGCGC
1001  CGGGCTGGAT CGAGACTTTC AGCCCGAGCG CCTTAGCGAC CTTCATCACC
1051  GTGGACAGCG TAGGGTTCCC ATCCCCGGAT AGCGCCTTGT TCAGCCCCAC
1101  CCGGCTCATG CCAACCTCAC GGGCCAGCGC GGTCATGTTC CGTGCGCGGG
1151  CAACCACTCC AAGGGCGCGG GCAACATAGG CGGGATCGTC GCCGCCATCT
1201  TCCATGACCG CTTCGAGATA GGCCGCAATA TCTTCCTCGG TCTTGAGGTA
1251  GTCGGCGGAA TCGTAGCGGG CGAATTTTTC TTCCGGCATC GCTTAGCCCT
1301  TCCACTCTGC GGCCAGCACC TTGGCCTGTT TGATGTCTTT GCTCTGCGTG
1351  GACTTGTCGC CGCCACAAAG CAGGATCACG AGAACCGGCC CGCGCTGGAT
```

FIGURE 1A

```
1401  GAAATACACC CGGTAGCCCG GCCCGTAGTT GATCCGCAGT TCCGAAACAC
1451  CCTCTCCGAC CGGCTCCACA TCGCCGGGGT TCCCCGCCGC AAGGCGGTCC
1501  AGTCTGGCAG TGATGCGCGC AACCGCCCTG CGATCCCGCA AACCGGAAAG
1551  CCAGGTATCG AAGGTTCCGC TTCGGATTAA CTCGATCATT CGACAACTAT
1601  AGTTATCATG TGGGTGTCTG ACAACCAGAG TTATCACTTC CTTGTTCTAA
1651  GCAAATCCGA GGCCAGCCAC GGGCGTAGCC GGAGCATCAT CCCTCCCCCG
1701  CACCCCCACC CGTCACGCGC ACACATGCGC GGAATCGTCC ACTCGGCCCA
1751  CAAGGGGCCT TGCATCCGAT GGCAAGCAAA AACTACCCAG TCCGTCCGTA
1801  GGCGGGGGGT CGCCAGCCCT GTGGGTGGGC GCTTCCCCCC GGCCCGCAAG
1851  CGGGCCCGGA ATGGGCATTT TTTGCCTGCC CTAAGATCAT AAGAAGGGCA
1901  AAAAAAACAT CGTTTCAAAA CAGCGTGTTA CCACCCCCCT ATAGGACACC
1951  AGAGTCCGGG GTAGAGGACT CTGGTGTCCT CTTAGGCCAT TTATGTCCAA
2001  GAATGTGACA GCCAGCCGAG CGGAGGTAGA GGACTCTGGT GTCCTATGCT
2051  TAGGCCATTT ATGTCCAAAA ACTTGACAAG GGCCACATTC CTGCCAAATC
2101  TGTCCAGAAT TTGGAAAAAT TCGCCGGATA GTAGACAGTG GCAAAGCCTC
2151  CCCCCATTCC CGCAAAGCGC CCGCTCGGCA CTTGGGTTCA AACTGACCGG
2201  GAAGCCCACG AGGCGTGGGC GATACTGGCA AAAAAGCCTG CTGCCAGCGC
2251  TGTGATGCAC ATTCTGTGCG CCAACCTCGG TGAGCATAAT GCCGTGGTCA
2301  TCAGCCAGGA CACCATCGCC AAGCTGTGCG GCCTTTCCAC ACGGTCCGTC
2351  AGGCGCGCCA TCGTCGATCT GGCCGAAGGC CGATGGATCG AGGTTCGCCA
2401  ACTTGGCGCG ACCAGCCAGA CCAATGCCTA TGTCGTCAAC GACCGGGTGG
2451  CATGGCAGGG ATCACGGGAC GGACTGCGCT ACAGCCTGTT TAGTGCGGCT
2501  ATAGTCGTGT CCGAGGAGGA GCAACCCGAC CGCGCTGAAC TCGACCAGCA
2551  AGCCCCCCTG CGACACCTGC CACGCATCAG CGAGGGGCAG ATACCCACCG
2601  GCCCCGGCCT GCCGCCACCT TCGCAACCGT TTCTAAAAGA CATGGAGCCA
2651  GACTTGCCCA CCATTGACCG GGCAACATCA CCCAACTTTG ACCAGCAGGA
2701  ACAGGGGTGA AAAAGGTGGA CAAACTTTCC ATACGCGAGG CGGTAAAACA
2751  CTTCGATGTT TCCCGGCCAA CCCTGCAAAA AGCCCTTAAA TCTGGCAAGA
2801  TTTCAGGTGT TCAGGATGGA CAAGGAACGT GGACAATAGA CCCCTCAGAG
2851  ATGGCAAGAG TTTACCAGCC AAGGCAAGAT GAGGTGGTAA AGGATGGTGG
```

FIGURE 1B

```
2901  CCAAGAACAT GAAAATTTGT CCGCCAAGAA CACCCCTTTA CATGGTCAAG
2951  TTGAGGTTCT GAAAGAGCGG CTTGCAGATG CTGAAAAACG GGTGGCGATA
3001  GCCGAGGCAC TGGCCGAAGA ACGTGGAAAA CACATCGAGG ATCTACGCCG
3051  GATGCTGCCT GCACCGGAAG CCGGTCAGCC CCGCCGCCGC TGGTGGCCAT
3101  GGTAAGGTCA GCTATGCGGG ACCAAGCCGC AGCTCGCAAG TGCGGCAACA
3151  GAATCAGACC CGCTTCGGAC AGAGAGCTCA AGCTGGTGGA AAACCGCCTG
3201  TGAAGCTGCT GGGTGGCAGC CGCTTTACTC AGCGAAGCAG CCATTCGGGC
3251  GGATCGCAGC GAGATTGCCC CATCCAGTCC TAAGGGCCGT GTAAACAGCA
3301  CTTAGTGCAG CAGCATCGCA GGCGCGGAAA TCTGCCTGCC CTTCCTCGCC
3351  ACCTCTGAGG CGTCAGCGAT CTGCCCCAAA CCTGCCTGCC ACTTTGGCGC
3401  AGCATGTTGC TTGAGAACAC GGAGCTGCCG ATCTCTGCGC TAAGCAGAAT
3451  TTCCTGATAA TACGCACAGA TGCAAATAAT ATTGCGGCAT CAATGCGTTT
3501  CCGTTTACCC CTAGGCAGTT GCCTCATCAT GCTGTCGTTC GCTGTCCAAG
3551  CCGCAACGAC CTGCGACCGA ACCTTCACTG CATCTTACTT TCGGCCCCTG
3601  CGTTCGCCCG TGACCGCAGC GCGGCCCAAA GCGCGACCGC CGCCAAGGCG
3651  GGTAGGAACA GCCCCATTGC CATCGGGAAC GGGCTGTCGG TCCCGGCCAA
3701  GGCCACGCAG GTCGAAATCG TGAAGGCCAT CCCGAACTGC ACCGCACCCA
3751  AGAGTGCCGA TCCAGTTCCG GCGGCCTCGG TCGCGGCGGC CATGGCAAGC
3801  GAGGTCGCAT TGGCCGAAAG CAGCCCGACC ATGCCGATCG CGATCCAGAG
3851  CGGAATGATA AACATCCATA CCGAACCCGT GGCAGAGGCC AGGACGGCTG
3901  CCAGCGCCGC AAGACCATAG AACGGCAGTC CCCGGTTCAG CATGTCCCGG
3951  GGCGTAAAGC GGTCCAGGAG GCGGCTGTTG ATCTGCGCGA AGACAAACAG
4001  CGCGGCTGCG ATGAGCGCAA ATATCAACCC GTAGTTGAGT GCGCTCATAC
4051  CGAAGAAGCC CTGGAACACC CCGGACGATC CGGTGATGAA GGCGAACATC
4101  CCGCCCTGGA CCAACCCTGC CACCAGCACG GGGCAAGGT AGGCGGGCTG
4151  TCTGACAAGC CGCAGGCCGT TCCTTGTCGC GCTTCGGAAG GCTGCGCGA
4201  CACGGCGCTC TGGCGACAGC GTCTCGGGCA CCACCAGTTT CGACAGGATG
4251  AGGGCAGGCA GACCGACCAG CACCATTGTC ACGAAGATCG ACCGCCAGCC
4301  GAAGGCCTCG AGCAGCAGGC TGCCAAGTGT CGGCGCGATG ACCGGACCTA
4351  TGGTCATCAG CATCACCAGC AAGGTCATCA CCTTGGCCGC CTTTTGCCCC
```

FIGURE 1C

```
4401  GAGTAGAGAT CGGCGACGAT GGCCCTGCTG ACGACCATCC CCACGCAGGC
4451  CCCGATCGCC TGCAAAAAGC GCAGCGCGTT GAAGACAACG ATATTGTCGA
4501  CCAGCGGCAG CGCAATTGAT GTGACGGTGA AGATGAAGAC GCCGATCAGA
4551  AGCGGCCGCT TGCGCCCGTA TCCATCGGTC AGCGGCCCGA CGATCAGCTG
4601  CCCGAGGCAA AGGCCCAGAA AGAACAGCGA CAGTGAAAGC TCGGTCGCCG
4651  CATGGCTGGT ATTCAGATCC TCGGCGAGAA TGCCGATGGC CGAGAGATAC
4701  ATGTCGGTCG CCAGTGGCGG AAAGATCGAC AAAAGGGCGA GCACGGCGAT
4751  CAAGGCACCG GCTCGGGCAG GGATGAGGGG GCGGTCCAGC ATGATATCCT
4801  CTTGGCGGGA TGGTGCGATT CCATTTGTAG ATCGCAGTCT ACTAATGTAA
4851  AATTATACTC AAGTCTATAA TTCAAGTCGC TTGGCCGGAA TCGCAGGAGA
4901  AGACAGGAAT GCAGGAGGTA CGGAGCGGAC CGGGACGGCC AAAAGACCCC
4951  GTGGTTGCCG AAGCGATCCG CAAGGCGGCC CTGCGGCTGG TGCGCGAAAG
5001  GGGATACCGG AACGTAAGCA TCGGCGCGAT CGCGCAAGCC GCTGGAGTGG
5051  CGCGGCAAAC GCTTTACAAT CGCTGGCACG CGAAGGCCGA CCTCATCCTT
5101  GATGCCGTTT TCGAAGAGAC CGGGCGGCGC GCCGACGATC AATTACCGCT
5151  GGAAACAGGG GACGCGTCCC GTGATCGGCT GGAACGGCTT CTTATAGGTG
5201  TGTTCAATCA CCTCCGGGCG GATGGCGATA CACTGCGCGC ATTGATCGCC
5251  GCCGCGCAGG AGGACAGCGA GTTTCGTGAG GCCTTCCGGG AACGGTTCGT
5301  CGCACCGCGG GAAACCATCG TCACCGACAT TCTGGCCGAA GCCCTGCGCC
5351  GTGGCGAGCT TTCCCGGGAA GCCGACCCGG ATACCTTGTC GACCATGATC
5401  CACGGCGCAT TCTGGTATCG CCTCCTGAAC GGACGCGAGC TCGATCATGA
5451  ACTCGCCCGA TCAATAGCGC GGAGCGTGTT TCCCTGAGCC AAGACGAAAC
5501  GGAAACGGAC CCAAATCATC GGAATGTATA AAGTCGCGCA TCGTTACCAT
5551  CCTGAGGGGG TGATCGCTGC GGAGCGAGAC GAATGGCAGC TACCGGGAAT
5601  GCGGCCACGC CGCATTGGTC GAGGTCGGCC AGGGCAAAGG GCTGGCCTTC
5651  ACCTATACAA GCGACAGGCC TGCCATGCGG CGCCCTGCCC AAGTGTCAGC
5701  GATGGGCTCA AACCGTCGAT AGGCCAGCCC CGGCCCGCTC GTTCCATCGC
5751  GGGCTGTAGG GTCGGGGCTG GCCGGATCAG TGAGTAAGCC CGCCATCCCG
5801  GTCGTGGTCA CGGGCTTCTC GCTCCCGCAA CCGTTCCTGC TGCCGCTCTT
5851  GCTCCTTCAG GCGTTCGGCC TCCTGCACCC GCTGGCGTTC CTCGGCCTCC
```

FIGURE 1D

```
5901  CGGCTTTCCT GCAACCGCGC TGCCGCCTCG GCCAGCGTGC CCCGGTCGAT

5951  CCCCTGCGCC GCCTCCCGTA GCCGCTCGGC CAGGCTGCGG GAGGATTCCG

6001  GTTCCGGGGT TTGTCCAGGT GCAGCTATGG CATCGGACGC GGTGCGGCTC

6051  TGGCGGGCCT CCCATGCCTC GCGCAACCGC GCGGCCAGGT CCTGCCTCCC

6101  CTCCCGGCCA TCCCGATCCG CAGCGCCGGC ATAAGCCAGA CCCTGCGCCG

6151  CCCCCTCTTG CGTCAACGGC CCGAGGCGAT CCACAGCTCG CCCGATCCAG

6201  TCGCGCACCT GACCGGCCAG AACCTCCGCC ACACGCGCAA CCTCGGCCGC

6251  CTGCGCCTTG ACCTCGCGCC ACACCCGGAC GGCCCCGACC TCGATACCGC

6301  GTTCCTTCAT CTGCCACGCC CCGGCAGACA GTTGCGGCAA CGGATCCCGG

6351  TCCAGTTCCA CCGCCCGCAC CGTTTGACGC AGCGCCTCGG CCTCGTCGCC

6401  GCGATCATGC GCCGCGCTGG CCCGCTCCTG CGCCTCGATC CGCTGCGCCT

6451  CTAGCGTCCG GTGGTCGATC CGTTCCTCAT GGCCGCATCG CTCAAGGGCG

6501  CGGTTGCTGT CCCGCGCCCA TGCCTCACGC CATCCTTCCA GCATCTCGAC

6551  CGCGTTCCAG TCCCGGTTCT TCGCCCCGAA CCCCTCGGGG CCGATTTCGC

6601  GGGTGGTCAG CAGGATATGG GCATGGTGGT TGCGATCATC GCCGGTCCGT

6651  CCCGGCGCAT GAAGGGCAAT GTCGGCCACC ATGCCACGGG CCACGAACTC

6701  GCGCTGGCAG AATTCGCGCA CCAGCTCCAC GCGCTGTCCG TGGTCCAGCT

6751  CGGCGGGCAG AGCCACCCGG ATTTCGCGGG CGACCTGCGA ATTCTTCCGG

6801  GTCTCTGCCG CCTCGACCGC GTTCCACAGC GCCTCCGGT CCTGCACCCA

6851  TGCGGGGGCG TTGGCAGGGG CGAGGGTTTC GACGTGATCG ACACCGCCAC

6901  GCGCACGGTA ATCGAAGGTC AGCCCGGTGC GGTGATCCTC GATCCGTTCG

6951  CCCACGCGGT AGGCCGCAGC CGCCGTGGCG CTACGACCGG AAGAGCGAGA

7001  TATCATCGTG GCCCGAAGGT GATAGATCG
```

FIGURE 1E

SEQ ID NO:2

```
   1 GCGTCTGTGC GCATACTATC CTCCGTGTTC ATCAGGCTCA CGCCTGATCT
  51 GATTAGGGCT CTTGTCTCTG CTTGTATCGT CGCCAAACTA TACTTTAAGC
 101 AGCGTCTAGA GCCTGATGAA CGATCTAAGA AGCCCGCCCC CTGAAAGGCG
 151 GGCTTTTTTG ATCTGTGCCA GATGTTGTTA CATCGGCGCT CAAAAATCAA
 201 GTTTTTTCTT GACTTTCAAT AATTTGCATT ATGCACATTA TTATCGTTTG
 251 ATAATAAGAG CCAGAACAGC ACAGAATAGT TGTGCGATAG CTATGAATAA
 301 TAGCAGATCC ATCCCTGTTT CCTTTCTTAC TAAATACAAT GCGAAACTGC
 351 TCGCATCTGT TTTATTTAGT TGAATCGGAA ACTCCAAATC GGCCGGATTC
 401 AAAAAAAATA TAGACTATCT TTAAAGTAGC AACGCCGCCG CTCGCGCGAC
 451 GGCATTGCGG GAAATGCGAT AGCAACAAAA CCACTTATTG TCGTATATCC
 501 CCACTTTCAA GCGAAGCGCC CCGCGAAGCG ATCAAAAAAG AAAGAAAGAA
 551 GGGGGCGCTG CCCCCGTCAT GCGCAAGCGC ATGACTCCCC CGCCCCTCAC
 601 TCACCAAAGC AGCAGCTACG AAGCAGGACG GGATCGGCGT TTGTGCATCA
 651 CGTGCTCGCA TCACCAACAC AAATAGACGT ATCCCCATGA ATGGGGCCCC
 701 ACGTCGATTT GTGTTGGCGC TACTGCGCGC GCAATGCCCT GCAGCCTCAC
 751 CCGACCGGCT CCGAAGCAGC AGCTTTTAAG ACAGTGAGTG ACACAAGAAA
 801 ACATGCGCAA GCGCATGTGT GCATCGCGTG CGCGCGATGC ACGGGAAGGT
 851 TGCCTTCGTT GTATATAATA ATATAGCCTG CACGCTGTGC GCACAGCGTG
 901 CATGAGAGGC AAAAACATGT CAAAAATGTT GACTACTGCA CAAGTTGCAC
 951 AGCGCTTTGG ACTGTCACGA TCGACAGTTA GCAGAGCGCT TAAAAACGGC
1001 GACTTGCGTG GCATCCGCGA CAATAGAGGC GTGTGGAAAA TTGCCGAAGA
1051 TGATGCGCAT AAATGGCGCA GCGACGCCGT GCATGAACAG CGTGCGCACA
1101 GCGTGCATGA CAGTGCATTA CGCACACGTG CTGAAGTTGC GGAAGCTCGT
1151 GCAACAGCGC TAGAAATGCA CGTGTCTGAC TTGCAAAGCG AGCGTGACGA
1201 CTTGCGAAAG CAGCGCGACG AGCTGCAAGC GAAGTTAGAC GGTCGGCCCG
1251 TCGAAACTGT CAGTATCAGC CAGCTTTTCG GCGCCTTTT TCGGCGCTGA
1301 CATGGCGCGT AGAAGCGCGA CAGTCTCAGC TTTCGTTCGC TTCATCTGCG
1351 GCATGATCTT CACAGCATCA GTGCGTGCTG CGCGTGTCTC TTCGACCTCT
```

FIGURE 2A

```
1401  TTTCTAGAGC  CGAGCCGCAA  TGCAATCTGA  ATAGATCTGC  GTATTCGCGG

1451  CAAGCTTTTA  CGCACTTCTG  AAATCGCTTC  ATCGAGCGAC  TTCAAGCGCT

1501  CTACAAGAAT  GCCGCGCAAG  CCAGAAACTC  GCTTGCGCTC  AGCCCTGACG

1551  GCTTCGACAG  CGACAGACTT  TGACGCTCA   AAATCGACTT  GTGCAGCATC

1601  GAGCTTTGCA  CGCTCTGCAT  CGAGCTGCTC  GCGTTGTGTT  TTAAGCTCTG

1651  TGCGCTCTGT  CTCGACAGCT  TTAAAAGCCT  CAGTTTCTAA  GCGATCCGGC

1701  GCGCCGTCCG  ACTTCTCACG  CTTAGGCTCT  AGCTTGATGT  TATTCCGACG

1751  CTCGAAAAAC  GCAGCAAACT  CGCTTTGCAG  CGCAATACCG  ACCGCGCGCG

1801  GCGCGCTATA  GTTTGGCGCT  GCCCCAGAAT  GCCGCCGCTG  GATCTCTTCG

1851  CGATGTTTAT  CGGCCAGCTC  GCGACCAAAT  TTTGTGGCGC  TCGACCACAT

1901  TTCGCCAGGC  TGATCCGGCG  GCGTTCTTTT  CGTGCGCTTT  TCATAAACTG

1951  GCGAAGCAAA  AACATCACG   ATGCTCTCGC  CCGCCTCGTC  TCTGTCTAGC

2001  CTCGCTGCAA  AGACAGCGTT  ACCGCCGTGC  GTTTCGTTTA  TAAACTCCAC

2051  TGCTTGGCGC  ACCATGGCGC  GCTGCAGCTC  TTCTTTGCTT  CTGTTGGTTC

2101  TTCTCTCGTC  AAGAAGCTCA  GGCGGAAACC  GCACTATAAA  GTGCAGAACA

2151  GGCTTCTTCG  CCGCTTTGTT  TTGCCTAACG  CCTTTTGTGT  GCGCGTCATA

2201  TGCCGACCGA  AGGTCTAGCG  TCTTATAAAC  GAGCGGAGAG  GCATCTCTTA

2251  CGACGCGTTT  CGCACTTGTT  TTGTCTTGTC  GTTTCGCGTG  CTTTTCGGCT

2301  GCTGACAATC  CAGCCATATC  TAACGCACTA  CATCTCACCG  CTGCTTTCAT

2351  TTTCAATCCC  TCATATATTA  CCTTTTCTGT  TGTTTTTGCG  AAAAACGCAA

2401  AACTCGCTTT  GCGTTTTTTG  TTCGGCACCT  GCGGCACCTC  CAAAAAACAC

2451  GCTTGCTCTC  CGAGGGTCTG  GCAGGAGCCT  AAGAGGGGGC  ATTCTGCCCC

2501  TGATCGACCC  CATTGAGGCT  CGATCTAAAC  AGACCCCCCA  CAGGGGCGTC

2551  TGTGGGCCGC  TAGTGCGGCC  TTCCGCCATC  TTCGAGCCAT  CTGATCTCTG

2601  CAATTAGAGA  TGCATGGCGC  ATCTCCCATT  CCAGCTCAGA  TATCCCGTAT

2651  CTGTCGATGA  CGGTGTCATA  CAATTCGTCG  AGCCTTGCTT  CGCGCTCTTC

2701  TTTTGTCATG  CCAGTTGCAT  CGCGTTCTTC  CATCTCCTCG  TTCTCCTCTA

2751  TGATGAAATC  ATTTTCGTCC  TCGTCGTTTG  GCCCGCTTTC  TGCTGCCTTG

2801  ACCGCAACAG  CGCCTCCGCG  CTCTGCGGCC  TCGAGCAAGT  TCACGCGTTT

2851  AGCGCGCACT  TGCTTCCACC  CTTCATTGTC  CCACTCCGCG  ACAATTTCAG
```

FIGURE 2B

```
2901  GGCCGCTTTG CTCTGCTGCA TCAACTTCAG CCATAGCTTC ATCGTCATCC
2951  AGCTCGACCA AACCGCATTC TTCTTTCAAG CCTTGGCTCC ACACCAATTG
3001  CCGCCTACGC TTGCCGCTCG TTGCATTGAA ATATTCGAGC CAAAGCCCGT
3051  CATCGCCCGC CTGAAGTAGC TGCCTTGGCG TGCGTCCTTT GCGTTTCCG
3101  CTCTTCGAGC TTGAAAGCGT CAACTCTTCG GCAGCGCCCC ACTTCGCTAC
3151  GTAGTCGCCC GCATTGGCAG CCCCGCGAAC GTCAAACGCC GCATCGTTGC
3201  CCCACATGCC ATACCCTTC AGACATGCAC GCCACGCATC GCCTAGACGT
3251  TGCATCAGAT GCAGCGCTTC GCTTTCATCG CCAGCTCTTA GCAAGACAAT
3301  TTCGTGAAAG TGCGGGTGCC ACCCATTTGC ATAGCTATGA GTAATTTCAG
3351  TTGATGTGAC TGACCCAACA AATGGTAAAT CGCGCCACTC GCGGCGCTGA
3401  CGCAACCGCT GTTTCGCCTT CTTCATGTTT TGGAGAAGAT CAAAAAGCGA
3451  ATCACCTGCT TTGTGCTGGG CTGTCAGAGT TATGAGCACC GGCACAAACC
3501  CGTTGTCGCG CGCCCACGCG AGCAAGTGAT TCATTTCAGA ACGGCGAATT
3551  TGCGCGATGC GAGCGCTACA AACTGCGCAG CCCCACACAT TCCGGCACTG
3601  TGCTAGACCT GAAAAGAATG CCCGACGCCC GCCATCCTCG CCCACGTTTT
3651  GCACGTTTAG CTCAACTGTC GGAGACACTT TTACGTGCCG ACATTTCGCA
3701  ACTTGGTGGG GCTTGTTTTT GTTCAGATTC AACAGAATCC GAGCGGCTGA
3751  ACGCAGATCT GCATAAAGCT GCCGCCTACT GAATAACCTG TTGTTTTCTT
3801  TGTTTTTTTC ATTCGGTTGA CCCCCATTCT GGTCAACCGA TTTACGGTAT
3851  ATACCAAGGG GGGTCTGCCG ACCCCTGAA AAAGCGTCAT CGCCGCGCGC
3901  CTGCGCACCC GCGTTCTTCT TCGATTTCTG AACTGAATGT GATGCTAGTT
3951  TGTGAGACAT GGCCGCAAAC CCCGACGGGT GCGGCGACTA TTCTCTTGAT
4001  TTTCT
```

FIGURE 2C

SEQ ID NO:3

```
   1 CACTTTCGCC ACAAGATCAG GCGCATGATC TTTCTCAGCG TTCAACACAC
  51 ATTTGAGCTC CTGCGCCTGA TCGTCAGTAA GGTAATATCG TTCTTGCATC
 101 AATTTCTCCT TAGTTGGATT GGTTGCACTG GATCTTTGCC CTGACAGCCT
 151 CATGCCTCGA GGCCTCGGCG ATGTCGTGGT GCATTGTATT CTCGCGGCAC
 201 TGCATCGACT TCTTCTCGGT TTCCTTTTGT TCGCACTGGG TACATGGATG
 251 TCGTTGCTGG TCACACACAC CAGAGCACAC CTACAGCTCT CCCATGCGAC
 301 CGCCTTGGCC GCACCGAGAT ACATCGCCTT GTGTGGTTCG CGACTTCGGC
 351 AGCAATCGCC GTGGCAGCTG GATTGGAGCA TCATCAGGCA AGGGCTTCGC
 401 TGACAGCGTT CGTCGTGAAC GCCTAGGGGC TGTAAACCTA AAACTGCCCC
 451 CATTGACCGC CGCCAGAAGA ATGATCCATG TCTAGGGTGC CCCATGAATT
 501 ACCCGCGATA TCCGGTGTGC CGTCGCCTGC AACAGTAGGC AGACCGCTAG
 551 CAGGATTGAT CGAGTGTATG CCACCAAATG TGCCCCCTGA AATATCCAGG
 601 GTGCTCAATT CATCCATTGT ATGCGCTCCA GAGGTTGGGA TTGTGCTAAA
 651 GGATTGAACA GTATGGTCTG GAGTACCCCA CCAGTTCAGA TTCAAAAAAC
 701 TTCCTATCAT TTTGAACATG ATTGGCTTCC TTTTCGATTA AGTTTTCAAC
 751 AAACAGAATT AATCTACGGG CCAGTTGTGT GCAGAAGAGC GACGGCAAAT
 801 TGCTGTTATA GTATTTACGA AAATGGTCGC CAAAAAATAT CTGTCGATCA
 851 AGTGTTTTCT GTAACCATCT GAACTTTTTG ATAAATATCA AGGTGTGAGT
 901 GGTTTATGCG ATGCTTTACA TCTGACATCT GGTAACCGCC CCTGTTTTCT
 951 CAGGGTGTAG AATGCAGATG ACACTGAAAA TACAATGAAG TGAATGAGAG
1001 CCGTTGCCCT GCCCAGCCAA GGCGAAGATT TCATTATCCG CTGAGCAAAT
1051 CTTGTACCAA AGAGGGCTTG CGTTCAATGA GGGCCAGTAG GACTTGAGCT
1101 GGCCCTTGAG GCATACGGCG CTTTTGCTCC CAGTTGAGAA GAGTGCCCTT
1151 CGCCACGCCG ATACTACGTG CAAACTCCGT TTGAGATAGG CCGGTCTGGG
1201 CGCGAATGCG CGCGACATCT ATCTCAGGCA AGCTGATCTC ATGCACAGCG
1251 GCACCGGCCT TTTGCCCAGT CGAAAGGCG CGAGCTTCTT CCAAGCCCTG
1301 CATGATACTG TCGAACGCGC TCATTGTTTG TTGCTCCAAA TGGCGATGAT
1351 CTCTTTGCTC ATTTCGACCG CGGCCGCCTG TTCTGTCGGG GTTAGGTTCG
```

FIGURE 3A

```
1401  CCTTTTCGTT CTTGGCGAAA ACGGTGATCA GAAATATCGG CATGTGGCGG
1451  CCGCCAAACA CGTAGATCGT TCTGAACCCC CCACTCTTGC CGGCCCCTGC
1501  CCTAGGAATG CGGACCTTTC TCAATCCACC ACCCAAAGCG ATGCCGGCCT
1551  CTGGATTTTC TGCAATCCAA GCAATTGCAG CGTCACGTTC CGCATCGGTC
1601  ATGATCGATC GTGAGCGGCG CTGGAACTCT GGCAGTTCAA CTACGGTCTG
1651  CAGGCTTGTC ATTTAGGTAT ACTTCAATGG CGCATAAGTC AATGGCGCAC
1701  TACGGCTTCT TGAGCTGCTC AAGGAGCGCA ACAGCGTGTT CGAGGGTTTC
1751  ACCGAGGCCC CAACCGTTGG CATCTGCTAT TCTGTAAAAA GATTCTATCG
1801  TTTCAGGCGT CGCCTTAATG TTGAACTGCG CGTTTCGGCC AGTCCTACGG
1851  CGCCGCTGCG GCTTGGAAAC AGGGGGCGAT TTAGGCTCCC TGCTCACGAA
1901  GCCAGACGCC TCTGCCGCTT GTTCAGTGCT GCGGTCTTTA GGTGCTATCT
1951  TCGGAGCAGG CGCGAAGCTG CTAAGATCGT TTAGTGCATC ACCAAAACCA
2001  AGGTTTGCGC GTTGCTTGCT CATCACTGAT CCTCTTGGCT ACGCTTCAGC
2051  TTTCCAACCA CTTCGCCCGC AAATTGCCGC GCGTTCTCGA TTGCCTTATC
2101  GACGTTGCTG ACCTGCGACG GATCAAGGTC AGACAAGGTT CCGCCATAGT
2151  CGAACAAGTC ACGATAGGCC GCACGCTCGA CAATCGATGT TTCGCATATA
2201  TCGATGCCAC CGCTCATGAG CTGCTCGTGA ACGTTTTTCA GGGCGCGTGA
2251  GCGAACCGCG GCACTTGTTC GGGTCAGCAC AACGCAGTGC GGTATGGCAC
2301  GCCGCGCCAT CTTCGCTTGG TTGCTGATCA ATCGAATGGT TTTTGCGCCA
2351  CCTCTCGCAT CCATAGACGA GCCCTGTATC GGGATCAGTA CCAGGTCTGA
2401  CATACCGATA GCGTTTGCGA CCATCAGGCT CGCAGTCCCC TCTAAGTCGA
2451  CGATCACGAA TTGAGACGTG CCGGATGCCG CCTCAATCTG GTCAACAATG
2501  CCGTCTTCTG TCACGCCGCT TACGATGGAA ATATTTTCAG GCTTTCCGGG
2551  TAGGCTCGCC CATTGGGAGA TCCAGCGTTC TGGATCGGCG TCGATGATTG
2601  TGACGCTTGC CCCGCCCTCC GAAAGCTGCG TGGCCAAGAT CAAGGCTGAT
2651  GTTGTCTTCC CAGCCCCACC CTTTGGATTG GCGAATGATA TGACAGGCAT
2701  GTGTGATCGT CTCCGCGCTT TTAGGTACAA TATCAGATAG CTAACAGATA
2751  TCCATATATA AGTTACAGTA TCTAGTAGCT ATCGGATATC ATACAATACT
2801  AAAATGGTAC TATTTGGTAT CATATGCCAA ATATCTTGAC TTCATGACCA
2851  CTTGGTTCTG CGGCAGGTCC GACGAAAGAG CCCGGCGAGG ACGCTTACTT
```

FIGURE 3B

```
2901  TTTCTTTGGC TGCCATTTTT TTGCGAGCTT TAAAACGTTA CGACGGAGCT
2951  CATCGCCATC GGGGATATGT GGGTCGAATG GACCTTCTAC CCATTGGGTG
3001  AGTTCCTCGT GTTCAGGGTG TGCGGCGTCG CCGATTGCCT CGATGAAGTT
3051  TTCATATCCG GGCAGGCCGC CGACGTCCTC AGGCGGACAT CTACCGACAA
3101  CATCGACAAG CCGTGGGTAG AGGTTTTCGG GAATCGGATC GTCGACGCTC
3151  TCCGTCTCAA TCAGATGAAC CCAGTAATCT CCGAAATCGT AAACATATCG
3201  GATCGGGTCC GCTACGGCAG TGTTGATGAT GTCAGCTAGG ATGTCCGCTT
3251  CGGAGGTATC CTCGTAGACG CGGATCAGTG CGAAATTGGC CTTGAGCGCG
3301  GCCTTGTCCT TCAACTTGTC CCGTTCAATC ACTTTGCGCG CACTGGCGCT
3351  GTTTTTGCCG TGGTGGCCCG GCCCGTCATA TTCGATGATG GCGCGCACAA
3401  AGCCGTCCTT GCTCCAAATC ACGAAATCCG CGCGCTTTGC GACAAGGCCC
3451  CGCCACAGAT TGCCTTGAGC TTGGATGAAG GCACCGTATG GCACCTGCGG
3501  CGAGAGAATA AGATCAGGTC TGTTCTCGTG CCGCCAGCGG TTAAGCAGGT
3551  TATAGAGCCG AAATTCACTC TTATTCATCA ATTGCTTGCT GCTGTAGAGC
3601  GATTTTCGCC CTTCAACGAA CCAGTAGACA CCCCCGACAA GGGCGATGAC
3651  CACCAGAAAT CCAATTATCA TTGTGAAATT AATGTCGGTC ATGACTGCAC
3701  TCCCTCAAGG CCGAAGTCAG AGATTGCATC TTGACGCAGA GCGACGAGTT
3751  CAACGCCGTC GATGCGGTTT TGGGTGGCGG TAGCCGGGCT GGCGCGGATA
3801  CGCCTACCGT TGGCACGGTT TCTAGGCGAC ATACTGAGGC AAACCGGATT
3851  TCCAGTGGGC TGCGTGCTTT GTTGTAAGCG CGCCATTTCA TCCCCCCGAG
3901  GGCAGGGGAA CGGCTCACAA CTTCCAAAGG CCCCGAAAAA TTCTCGCGAT
3951  GACCCCACCA CGGGATTTGT GCAACACAAT CGGCGCGCGG GACAGGCTCA
4001  TATCAACTTG GATAAGCGCC GCGTTTTTTG CAAAATGCGA GAAAGTGCTT
4051  ATCCGCATCT TTCACGTTGA TGGCCTTGTC ATGCACCCAA GAACGCCACT
4101  CTTCTTCAAG GGAGTAAACA TCCCACCCAG GAGCAAGTTC ACGGGCAGTA
4151  TCGCGTGTGT CGGGATCGTT GAACGGCAAG GCCTGAAAAG TGGTTGATGC
4201  TATAGTTTCC ACCACCTTGG GTCGGAAGAC AGCGTTCTCT CCTTCGATAC
4251  TCATGCTGTA GTCAGGGAAG TGGTCGTGCG CGGTGTCATC CTCAATGATC
4301  TTCGAAAGCA GGCGACGGAA CTCTTTTTTA GTTGAGCCGG AACCGCACTT
4351  GTTTCGCAAG AGCTCCAAGC TACACATCCA TTTTGACTGC GCGCCACAAT
```

FIGURE 3C

```
4401  GCTTTCGCCC TATCTCATAC AACCGCCTTT CGAGGGGCTT TCTGAGCAGG
4451  AAATACCCCC GGCTTAGAGT GAGGACATGG TTGTTCTCGA TCGCATCAAA
4501  GACCCAGTCA GAGAGCGTTA TTTCGACATC AAGCATTCGG CCGTCGCGGG
4551  TTACGCGCAC GATCTCGGCT GATTCAATCA GGCCAAATAC CTTGAAGTAT
4601  TCTTTCCCAC CTTGACGAAT ATTCGTTTCA ATTTGGGTTC CCTGCAGCCG
4651  CCGAAGGGCA TCTTTGAGCA GCTGATAACC CTGACCGGAT GTCTGACGGT
4701  TCGTTGCCAC AAGCAGATCA TAAGCCTTGA AACGCATCGA TCTACTTATT
4751  TTCTGCCCCT CATTAATGGC CGCCATGCAC TGGCTGATGC AGTAGATCAG
4801  CACATCACGG TCATGAACGG TAGCAAGGCC ATAGCGTGAA GGGGAAACCT
4851  CGATCCAATT GTCGTTGTTC TGATAGCGGC GTGGCTTCAT GTCCGGCTTT
4901  GTAGACAGGG TGAACATAGG GTGCTCCATC GAAGCCATAT CCCCCTTGGG
4951  AACCGCATCA ACGATGTCGC AAACGAAAAG GTCTTTTTGT GGATGACGAT
5001  CCGGCAAAAG CGGTGATCGT AGGTTCGTCA TTTCACACAC TCCCGCGCCA
5051  AGTAAAAATT CGTCATTTCA CACACCGTAC AAGACTATCG TCATTTCACA
5101  CACCACTCGT CAAGGCTCGT CATTTCACAC ACCCAAGGAG GCTGTGGATA
5151  ACTCGAGCCG CTATCGTCAT TTCACACACC ATCTTTCGTC ATTTCACACA
5201  CCATCTTTCG TCATTTCACA CACCAGGTGT TATTTTTTTT ATAGTTATAT
5251  CAATTGATTA CGAGCTGTTT TCGGAGCTGT AACTCTATTC TAACTCTATT
5301  CTAACTCTCA TAGCTTGCCA AAATGGCACC TCATATCCCG GATATCCGGT
5351  TTCATTATGA AACCAATCAA CAACATTTAC GGTGTTTTTT GAGGAGCAAC
5401  ACTGTCCCAA CGCAGGTTCA AACCGATCAC GCCGAATCTG CAAAGAAAGG
5451  GGCAGTGCTA TGTTCATTTG GTCACTCGAG GATCACCCGA ACCACAGGTA
5501  AGCCCTCACA TGCTATGTTG ATACCTCCAG GGAAGTAGCA AAGGTCCTCA
5551  CGACCACCAC CTGCAGGATC TCCATCAGCG AAGACAACTG TCGCATTGAA
5601  CGCTGGCGCC GGCTTGTACG TACTCGGTAT GGGTGAGAAG TCAGGCATAC
5651  CTGGGAGAAC ACGACGAAGG ACACCGTGGT TCTCGAGGAT CCCGTAGAAG
5701  ATATCGGGCG TCCCATTATC CACATAAGCC GCACCATAGC GATCCTCCCC
5751  GTAGAGATAC TCACGGAAAG TTTGCATATG CCGCCAGCGA GAGCGAAAAA
5801  GGGGAACCCG AATAGCGAGA TCCTGATCGC CAACCAAAT GTCAGCCATG
5851  ATGAACATGG AATATTGATT GTTCCACGAC GACAAAGCCG CAAATTCCAT
```

FIGURE 3D

```
5901  GAACCGTCTG ACCGCATGCA GGTCAGAGCG CTTTGGCTCC ATACGATGAA
5951  GAGGGTTTAC ATCTCGTTCA ACACTGCGAC GATCCGCCTT CTTCACCGCG
6001  CTCACAAATG GACTGCGATG TAATCGGCCC TCAAGGTAGC CTTCAAGCTG
6051  TTCCGCATAG GCCTCATCAC GCTTAGAGAC ACTCTCCAAG AGGCAGTCAG
6101  AAACGACCTG ACGCCAGTAC CCATTCCCAC GCGCTGTGTC GTGACCTATG
6151  ACGGGCCTCT GATTGTATCG CAGGGAGAGG TGCGTAACCG GAGACTCGAA
6201  GCTCTGAGAC CATTCCCAGA GGCTCTGAGC CATGGGATCC CACGAAGGAA
6251  GGTCCGTCTC TGGTTGCTCT ATCTCGCCAA AACCTAAATC CTGCAGCTGC
6301  ACATTCGCAG GATAGACTTT GAACATCGTT CGCACCTTGC CGAGGTCATG
6351  AACAAAGCCC GCGATAAAAG CCGCAAGATC GCCCGCCTCT GAGGGGACGG
6401  CCTTACTGAA CTCACTGTTG AAGAAATCTA CCGCAAGCCC AGCTGTTTCC
6451  AGGGAGTGAT AGAATAGCCC ACCGGCTGTG CGGTGGTGAT GTGTAGATGA
6501  AGCTGGGAGG CACAGCATAT AGTCGTGGCC TCCGCGCAAC ATTTGCCTCA
6551  CCAAGAGTGT TTCTTTGTGA GAGAGGAAGG GGAGTTTTTT GAGCTGCTCC
6601  TTGATCAGCT GCTCATAGCT TCCAAACGTC ACATGCGGGT GCAATATCCG
6651  GAACTGAGCG TTGCGCAGGT AGCGCCCGTA AGACAGGATG ATGCGATCGT
6701  CATAAAACAT TGGCGGTTTC CTCAATCGAT ATTTGCTCTT AGTTGGTAGG
6751  TGCCCGTATG GGCGCGGCAC AGGTTTCTCA GCTGTGCCAG GCGGTCAGTG
6801  CGATAGCGGA TCCAGGCGAA GTTGGCCTCG CACAGAAGCA GTTCTCTACG
6851  GATGGCGTCT GGAAAGCGCG CGAAGATCCG ATCGCTGTAT TTGTACTTTC
6901  CTGACATGCG GATCTGTTCG GTTGGGGTGA ACTTGTCACC TCCCATCCGG
6951  TAGCGGGCCT TGCCTTGGAA TTTGACCCAG TAAATGCGCG GGCCCAATGT
7001  GTCCTCGCGG ATTCGAACGA CAATGCCCAA ATTCAGCGCC TCGGCGCCCG
7051  CGTCCATTTT GCGATAGGCC TTCAGGGCTT CGACAGCCCG ATCCTGCCAA
7101  TAGCGCGCCC ATCCTTCCAA GTCATAACCC ATCGCTGGAA TGGATCGCAA
7151  AAGCTCAGGC TCCCAATCGG AGTCGAAATC ATGAAAGCGC ACTTCGTGCG
7201  AACAGCTCTC TTGGGGGTGT TCTTCAGACA TGCTGTGCTC CGACCAAATG
7251  GCGCGCCGAC CAAAACAAGA AGGTTGGGTT CAATGCCGGG ATGTTTCTGT
7301  CTGCGTTCAG ATAAAGCCCA TGTTTCCTAA TGTGACGGGA TGGTAGCTCC
7351  GTCACATTAG GGGGCGACGC ATTTTGCGCG GCACATGGCG CGGAGAGCCC
```

FIGURE 3E

```
7401  GCAGGCAGGC GGCTGGACGG ACGAAAATGG GCAGGGGCCG CGCTGAGATC
7451  CCTTGAAAGC CCATGGGCCT AATGAATGGC GCTCACACAG CCTGTCATGC
7501  GTGTACTTTA CGGGGAGGTC TCGCGATGAG GTGAGCGCCC GCGGTCTCTC
7551  GTCTTGGTCG TGTCTGACCG TATGTGTCCG TCGAATAAAC GTCATGATGA
7601  GGTCCTGAGA TAAGAACGAA CAGGATCGTT GACGGAGGGC ATCCGTCTGA
7651  CTGTCGTCTG ATGTTGATGG AAAGTCGCCG GCTCTAGGCG GCCGGTCTCA
7701  ATTTGGTGGT GAGCAGCTCT TTGCGCTGGG GGGCATTACG ATGCAGATCA
7751  GCCGTCCAGT TTAAATCGGG AGGGGTGAGG GAGGTCGGGG CGGCCGTGCA
7801  CAAGACAATG GCATCCGAAA GCCGGTCAAT CATTGGGCGT ATTTGTCCTA
7851  CCCATCTGTG CCAATTCATA GCAAAAATCC CGAACCATCC GTTTCGTCAC
7901  ACCTATTGGC TAGGGGGAGG TGGGGATGGC CGTCAATGAA AAATATCAGG
7951  GATTGAGTTT TATAATTAAC TGAAATTGCT AAATATTTTT GGAAGGAATA
8001  TTCCTTCCGT AGCTCGTCTA CTCATTTATC CCTTTTCGAA AAAGACTTA
8051  ACAGCGGGCC AACTGTTTCG CATGATGCGG ACAAGAAAAA TTGGCTATCA
8101  TGGGAGTGTT CGGGTGGCGC GTGGGACTAA GACAGCCAAA AGCAAAAATG
8151  CTGATCCAAT TGTAGCAGAA TGCTTAAAAC TGATTCGCGA AGACAGTGGG
8201  TATGAGAGAG ATGAATTCGC CGAACTTCTA GGGGTGCAGC ATAAAACGTA
8251  TCGCAACTAC GAAGGCTGTA TATATCCGCT ACCGTTAAAA GTGGTAAAGA
8301  CGATACGTGA GAAGTTGGGC TATGATCTTG CGGATCCTGA TCTGACTTCA
8351  GACGCGATCA TCACCAAAAT TGCAGAGCAG CGACACGATG TTGCAGCCGC
8401  TCCTGATCTT GCCGCGACAG AGCAAGTAGC GAAGGGCGTT AGTTGCCCTC
8451  AGAGGATACG TACCTGCCTT CAAGCTTTCC GGCAGGAACT CATTGGTGTC
8501  CAGAGCAAGC GCAAGCATGA TATTCGAGAC GCAGTTTTTG TCGGAGCAGC
8551  TGCATTGTTT GCTTTCTGCT TGGTGGTACT ACGCACTGAA CCGCAAAATA
8601  TAAGGTTAGA GTCTATCTAT ACCCTTATGC TATCCGTGTC CTTCTTGGTT
8651  GCGGCGTCAA TTGTCCCGTT TCAGGCTATA CATATGATCC AAGCCGCCTA
8701  TCGGTCGCGA CGTTGACCAA CAATACTAGC CCTCCCCGTA TGCCCGTCTC
8751  ACAGGGAGGG CCAAAGCTAC CTTGGCGAAC GACTGTCAGT GCACGAAACG
8801  GGTGATTAAA CGCAAAGTGC TGACTTTTTT TCCCCCGATA CCGATGGTTC
8851  ATCAAAGATA TATCGACTGA GCAGATCGGT GTCCGGGGCA CGCGTGTGCA
```

FIGURE 3F

```
8901  TTGCTTCTAG GCCAGAAACT GTGAAGTTCT CTTCCACGTC GGATTCCGGC
8951  ACAAGGAGGT AATGCCAGGG CTTCTCACCG CTCTTTGCAC CGGCTTGCGT
9001  CGCAATATGG CACCACAGGC TTGCCGCATC TGCTTTACGC AGAACCTCGG
9051  TGGCGGTCAT TTCCGATTGG CGTTTTACCT CGATGATCAG CTTGCCTGTA
9101  TCGGTTTCGA CAACGAAATC GGGCTGATAC GGCGCACCGT GATTATCGAA
9151  AATTTTGAAC TGGTTGGGGC CAGGTTTCAT CCAAAGGCGG ACCGAGCTGT
9201  CTTTTTCAAG GATGATCGCC AGCTTGCGTT CTGGATTAGA GTCGAACTTC
9251  GCATACTGAT AGCAGCCCTT CACGAAGCCA GTGAAGATAT ACTTCCGGAT
9301  CTCCTGCTTT TGATCTGGCG GTGTTTTGAA ATCCCGGATG AAGCTCGTAC
9351  CGGCGGTATC GAAGGTCTGC GGACGCAGCT CGCCGAATGC AGAGGTCAGA
9401  GAAACACGGT AGTTCGTGTG CTCACGCCAC ATATTCTGCT TTATTTGCGA
9451  GAAAATGCTT TCGGCCATCG CCTTCGCATG CCCCCGGACG ACACTGCGAG
9501  TTTGCTCATC GTCGTCCGCG AAGCGGTTGC GGGTTTGGGT GACTGCCTGC
9551  CCAGCCAGAT CATACAAGAT GGCAGCATGG GCGTCATAGT CGATCTCAGG
9601  GTAGTCGATC AGCCGCGCGA CGATGTAATT CTCCAGCCGG TTTGCGGTGT
9651  CCCCCTTATC CTCGCTGGAA ATACGCGATG TCTTCTCTGT ACGCAGAGCT
9701  TGGATCATGA GCTCATTGGA CAACGGCTGG AAGTTCCAGC TCTTCATGTC
9751  CAGGTCGAAG CGCTTGAAGC CGAAGGAAAC TTGTTGCTGC GGAGTGATCG
9801  TGAGAGCAGG GATCGCAAGG GTCCGCTCCA CGAAATTCTT GCACAGCTCC
9851  TGAGCGACCG CGACGGCCTT TTCCTTCGTG ATGCTGGGAA GGAAACCTTC
9901  TTCGGGTTTC TGTGCTGCAA TGGCTGCTTC CGCGATGCGT TCGATCACCT
9951  TGGGGTCGTT GAGATCGCGG ATCGAGGACA CTTCCTTGCT GAGCTGGGGG
10001 ATCACAACAC TGAGCACCGT GCGGGCGACC TTCAGCTCTT CAGGCGTGCT
10051 GAAGCTGAAA GGCGCTTGGG TCGGTGCCGC AGACGTCGGC TTGGCGACTA
10101 GCTGCACAGG CGCGTCCGAA GCTTTTTCGT CATCCGCGAC GACGACTGTC
10151 GGCTCTGTCT TGGCCTCTGC CTGAGCAAGC ATCTGGTCGA GGATGGAGGG
10201 TGCCGAGACC GAAACAGGCT TCGAGGGCGG CACGTCACCA CCCTCACCAA
10251 TCGTCACCTG CTTCAGCTTG CGCGTGACGC CGTTCTCTTC CTTGGCTTTC
10301 TCGATCAGCT CGTTGAAGCG TTCGTGGGCA ATCACGGTCA GCGTGTCAAC
10351 CACTTCGACG CCGGTTCGCT TGCCATAGGG CAGGCGCAGA CCGCGACCGA
```

FIGURE 3G

```
10401 GCGTCTGTTC GGTTAGGATG TCCGAGGCCG AGGCGCGCAG CGGAACGATG
10451 GTGAACAGGT TCGAGACGTC CCAGCCTTCC TTCAGCTTGT TGACGTGGAT
10501 GACGATGTCC GTGTCGCCGG CCTTCTCGAT ATTCAGCAAA CGCTGTGCGT
10551 TCTCGTCGCT TTCCTCGCCG GTCAGCTTGG AGTGGATCTC GGCCACGCGC
10601 CCCTTGTAGC GTCCGCCGAA GAACTCGTCC GACTGGACGA ACTCATTCAC
10651 CTGCCGGGCA TGGGTCGTGT CCTGGGTAAC AACCAGCATG AAGGGCCGCA
10701 CCACCTTCAC GTCATTCTGG CGGGCATAGG TTTCCAGCGC CACCTTGACG
10751 TGCTCGTGGT AGTGGATGCC GTCTTCCAGC TTGATCCGTT CCAGCGTGTC
10801 TTCGTCGACG GTCTTCGGGT TGAAGTTCGC GCGGGTGCCG ACAGCCGGTT
10851 CCTTAACATA GCCGTCTTCC ATCGCGTCCG GCAGATCGTA GCGGTAGACG
10901 ACGTTCTTGA AGGGCTGCGA GCGCGCGCCA ACGGTCTTCG GGGTCGCCGT
10951 CACCTCAAGG CCGAGGATCG GTTTCAGCTC GGCAATCGCC CGCGCCCCGG
11001 CCGAACCGCG ATAGCGGTGC GCCTCGTCCA TCAGCAGGAC CAGGTCATCC
11051 AGTTCGGAGA GGTAGGAGAA GTAGCTCTCG CCGATATATT CCTGAAGGCG
11101 CTTGATCCGG GGGGCGTTGC CGCCGCGTGC TTCGGAGTTG ATCTTCGAGA
11151 CGTTGAAGAT GTTGATGATC GCGCCTTCTT GGCCGAAGAG GTCGGTGCCA
11201 CGCACACCGC GGCCTTCCTC GTAGTTCTCG GCGTTGACGA TCAGCGGCGC
11251 GTTATGGGCA AAGACTTCGA TGCCACGGAA GACGTATTTC GGGCTCGACG
11301 GCTGGAAGTC GGACAGCAGC TTTTCATAGA TCGTCAGGTT CGGGGCCAGA
11351 ACGAAGAAGT TCCGGCTTTT GCCGATCATG TAGAGGTAGC TGATGAAGGC
11401 GCCCATCAGG CGCGTCTTGC CCACGCCGGT CGCCAGCGCA AGCAGACGC
11451 TCGGGAAGTC GCGCTCGAAC TCCTCGAAGG TCGCGTCGGC CAGGTCGCCA
11501 TAGACCTCGC GCACGGCGGC GCGGGCCATG TCGATATCGG CTTCCTTCGC
11551 GGGGCCGACG AGGTCGACGA TGTCATCGAG CCGCCGCAGC GCCTCGGCCT
11601 GCGGCTTGCG CAGCGACAGG CGTTGGTTGA TCTGAAGGAC GGCGCGTTTC
11651 GGGTCGGTCG TCTGCATGGC TCAGTTCTCC TCTGCGCCAA ACAGATCGGG
11701 TGTGTCTGCG GCTTTGGCCT TGGCCGATTT CTTCGGCGCG GGGGTGTCTT
11751 CGATGTCGTC CGGCTCATCC TCTGCCATCG GCAGGGCGTT GATCTTCAAG
11801 GAATAGTCAT CCTGCCCCCA TTCGCAGCGG TCAAGCACCA CGCGCGGGAT
11851 CTTCTTCAGG GTCAGGTTGC TCAGGCTTTC GCCCTGGGCC TCATAGGCCA
```

FIGURE 3H

```
11901  TGCAGCAGAT  CAGCAGGCTG  CGGTCCTCGC  CCACCTCGTC  CGAGATGGCG

11951  CGGAGCTGTT  CGATGGTCAG  GCTGGCCGTT  GTCACATAGA  TGAAGGCGTT

12001  CTCCGAAGCC  TGACCGTGCA  TCCAGTAGGC  CTCGGTTGAG  GGCGCGTAGA

12051  CATAGTTGAA  ATGCTTGCAC  ATGGCCTCGG  CCAGCATCTC  GGCATTGTAG

12101  TCCTTGGAGA  TGACCCAGTT  GCCCCAGACA  TCCTTCTGAA  GCAGAGATGG

12151  CGCAAGACGG  AAGAAACGGT  AGCCGCCGCC  GCCTCTCCAG  TTTGTGGCCT

12201  CGGTCACGCC  GCCCTTATCG  GTGCCGTTGA  TGACTTTTTG  CAGCCGAGGC

12251  GCGACATGGG  TTTTGGCATG  GTCCCCCAGC  TCGACCATGA  TCCAGCGGCG

12301  GCCCATCTTG  TGGGCCACTG  CACCTGTCGT  GCCAGAACCA  GCGAACGAGT

12351  CTATGACAAG  GTCGCCCGGT  TGAGTTCCTA  TCTGTATAAT  ACGCTCCAGC

12401  AGTTTTTCTG  GCTTCGGTGT  AGCGAACGTA  GCGTCTCCCA  AACCAAGAAG

12451  CGTGCGCAGG  TCATTGGTTG  CTTCACGGGT  TGTACCAGCT  TCTTCACCGA

12501  ACCAAATGCT  CTCAGGTACG  CGGCCTTCTT  GATCGCAGAG  ATAGATCTTC

12551  CGAAGAACAC  GCGTGTCCTC  GTTTAAGAAT  GTAATTTCCC  CGGTCTCTAC

12601  TTTGCTGGCA  AAGGTCTCCT  TTGACCACCT  CCACCCTTTC  TCTGGCGGCG

12651  GAATGATCTT  CCCAGAAGGG  GTAGTAACAT  CGAACATGAG  ATTTTCTCTG

12701  TAGTTCGGAC  TACGTACATC  TCCTGCTCGC  CAAGGTCCTT  TTGGATCTTT

12751  GTCTGGATTA  TTATAGTTTT  TGTTGTGCTC  AGGCTTTCTG  GGCAGAAGGT

12801  TGCGCGAGAA  CGCCTCTGTT  TTCCGATATG  CTAGAACGTA  ATTATGATGG

12851  AGACTGACGG  TCTTGGCGTC  ATTTTTCCCT  TGAACGCTAT  GCTGCCAGAT

12901  GATCGAGCCG  AAGAAGTTCG  ATCGGCCGAA  AATCTCGTCG  CACATAACCT

12951  TGAGGTAATG  CACTTCGTTG  TCGTCAATTG  TCATCCAAAT  GGAGCCGTCT

13001  TCAGAAAGTA  GGTTCCGAAG  AATTTCTAAC  CGATCTCGCA  TCATTGTCAG

13051  CCAAAGCGAG  TGCTCCAGCC  CGTCATCATA  ATGCTCGAAG  GCCGACCCGG

13101  TGTTATAGGG  CGGGTCGATG  AAGATGCACT  TAACCTTGCC  CCGCACGGCA

13151  GGGTCGGTTT  CCAGCGCCTT  GAGTGCCAGC  AGGTTGTCGC  CGTGGATCAG

13201  CATGTTGTCG  AAGATGTCGC  CCTCGCGCCG  CGTGCTGGCG  TGATGCGAGA

13251  ATTCCGGTTC  TTCGATCAGA  ATGCGGGGCT  CAAGCCGCGG  GCGGTTGTTC

13301  TTGCCGATCC  AGGTCAGTTC  AAGTTTGGTT  TTGGCGGCCA  TCAGGCAAGG

13351  GTCCATCTTA  CAGTGAATAG  GGTCGTCATT  TCGGGGGTCA  GGTTCAGCTG
```

FIGURE 3I

```
13401 ATCTGCGATG TCATCAAGCA TCCGCTCGCG CTCAGCGTCG ATTTCGCGCA
13451 GGCGGGTGTA AAGCTGGTGC TGAAGGTCAT CCACCTGCCG CTGCAAGGCC
13501 TTGGCCTCGC GTTGCAGGGT GACCTTTTCT TCCAGCCCGA TCGTGGCACG
13551 GGCCAGTTTC TTCTTCTCGG TCGCTTCCTT GTTCAGCGCC TTGATCTGCT
13601 GGTCGAAGGA CACCTTGGCA TCCTCGCGCC AGGCATCGAG CCGCTCTTCC
13651 TCCTCGTTGA GGAAGGAGCT GAGCCGATCC TGTGCCATGC CGATGATCGC
13701 GGTCTGGCGC GCGTTCAGGG TTTGGGTCAG GTCGCTTTCC GGCAGGGTGT
13751 CCGCGCCAAG GCCCTCGGTC GTCGCCGGGA CATAGAGCAT CCGAGAGGCC
13801 GTTTCCGGGT CGATGGCTGT TCCGCCGTCG CTGAAGGCTG CGAAGACCAG
13851 CTCGTCATAG ACCTTGGCTG GGGTTTTCAG TCGGACCCGC GCCACGCGCA
13901 TCCAGCCCGA CTGCCCCCTG AGCTGGGCCA CGTCGCCCAT GTTGCCCTGA
13951 TAGGCGCTAT AGTCGAGGCG CAGCATGGCA GGGACCAGAT CGCGCGACTT
14001 GGCCTTCTGG ACCAGCTGAT CGGCCAGCCC CTCGTCGCCA AGGCGGAAGA
14051 AACGCCAGCC GCGCTCGTCA GCCTCGGGCC ATTCGCTGGA CCAGGTTTCG
14101 CCCCCGTAAT CGAAGCGCTG CGCATGGTCG TCGTGGAAGC GGGCCTCCGG
14151 CAGCTCGGCC CGCGCGACAC CAAGGAGGGC GCGCTTGAAG TCACCGATGG
14201 CGGAATGCAC GGCGTCTTTC CGGCCAAGAA GCCGCTCGAT CACCTTGTCG
14251 TCCATCTCGG CCAGCAGCTG ATCTCGGACG TTCTTCTTCG CCTCGTCGAT
14301 CTCGACGCTG AACTCTTCCT GAAGGCGGTC GAAGGCGGCG TCGATCTGGT
14351 CCGTGGTGCG GCAGGACTGG ACGATGTCGA GGATGCGCCG CTCGATGTCG
14401 ACGCCGGATT CAATGACGCC CAGAACCTCG TCGGAGGAGC CGAACACACC
14451 CTCGAAAAGC TTGAACTTCT GTTCCAGAAG CTGGTGGATG CGCGCTTCAG
14501 CGTGGTTCTT CCGGTTCAGG AAGTTGATGA CGGTCACGTC GATCTTCTGG
14551 CCGTAGCGAT GGCACCGGCC AATGCGCTGT TCGACCCGCT GCGGGTTCCA
14601 GGGCAGGTCG TAATTGATCA GCAGGGAGCA GAACTGGAGG TTGATGCCCT
14651 CGGCGCCGGA CTCGGTCGCG ATCAGAATGG TGCGATCGTT GCGGAAGGCA
14701 TCGACGATGG CGGCCTTCAT ATCGGCGGTC TTGGAGCCCG AGACCACATT
14751 GGTGTCGCCG TGCTTGTCGA GCCAAGCCTT GTAGAGCGCT TTGCTGTCTG
14801 CGTCCGAGTT GGAGCCATTG AGGACGACGG TCTGTCCCTC GAAGCCGCTT
14851 TGTTCGAGCA GATCGCGCAG ATAGGTTTGC GTCCGCACGG ATTCCGTGAA
```

FIGURE 3J

```
14901  GATCACGGCC  TTGCGCTGGC  CGCCCTTGGA  GACGATCTCG  TCGAGCACGT
14951  TCGGCAGGCA  GTCCAGGAGC  GCCTTGCCTT  TTGCGTTGTC  CGAGATGGAT
15001  GCGGCCAGAT  CGCGGTACTG  GGTGAGCCGC  TTGATTTCCG  CTTCGAGCTG
15051  AGCGGGATCG  ACGCGCTCAG  CATCTTCGGT  GTCGTCTTCG  ATCGCGTCGG
15101  CTTCCGAACC  GGAATCCGCC  TCGCGCCAGT  CCTCGGCTTC  GTCGCTGAAA
15151  CCATCAAGGT  CATCGAGCGT  GTCTGCCCCG  ACAACACGCT  TCGCCTCAAG
15201  CCTGCGGATC  ATCTTGTCGA  GGGTCTGCAT  CACGGCGAAG  GAGGAAGATC
15251  CGAGGATCTT  GCGCAGCATG  AGCGTCACAA  GATGACGCCC  GTTCTGCCCC
15301  AAGGCGATGG  TGCTGGGGTC  TTGGAGATAC  TCGGAAACCT  TTTCGTAGAG
15351  ATCGGTTTCC  AGTCGACCAG  GCGTGAAGTC  GAAGGTCTTG  GGGAGACGGT
15401  TGGTATAGTT  GATCAGGCCA  GCGCGTTGGA  CTTGGCGGCG  CAGGGTTCGT
15451  TTGCAGATAG  GCTCAAGACG  TTTCGCGAGC  AGGGCCTGAG  AGGTCAGGCC
15501  TTCTCGTCCG  CCAAACTCGC  TTCGGAAGGC  TTGTTCTGAA  CCGAAGTAGG
15551  TTTCGTCGAT  GATGCTGATG  AGTCCGTACA  GCTCCATCAG  GTTGTTCTGA
15601  AGCGGAGTCG  CCGTCAGAAG  GAGTTTCTGA  CGCCCAGCCA  GTGCCTTTCG
15651  CAGAACCGAA  GCCCGAGAGT  TTTCGGCGGC  CTTGTAGACG  TTACGCAGCT
15701  TATGAGCTTC  GTCGAATACC  ACGAGGCTCC  AAGGCGTGCG  TCGCAGAGTG
15751  TCTGCAATTC  GTGCGGCGTA  CTCGTAGGAG  ACGATGATAA  TGCCTTCTCC
15801  GCGCCCTACC  GGGTGCGGAG  TGCCTTCGTT  CTCAAGGTCT  TTGACGCGCT
15851  TGGCATCAAG  AATGAACGAT  GGCAGCGAGA  ATTTTTCACG  CAGCTCGGTC
15901  GCCCACTGCT  TGCGCAGAGA  AGCAGGGACG  ATGAGGAGAA  TGTTTCTCTC
15951  ACGTTCCCAC  CAGCGCTGGC  TAATGACCAG  CGCAGCTTCG  ATTGTCTTCC
16001  CCAAGCCTAC  TTCATCGGCC  AGAAGAACGC  CCTTCGACAA  TGGTGAGCGT
16051  AGGGCAAATG  TCGCAGCATC  CACTTGGTGA  GGGTTGAGGT  CCACCTTGGC
16101  TGCCGAGAGG  GACTGCGTCA  GAGCGTCTTC  TTCCTGAATG  CCTTCGGATG
16151  TCAGGTGGTG  CGCAAAGAAC  TTTGATTGAT  ATTCAGAAAA  CTGGAAGAGC
16201  AATAGGTCAG  GCTCCAAGGC  ATATTAGTTA  AGGGAAGGTT  GTTCTAAATG
16251  CTGTCAAGTT  ATGGCCTGCG  GCTTGATCGG  CCAGCACGAA  GGACTCCCTT
16301  CTGCCCAGGA  TATTGGGCCT  TCTCGTTATC  ACGCCACTGA  AATGTCACCT
16351  GTACTGCGAT  ACCATGCTTG  TCGGCTATTC  TGGAAACTTC  CTTCCAAGCC
```

FIGURE 3K

```
16401 TCCTGGGCTG ATTGCCCTTG GATAGAGATG CCGAGGTCAG GGTAATATCG
16451 GAATCCTTCC TCTTCGTAGC ACGCCGTCTT GGTAGGAATC TGTATGGCCT
16501 CAGCTAGGTG ATCTCCGGAT AGGCCCTTAG CCTTAAGAGA ACTCACTGCG
16551 CCGAGAAGAA TTGCTGCCCA GTTTGGCTTG TCGATCTTCT TGTGATCAAC
16601 CTCCGCAGAT AAGACTTTTG TAAATGAAAG GCCTGGAGTG GATTTGAACT
16651 CCATGAAGCT GCTGATTTCC GACGTGGGAT CAATGCTGAT CTCGATGTCA
16701 CGCTCTAGGT CAAGCGCTGC CATCTTCTCC CGTACCAGCA GCATGATCGT
16751 TTCTGATGGG GTTTCTGTCC CCATCCAAGT CGAGATGCAC TTCAGATCGA
16801 CAAAAGTTGG GTCGTTCAGT CTGACTACGG GCATAGGCGT CATCCTTCTA
16851 TATTCATATA GAATATGTTA CATATTCAAT ATTATGGTGT CAATGCTAGC
16901 GTTTGATTGG CAACCTGTCC TAAAACGGTC GTTTTTGGGC ATAGTGGGAT
16951 GAAGTGGTCA AAATATAGGC CTTGATAATT TTGAACATGC GGCTACTTTT
17001 GGACAGGGTT TTTTGACACG GAGGGCCATA CATTGACAGA GCAAGGCCGT
17051 GTTTTTGCCT ATGTACGTGT CTCGACACTC GGGCAGACAG TCGCTGGACA
17101 GATGCAGGAA ATTGCGGCGG CTGGCTTTCA GCCCCCAGCG TATCGTGTCG
17151 TTTCGGAAAC CATCTCTGGC AGTGTCCCGG CGATGCGGCG ACCAGAGTTC
17201 GCGCGCCTAG TTGATCGCTT GGAACCTGGC GACATTCTAG TCGTGTCGAA
17251 GCTTGACCGT CTCGGACGCG ACGCAATCGA CGTTACGGAG ACAGTCGCTG
17301 CGCTCTCGCA GATACCTGTC CGAGTTCATT GCCTCGCTTT AGGTGGCACG
17351 GATTTGACTA GCTCGTCTGG ACAGTTGACG ATGAACGTCC TCAGCGCCGT
17401 TGCGCAATTT GAGCGCGATT TACTCCGTGA GCGGACCAGT GCAGGCCTTG
17451 CAGCTGCAAA AGCCAAGGGA AAACGACTAG GTCGTCCTAA AGTGCTGACC
17501 GAGGATAACG AGAGCGAAGC ACGAGCGGCT CTCGCCAGAG GGGAAACTGT
17551 TTCTGGGATT GCAAAGCGTT TCAACGTCAG TCGGGCGACG ATCGGCCGCC
17601 TAAGAGATAG TTAGGCTATC TTGCCTATGT CGTCGTGACG AGTCCTCCAA
17651 ATACACGGAT GGCTTCACGC TCCCATGCAC GATTAAACCA AGTAACATGG
17701 CGGCTTACTT GGTCCTTAAT CTCAGGGCAT CCATGATGT CCGCTGCCTT
17751 GTAAGCATAC CGCAAGAAAT TTCGGCGTTT TCCAAGATGG GTATAACGCG
17801 CCAGGCTTTC TCGCTTGAAT ACTTCAAACG ACGGTACGTT TTTCGCCTTT
17851 GCGGCGATCA TCTTGGCATG AATGCCCCGG CGCATTTTTC CTCGGTAGGC
```

FIGURE 3L

```
17901 ATCGAGTGAC GAAGGTCGGA TCTTCGTTTT CTGCCCGTCG AAGGTGAAAC
17951 CCAAATACTG GATAGGTGTG GCAGAGGCCA ACAGTCCGTC CTTGAAGTCG
18001 GCAGTGTCTG TTTTGTCGAT GGACATGGAA AGGCAAAAAT CTGCCAGCAT
18051 TTTCTCTACT ACTGCAACCA CATGATGCAC CTTCGCGCCT AGAGGCAGAG
18101 TGACCGCGAT GTCATCAGAG TATCTTCGGT AAGATCCCCC TGCCCTAGAG
18151 CACCAAGCGA TCATTTCACG GTCAAAGTT CGAAGATAGA TATTTGCATA
18201 CAGGCCGGAC ACCGGGGTGC CCTGCGGGAT ACCGAACGTC TGGTCATGCT
18251 TCCGAATGAG GCCATCCTTT CGGCCTCGGA CATGATCCGA AAAGTCTGAA
18301 GGTGAGCATA TCCTTCCGTG CCCATTTCGC TTTCGACCAA GAAGTTTGTC
18351 TAGATCTTCA GTCTCAACCC ATGAGTAGCG GGTCACGTTT TTCCAAACGC
18401 TTGCATGGTG CCCTTCCAGT CTTGTTTCGC CTATCAAATC GGCGATCTCA
18451 TCGCGGAGCA AGGTGTGATC GAGACAGTCA AGAATCCGG AAATGTCCAT
18501 TGCGAAGACC GTGCAATCTC CACGAGACTT AATCTCGTCG AACAACGCCT
18551 TTGCATGGTG AATATTAGTG CCGCCCCAC GGCGATAGGC TAGCACGGAG
18601 TCTGATGTGC CGTCGCGCCA TAGCGCCCGC TCGTACATTC TATTGAGATG
18651 TCCCGCGTAG GCTTGCAGGT AGGCTGCATC CTCATGACTG GCGAAGCGGA
18701 TCGGTCGCTC TTTCACTTTT ACCTCACGGG CGCCATCCTT GTTCCTGACA
18751 TACCTTCTGT TGACGTCAGT AAACCCAAGT AAAGGTAGAA ATCTGTGAGG
18801 CTTATCTTCG ACCGAGAAGT CAAACGACAG CTCCCGATCG ACTAACGGAA
18851 GATCGAAATG CTTGTATTTG CGTTCCTTGG ATATGGCCGG AAGCACAAAG
18901 TCGTCGGTTG ATGGATCAAA CTCGTTTTCA GACGGCAGGT AAAACCCGGG
18951 CATAGCGACT CCGTTCGTCA AATGCCCGGG CTATTGAACC TAGCTCCCAT
19001 CAACAGGCAC CGAGGTGCCC TCCGGTACGA GAAAACCTGG CGTGGTATGT
19051 TGTAACCACG ATGTGCGAAG GATGCGCCAT GACCGAAATC ACGACCACCC
19101 GGTGCCGCTG GGCGCGGGTA GCGCTTGCGG GCCTTAACAC TGGTCATCCG
19151 GGTCCACGCC CCGGGGCAAA ATATCAATTA GGTGCTACCT AATTGAATGC
19201 AAGGGACGC ACCAAGAATA AAAGGACTTT TTCAGCTTTA GTGGCGCCTT
19251 ATAGTGGTCA TCTGGAACCA GGACAAAGAG ACAACCTTCT AGGTAAGATC
19301 CTCGTAAGTT CGTATCAGTT ACGGTGTCAG ATAGTAGCAG ATAACGCACG
19351 GCGTTCTGCT GGCGGAGGGC GAGAGAAATC TGGTTCGCTG TGAGCGGTAT
```

FIGURE 3M

```
19401  TTCTTGCCCA  CAACGCGGCC  CTTATTCCAG  TCTAGTACAG  GCTTGGCAGC

19451  CAATTGCCGC  GACTGGCATA  GCATCGTGCT  CCTTGATTAC  ATGCTAAAGA

19501  GGTACTTTGA  GGTCTTAGCG  GTCATTCGAC  GATTTTGCTC  AGATAACAGC

19551  GTAAGTAAAC  GCTGCCCCAA  GTTTCAGGAT  CTAGCGCCCA  ACGATCTTAT

19601  CACAAGAGAC  CATGTTAATG  CGTCTATTAC  ATTAGGATGG  TTCAAAGTTG

19651  GGTTCGGGAT  CATCTGGTAT  TGGGGTTCCA  AAGACCAATT  CGTGC
```

FIGURE 3N

SEQ ID NO:4

```
   1  GCGTGGCCCT TCCCGCCGAG CTGGACGCCG AAGCCCAAGC CCGGCTTGTC
  51  CGCACCTGGG CACGGGACCA CCTGGCCGCC GCCGGCATCG TCGCGGACAT
 101  CGCCATTCAC GAGCCGAGCC GCGAAGGCGA CGACCGCAAC ACCCATGCCC
 151  ACATCATGAC CACCCTGCGG CGTTTCGACG GGCAACCGT GGACGGATGG
 201  GCGAAGGGTG CCGCCCGCGA CCTGAACGAC AAGGCGTTCC TCGAGAACCT
 251  GCGGGCATCG TGGGAGACCG CCCAGAACGC CGCACTGGAG CCGCCGGGT
 301  CAACCGCACG GGTTGACCAC CGCACCCTTG CCGCACAGCA TGAGGACGCC
 351  TTGGCCGCAG GTGATGACTT ACTGGCCGCC GTCCTCAACC GCCCCCCGGA
 401  ACCTCACCTG GGCGTGTCGG CCCAAGCGAT TGACCGCCGG GCCGGGCGTC
 451  CGGTCAGCAA CCGGGGCCGG GCCTTGGCGG AGGTCAGGGA GACCCGCACC
 501  CGGCTCATGA CGGCATACGA CACGGCACGG AGGGCCGCCG TGTTCATCGC
 551  AACGACCACC GCCGGGCTTG TTGACCGGGT GTCCGGTGCC CGGTCAGAGA
 601  CCGGACACCC CATTGCCCGA ATGTTCGGCC TTGGCCGTCA TGCGGCAACT
 651  GTTGCCGACA CCGTGCCAGA ACCGTCCCGC CCATCGCCGG ACGACGATAC
 701  CCCGTCCCCG TCCTGACCCG CCTCAAACCG TGCCGATGCA GCGGCCTCTT
 751  TAAGCCCACT CTGTGCCTCT TCGGCGGCCC TGTGCTGTCT GGCCATCCAG
 801  AAATCCAGAA TGGCCGCACC ACGCATGGCT TCGGCCTCGG CGTCCCGTGC
 851  CTCGTCCAGA CCTGCCCGGA CCACCACCGC CTCAGCGGTT CCGTGCATGT
 901  CCAGATGTGC GGCCACCATG TCCAACACGG CGGCCCTGAC TTCCTCGGGC
 951  GACACCTCGG CCCCCATCCA ATCGTGGCCG AACTTCTCGG CCACGATGCG
1001  TGACACCGCC GCCTTGCAGA AGGTCCGGGC ATACTGCTCC AGACCGTATG
1051  CAGCCTTGTC CTCGACCGTC CGAGCGTCAG GCGCCTTGAT GACCCTCTGA
1101  ACTGCCATTG ATGCCCCTTT CTCGACTTCG ATTAGTGCCG CAATTTGCTC
1151  GACCATGCTA CGAACCCAAT GGACGGTCCC CAGCAGACGC CACGCCCCAT
1201  TCCGTGCCAG ACCTGCGGCC CCGGCCTTCT TGTCCGATTT GGGCGAAAAC
1251  CGGAACTCAA CCCGCACAAG ATGCGGGTCC GCGTCCTCGA TGGCCAACTT
1301  GCCGTCCGCC ACCCGTTCAA GGTCTTTCTG ATAAACCTTC ACGGACGCCT
1351  CACCCTTGCC CCAATAGAAG GTCCGGCCCG TGTCGCTCTC GATGACACGC
```

FIGURE 4A

```
1401  GGGGCCGCCA TCTTGGACGC CTTGGACATG CGGCGGGCAT AGTCCAGCAA
1451  GGCGTCCATC AAACCCTCTT GGCTATGGTC CATCGACACG TCAGCACGAG
1501  CCAGCAGGGA GGGACCAAAG GCGTTCAGGG CCTGCGGGGC AGCAGCGCA
1551  CAACGACCAT CACCACCGGG TATTTCAAGG CTCGGCATGT TTCTGGCATG
1601  CCCTGCCCGC ACCGTAGCCC GGCGTTCCTC ATCAATGGGT GAGTCCGCGT
1651  AATGCAAGGC ACCCGCGAAA CCGTCCGTCC CGTTGCCCAC GCGTTGAGTG
1701  TGCAGACCAG CCAGCACAGA CCAGAGACAA AAGGCATCCC GTGCCTCTCT
1751  TGCCTCTTCC TCGCCCATCC TGTCCTCGTA GTGAATGACA CGCATGGCCT
1801  CAACGCGTTC AGTGCCCGTT AAGCGGGCAG CCTCGGCAAC CTCCGACGGG
1851  TCAGCCCTGC GGCGTTCGCC CTTGCCGTTC CGCCCGTTAG GCAACGTGAT
1901  TGTGAGCCAG TCGAAAAACC ACGCCGTTTG CAGCCATTTT TCCATGACCG
1951  GGCTGGTTTT CTTGCCCTTC CTTCGCTTCT CCGAAGGTGG GGGGCACTTT
2001  GGGGCACAAA CCGCCGGTTT TACGCCGTTC GGGGCCTGCT TTTCACATTG
2051  AAAATCAGGT GTTTGCCCCG AACTACCCCC CCTGTTAGCA TGTGGGGGGT
2101  TTTGGGCCTT GCGGCGGACC TCATCGAGAG CCGCGACCGC CTGCTGTGAA
2151  AGGGTTTTAC CGCCGTGGAC CATCATCGCG TCTCCCGTTG AGGGTGGACG
2201  CGGTCTCAAG CATGTTGATT CTTGCGAATG ACATGGCTAT ATCTCTCCAA
2251  AGTTCTGAGG ACGACGCGGG GACCGCGAAA TCACAGCGTT CGTCCAGGTT
2301  AAGGGCTCCG GTTAATCCCG GAGCCTTTCC ATTTCATATG AACGACATCC
2351  GGAAAAATCA ACATATTGAT GCCGCTGGAC GATGTGCGGC CAAGATGTGC
2401  TGCAGTATTC CCGGCGGGCG GAACCGTTCC GATATTTGAA GTCTCCACGC
2451  TTCCGCCCGC CTAATGTCGT TCTGTCGTTG AACTTTCATA AAGGTGAAAC
2501  CCTGCTGGTT TCCCCCGGCG GCGAAGCCGC CTCCCCCTTC CTGCCTCACA
2551  AAAAAAGGGA AAAGGCCCGT TCAACCGAT CGACGCAATC TCCTTTCACG
2601  GTATCCAGAT ACCTTTTCTG GTGAAGCCAT CCGAAACAAA GGCCGCGAGT
2651  CGTCACACCT GGGCTTGACC GACGCGAATC ACTCGGACAG TGTCCGGTCA
2701  TGGACCACAT GCTGACCCCA AAACAGGCGG CGGCCCGTGC GGGCTGCGGG
2751  CGTTCCTCTA TCATGAGGGC GTTAAAGTCC CAATCTTTGC CCGCTATACG
2801  CGATAATGAG AACCGCTGGC AGATTGACCC GGACGCCCTT GACCGTTGGG
2851  CCGGTCACAG GCCGGACAAT GACCGGTCTA TGACCGAACA CGGACCGGCC
```

FIGURE 4B

```
2901  ACACCTTCGG ACACCCAAAC GGACACCCCG GAGACCTTGG CACGGCTCGC
2951  CGTTGCCGAG GCCCGGTTGA GTGATGCCCT GTCCCGCGTC GAAGATTTGC
3001  AGAGAGAACG GGATGAATGG CGGGCACAGG CACAAGCCTT GACCCGTCAG
3051  CCCGGTTGGC TGGACCGCCT ACTGGGTCGA ACCTGACCCC CCATCGTCAC
3101  CTTTGGCCTC ACCAGCGGAT TGCTTGTGAA CCAAGGCCAG CAGTTCCTTG
3151  ACCTGTTCCA CGCTACCCGC TTCGGCTTCA ATATCGCCCA TCTTGACGCG
3201  GACCTTTCGG CCTTGTCTCG CAGCCACCCA TCCACCGATA GCACCAATCA
3251  CAGCCGGACC GAGGGTTGTG GCCATCATCG TGAACTCACC CAAAAAGTG
3301  ATGCCACCAG AGCCAGCCGA GTCCCTGATG AACGCTCGCT CCGAATATTT
3351  TATGTCCTGT TCTTTCAGGA TGGTGCGGAA CTCCCCGGCA TCTTCTTTCG
3401  GGAAAACCGC GATTTCTAAA TCACTCATGG AATGCTCCTT TTGCCCATGA
3451  GGTAATAATG CCCTGCCAAT GAGCACCGAG CAAATCAGCC GGGTTGCTCT
3501  TTCGAAACGG TCTCGGGCTT TGGAAGTGTC CACCCCTCGA ACAGTGCCCG
3551  GTCTCTCTCT GGCATCGAGG CAATCGCCAT CCGCAGCACC TTGACCCATT
3601  GAGGATCTTT TGCAGCTTGC CCGATAACCG CACCGCCCAG GACGATTTTC
3651  CGCCGTGCGT CCTTTTTTCG GTCCTCTGCC CGAAGTTTTG CCCCGGCTTG
3701  TCGTATCTGG GCCTCTGCCC TCGCCTTGGC CTCTTTGGCC CGCTCTAACT
3751  GCCTTTCTAC TGAAGTTCTT GCCATTTTCC GTCCTCCTTC ATAGGGCCTA
3801  TATGAACGGA GAGGGAACGA AGCAAGAAGT TCTCAAGAAC CCGAAGGGCG
3851  CACTTACACA AACTCTGGGG AGTTTGTTTC GGGCGCCCTA CCGGGGGTCA
3901  TCTCGCCGAT GGGGCGTCTC CGACGGTAAA AAGAGGAGGG GCCGCCGTGG
3951  CGATATATCA CCTGTCCGCG TCCATTATCG GGCGAAGCGA TGGCCGGTCA
4001  GCCGTTGCCG CGTCAGCATA TCGGGCCGGG GCCGACATGA CCGACCCGGA
4051  CACCGGGACG CGGCACGACT ACACCCGAAA GCGAGGCGTC CGGGCAACCT
4101  TCATGGAGTT GCCCGAAGGT GCCCCGATT GGGCCACCGA CCGCCCGAGC
4151  CTCTGGAACG CCGTCCACGC GAAGGAGACG CGGAAGAACT CGCGGCTTTC
4201  GCGTGAGATC C
```

FIGURE 4C

SEQ ID NO:5

```
   1  GGGCCTTGCA TCCGATGGCA AGCAAAAACT ACCCAGTCCG TCCGTAGGCG
  51  GGGGGTCGCC AGCCCTGTGG GTGGGCGCTT CCCCCCGGCC CGCAAGCGGG
 101  CCCGGAATGG GCATTTTTTG CCTGCCCTAA GATCATAAGA AGGGCAAAAA
 151  AAACATCGTT TCAAAACAGC GTGTTACCAC CCCCTATAG DACACCAGAG
 201  TCCGGGGTAG AGGACTCTGG TGTCCTCTTA GGCCATTTAT GTCCAAGAAT
 251  GTGACAGCCA GCCGAGCGGA GGTAGAGGAC TCTGGTGTCC TATGCTTAGG
 301  CCATTTATGT CCAAAAACTT GACAAGGGCC ACATTCCTGC AAATCTGTC
 351  CAGAATTTGG AAAAATTCGC CGGATAGTAG ACAGTGGCAA AGCCTCCCCC
 401  CATTCCCGCA AGCGCCCGC TCGGCACTTG GGTTCAAACT GACCGGGAAG
 451  CCCACGAGGC GTGGGCGATA CTGGCAAAAA AGCCTGCTGC CAGCGCTGTG
 501  ATGCACATTC TGTGCGCCAA CCTCGGTGAG CATAATGCCG TGGTCATCAG
 551  CCAGGACACC ATCGCCAAGC TGTGCGGCCT TTCCACACGG TCCGTCAGGC
 601  GCGCCATCGT CGATCTGGCC GAAGGCCGAT GGATCGAGGT TCGCCAACTT
 651  GGCGCGACCA GCCAGACCAA TGCCTATGTC GTCAACGACC GGGTGGCATG
 701  GCAGGGATCA CGGGACGGAC TGCGCTACAG CCTGTTTAGT GCGGCTATAG
 751  TCGTGTCCGA GGAGGAGCAA CCCGACCGCG CTGAACTCGA CCAGCAAGCC
 801  CCCCTGCGAC ACCTGCCACG CATCAGCGAG GGGCAGATAC CCACCGGCCC
 851  CGGCCTGCCG CCACCTTCGC AACCGTTTCT AAAAGACATG GAGCCAGACT
 901  TGCCCACCAT TGACCGGGCA ACATCACCCA ACTTTGACCA GCAGGAACAG
 951  GGGTGAAAAA GGTGGACAAA CTTTCCATAC GCGAGGCGGT AAAACACTTC
1001  GATGTTTCCC GGCCAACCCT GCAAAAAGCC CTTAAATCTG CAAGATTTC
1051  AGGTGTTCAG GATGGACAAG GAACGTGGAC AATAGACCCC TCAGAGATGG
1101  CAAGAGTTTA CCAGCCAAGG CAAGATGAGG TGGTAAAGGA TGGTGGCCAA
1151  GAACATGAAA ATTTGTCCGC CAAGAACACC CCTTTACATG GTCAAGTTGA
1201  GGTTCTGAAA GAGCGGCTTG CAGATGCTGA AAAACGGGTG GCGATAGCCG
1251  AGGCACTGGC CGAAGAACGT GGAAAACACA TCGAGGATCT ACGCCGGATG
1301  CTGCCTGCAC CGGAAGCCGG TCAGCCCCGC CGCCGCTGGT GGCCATGGTA
1351  AGGTCAGCTA TGCGGGACCA AGCCGCAGCT CGCAAGTGCG GCAACAGAAT
```

FIGURE 5A

```
1401  CAGACCCGCT TCGGACAGAG AGCTCAAGCT GGTGGAAAAC CGCCTGTGAA
1451  GCTGCT
```

FIGURE 5B

SEQ ID NO:6

```
   1 CACCATGGCG CGCTGCAGCT CTTCTTTGCT TCTGTTGGTT CTTCTCTCGT
  51 CAAGAAGCTC AGGCGGAAAC CGCACTATAA AGTGCAGAAC AGGCTTCTTC
 101 GCCGCTTTGT TTTGCCTAAC GCCTTTTGTG TGCGCGTCAT ATGCCGACCG
 151 AAGGTCTAGC GTCTTATAAA CGAGCGGAGA GGCATCTCTT ACGACGCGTT
 201 TCGCACTTGT TTTGTCTTGT CGTTTCGCGT GCTTTTCGGC TGCTGACAAT
 251 CCAGCCATAT CTAACGCACT ACATCTCACC GCTGCTTTCA TTTTCAATCC
 301 CTCATATATT ACCTTTTCTG TTGTTTTTGC GAAAAACGCA AAACTCGCTT
 351 TGCGTTTTTT GTTCGGCACC TGCGGCACCT CCAAAAAACA CGCTTGCTCT
 401 CCGAGGGTCT GGCAGGAGCC TAAGAGGGGG CATTCTGCCC CTGATCGACC
 451 CCATTGAGGC TCGATCTAAA CAGACCCCCC ACAGGGGCGT CTGTGGGCCG
 501 CTAGTGCGGC CTTCCGCCAT CTTCGAGCCA TCTGATCTCT GCAATTAGAG
 551 ATGCATGGCG CATCTCCCAT TCCAGCTCAG ATATCCCGTA TCTGTCGATG
 601 ACGGTGTCAT ACAATTCGTC GAGCCTTGCT TCGCGCTCTT CTTTTGTCAT
 651 GCCAGTTGCA TCGCGTTCTT CCATCTCCTC GTTCTCCTCT ATGATGAAAT
 701 CATTTTCGTC CTCGTCGTTT GGCCCGCTTT CTGCTGCCTT GACCGCAACA
 751 GCGCCTCCGC GCTCTGCGGC CTCGAGCAAG TTCACGCGTT TAGCGCGCAC
 801 TTGCTTCCAC CCTTCATTGT CCCACTCCGC GACAATTTCA GGGCCGCTTT
 851 GCTCTGCTGC ATCAACTTCA GCCATAGCTT CATCGTCATC CAGCTCGACC
 901 AAACCGCATT CTTCTTTCAA GCCTTGGCTC ACACCAATT GCCGCCTACG
 951 CTTGCCGCTC GTTGCATTGA ATATTCGAG CCAAAGCCCG TCATCGCCCG
1001 CCTGAAGTAG CTGCCTTGGC GTGCGTCCTT TGCGTTTTCC GCTCTTCGAG
1051 CTTGAAAGCG TCAACTCTTC GGCAGCGCCC CACTTCGCTA CGTAGTCGCC
1101 CGCATTGGCA GCCCCGCGAA CGTCAAACGC CGCATCGTTG CCCCACATGC
1151 CATACCCCTT CAGACATGCA CGCCACGCAT CGCCTAGACG TTGCATCAGA
1201 TGCAGCGCTT CGCTTTCATC GCCAGCTCTT AGCAAGACAA TTTCGTGAAA
1251 GTGCGGGTGC CACCCATTTG CATAGCTATG AGTAATTTCA GTTGATGTGA
1301 CTGACCCAAC AAATGGTAAA TCGCGCCACT CGCGGCGCTG ACGCAACCGC
1351 TGTTTCGCCT TCTTCATGTT TTGGAGAAGA TCAAAAAGCG AATCACCTGC
```

FIGURE 6A

```
1401  TTTGTGCTGG GCTGTCAGAG TTATGAGCAC CGGCACAAAC CCGTTGTCGC

1451  GCGCCCACGC GAGCAAGTGA TTCATTTCAG AACGGCGAAT TTGCGCGATG

1501  CGAGCGCTAC AAACTGCGCA GCCCCACACA TTCCGGCACT GTGCTAGACC

1551  TGAAAAGAAT GCCCGACGCC CGCCATCCTC GCCCACGTTT GCACGTTTA

1601  GCTCAACTGT CGGAGACACT TTTACGTGCC GACATTTCGC AACTTGGTGG

1651  GGCTTGTTTT TGTTCAGATT CAACAGAATC CGAGCGGCTG AACGCAGATC

1701  TGCATAAAGC TGCCGCCTAC TGAATAACCT GTTGTTTTCT TTGTTTTTTT

1751  CATTCGGTTG ACCCCATTC TGGTCAACCG ATTTACGGTA TATACCAAGG

1801  GGGGTCTGCC GACCCCTGA AAAAGCGTCA TCGCCGCGCG CCTGCGCACC

1851  CGCGTTCTTC TTCGATTTCT GAACTGAATG TGATGCTAGT TTGTGAGACA

1901  TGGCCGCAAA CCCCGACGGG TGCGGCGACT ATTCTCTTGA TTTTCTGCGT

1951  CTGTGCGCAT ACTATCCTCC GTGTTCATCA GGCTCACGCC TGATCTGATT

2001  AGGGCTCTTG TCTCTGCTTG TATCGTCGCC AAACTATACT TTAAGCAGCG

2051  TCTAGAGCCT GATGAACGAT CTAAGAAGCC CGCCCCCTGA AAGGCGGGCT

2101  TTTTGATCT GTGCCAGATG TTGTTACATC GGCGCTCAAA AATCAAGTTT

2151  TTTCTTGACT TTCAATAATT TGCATTATGC ACATTATTAT CGTTTGATAA

2201  TAAGAGCCAG AACAGCACAG AATAGTTGTG CGATAGCTAT GAATAATAGC

2251  AGATCCATCC CTGTTTCCTT TCTTACTAAA TACAATGCGA AACTGCTCGC

2301  ATCTGTTTTA TTTAGTTGAA TCGGAAACTC CAAATCGGCC GGATTCAAAA

2351  AAAATATAGA CTATCTTTAA AGTAGCAACG CCGCCGCTCG CGCGACGGCA

SEQ ID No:7

```
   1 AGAGAATAAG ATCAGGTCTG TTCTCGTGCC GCCAGCGGTT AAGCAGGTTA
  51 TAGAGCCGAA ATTCACTCTT ATTCATCAAT TGCTTGCTGC TGTAGAGCGA
 101 TTTTCGCCCT TCAACGAACC AGTAGACACC CCCGACAAGG GCGATGACCA
 151 CCAGAAATCC AATTATCATT GTGAAATTAA TGTCGGTCAT GACTGCACTC
 201 CCTCAAGGCC GAAGTCAGAG ATTGCATCTT GACGCAGAGC GACGAGTTCA
 251 ACGCCGTCGA TGCGGTTTTG GGTGGCGGTA GCCGGGCTGG CGCGGATACG
 301 CCTACCGTTG GCACGGTTTC TAGGCGACAT ACTGAGGCAA ACCGGATTTC
 351 CAGTGGGCTG CGTGCTTTGT TGTAAGCGCG CCATTTCATC CCCCCGAGGG
 401 CAGGGGAACG GCTCACAACT TCCAAAGGCC CCGAAAAATT CTCGCGATGA
 451 CCCCACCACG GGATTTGTGC AACACAATCG GCGCGCGGGA CAGGCTCATA
 501 TCAACTTGGA TAAGCGCCGC GTTTTTTGCA AAATGCGAGA AAGTGCTTAT
 551 CCGCATCTTT CACGTTGATG GCCTTGTCAT GCACCCAAGA ACGCCACTCT
 601 TCTTCAAGGG AGTAAACATC CCACCCAGGA GCAAGTTCAC GGGCAGTATC
 651 GCGTGTGTCG GGATCGTTGA ACGGCAAGGC CTGAAAAGTG GTTGATGCTA
 701 TAGTTTCCAC CACCTTGGGT CGGAAGACAG CGTTCTCTCC TTCGATACTC
 751 ATGCTGTAGT CAGGGAAGTG GTCGTGCGCG GTGTCATCCT CAATGATCTT
 801 CGAAAGCAGG CGACGGAACT CTTTTTTAGT TGAGCCGGAA CCGCACTTGT
 851 TTCGCAAGAG CTCCAAGCTA CACATCCATT TTGACTGCGC GCCACAATGC
 901 TTTCGCCCTA TCTCATACAA CCGCCTTTCG AGGGCTTTC TGAGCAGGAA
 951 ATACCCCCGG CTTAGAGTGA GGACATGGTT GTTCTCGATC GCATCAAAGA
1001 CCCAGTCAGA GAGCGTTATT TCGACATCAA GCATTCGGCC GTCGCGGGTT
1051 ACGCGCACGA TCTCGGCTGA TTCAATCAGG CCAAATACCT TGAAGTATTC
1101 TTTCCCACCT TGACGAATAT TCGTTTCAAT TTGGGTTCCC TGCAGCCGCC
1151 GAAGGGCATC TTTGAGCAGC TGATAACCCT GACCGGATGT CTGACGGTTC
1201 GTTGCCACAA GCAGATCATA AGCCTTGAAA CGCATCGATC TACTTATTTT
1251 CTGCCCCTCA TTAATGGCCG CCATGCACTG GCTGATGCAG TAGATCAGCA
1301 CATCACGGTC ATGAACGGTA GCAAGGCCAT AGCGTGAAGG GGAAACCTCG
1351 ATCCAATTGT CGTTGTTCTG ATAGCGGCGT GGCTTCATGT CCGGCTTTGT
1401 AGACAGGGTG AACATAGGGT GCTCCATCGA AGCCATATCC CCCTTGGGAA
```

FIGURE 7A

```
1451  CCGCATCAAC GATGTCGCAA ACGAAAAGGT CTTTTTGTGG ATGACGATCC

1501  GGCAAAAGCG GTGATCGTAG GTTCGTCATT TCACACACTC CCGCGCCAAG

1551  TAAAAATTCG TCATTTCACA CACCGTACAA GACTATCGTC ATTTCACACA

1601  CCACTCGTCA AGGCTCGTCA TTTCACACAC CCAAGGAGGC TGTGGATAAC

1651  TCGAGCCGCT ATCGTCATTT CACACACCAT CTTTCGTCAT TTCACACACC

1701  ATCTTTCGTC ATTTCACACA CCAGGTGTTA TTTTTTTTAT AGTTATATCA

1751  ATTGATTACG AGCTGTTTTC GGAGCTGTAA CTCTATTCTA ACTCTATTCT

1801  AACTCTCATA GCTTGCCAAA ATGGCACCTC ATATCCCGGA TATCCGGTTT

1851  CATTATGAAA CCAATCAACA ACATTTACGG TGTTTTTTGA GGAGCAACAC

1901  TGTCCCAACG CAGGTTCAAA CCGATCACGC CGAATCTGCA AAGAAAGGGG

1951  CAGTGCTATG TTCATTTGGT CACTCGAGGA TCACCCGAAC CACAGGTAAG

2001  CCCTCACATG CTATGTTGAT ACCTCCAGG
```

FIGURE 7B

```
SEQ ID NO:8

1  MHILCANLGE HNAVVISQDT IAKLCGLSTR SVRRAIVDLA EGRWIEVRQL

51  GATSQTNAYV VNDRVAWQGS RDGLRYSLFS AAIVVSEEEQ PDRAELDQQA

101  PLRHLPRISE GQIPTGPGLP PPSQPFLKDM EPDLPTIDRA TSPNFDQQEQ

SEQ ID NO:9

```
  1   MSHKLASHSV QKSKKNAGAQ ARGDDAFSGG RQTPLGIYRK SVDQNGGQPN
 51   EKNKENNRLF SRRQLYADLR SAARILLNLN KNKPHQVAKC RHVKVSPTVE
101   LNVQNVGEDG GRRAFFSGLA QCRNVWGCAV CSARIAQIRR SEMNHLLAWA
151   RDNGFVPVLI TLTAQHKAGD SLFDLLQNMK KAKQRLRQRR EWRDLPFVGS
201   VTSTEITHSY ANGWHPHFHE IVLLRAGDES EALHLMQRLG DAWRACLKGY
251   GMWGNDAAFD VRGAANAGDY VAKWGAAEEL TLSSSKSGKR KGRTPRQLLQ
301   AGDDGLWLEY FNATSGKRRR QLVWSQGLKE ECGLVELDDD EAMAEVDAAE
351   QSGPEIVAEW DNEGWKQVRA KRVNLLEAAE RGGAVAVKAA ESGPNDEDEN
401   DFIIEENEEM EERDATGMTK EEREARLDEL YDTVIDRYGI SELEWEMRHA
451   SLIAEIRWLE DGGRPH*
```

FIGURE 9

SEQ ID NO:10

```
  1  MTNLRSPLLP  DRHPQKDLFV  CDIVDAVPKG  DMASMEHPMF  TLSTKPDMKP
 51  RRYQNNDNWI  EVSPSRYGLA  TVHDRDVLIY  CISQCMAAIN  EGQKISRSMR
101  FKAYDLLVAT  NRQTSGQGYQ  LLKDALRRLQ  GTQIETNIRQ  GGKEYFKVFG
151  LIESAEIVRV  TRDGRMLDVE  ITLSDWVFDA  IENNHVLTLS  RGYFLLRKPL
201  ERRLYEIGRK  HCGAQSKWMC  SLELLRNKCG  SGSTKKEFRR  LLSKIIEDDT
251  AHDHFPDYSM  SIEGENAVFR  PKVVETIAST  TFQALPFNDP  DTRDTARELA
301  PGWDVYSLEE  EWRSWVHDKA  INVKDADKHF  LAFCKKRGAY  PS*
```

FIGURE 10

SEQUENCE LISTING

```
<160> NUMBER OF SEQ ID NOS: 10

<210> SEQ ID NO 1
<211> LENGTH: 7029
<212> TYPE: DNA
<213> ORGANISM: Ketogulonigenium
<220> FEATURE:
<221> NAME/KEY: misc_feature
<223> OTHER INFORMATION: pADMX6L1

<400> SEQUENCE: 1
gccatttctg cgctgcactt cgctaagggt tcaagggaaa cgcagggttc ccttgcccac      60
acaaacgcgc agcgtttgta taagtgggca cttcgtgttt gacacgctat ccactacgcg     120
gcacaaattc aactcttgta acgaggaagg gcggtagaat ggcgcgcacc atcgaccagc     180
agatcgcaga tgcgcaagcg aagctggcgc ggctcaaaac ccgtcagaaa gccagcgaca     240
cccgccgaaa gatcatcgtc ggcgccatcg tcaccaccga ggccctgaaa gaccccaaga     300
tttccaaatg gctggcatct accctgcgca agaacgcaac ccgggacgtg gaccagaagg     360
aaatcgccgg gctgctggcc gacctcgatg ccagggcgca aagcgccggg gcgggtgagg     420
catgagcggc agcaccgatc cgtttctggt tctggtcgat gatattggcg cgctgcgccg     480
ccagatcgag aacctgcaac gcaccagcct cgacagggac gaggccgaac atctcaacgc     540
```

-continued

```
gaccatcgcc cagagcctcg acaacatggc gcaaaccgga aaacggctgg aacagcgcct    600
tgagggccag ttgcagctcg ccaccgccaa acccacagg gacgccatag aagccgctca    660
gggggccgcc agagcggcta tcagggaatc ccatgccgag atcctccaaa cggccaggag    720
cctctcacag gccgcaggag aggcccgcag agaggcgtgg cgctggttcg gcgggttctg    780
ggtctggctg gcctcgatcg gggccgcagg ggcgcttgtc ggcgcgctgg ccgtgttctg    840
gctccagggc cgcgccgatg ccaaagcctt cggacagtat cccagcatct actgcaccac    900
cgcaggcggg gcattcgccg atcagcgcga cggaagccga tactgcatct tcatgatttc    960
accgccgaca cagccagacg gggaatgacg gcttacgcgc cgggctggat cgagactttc   1020
agcccgagcg ccttagcgac cttcatcacc gtggacagcg tagggttccc atccccggat   1080
agcgccttgt tcagccccac ccggctcatg ccaacctcac gggccagcgc ggtcatgttc   1140
cgtgcgcggg caaccactcc aagggcgcgg caacatagg cgggatcgtc gccgccatct   1200
tccatgaccg cttcgagata ggccgcaata tcttcctcgg tcttgaggta gtcggcggaa   1260
tcgtagcggg cgaattttc ttccggcatc gcttagccct ccactctgc ggccagcacc    1320
ttggcctgtt tgatgtcttt gctctgcgtg gacttgtcgc cgccacaaag caggatcacg   1380
agaaccggcc cgcgctggat gaaatacacc cggtagcccg gccgtagtt gatccgcagt    1440
tccgaaacac cctctccgac cggctccaca tcgccggggt tccccgccgc aaggcggtcc   1500
agtctggcag tgatgcgcgc aaccgccctg cgatcccgca aaccgaaaag ccaggtatcg   1560
aaggttccgc ttcggattaa ctcgatcatt cgacaactat agttatcatg tgggtgtctg   1620
acaaccagag ttatcacttc cttgttctaa gcaaatccga ggccagccac gggcgtagcc   1680
ggagcatcat ccctccccg cacccccacc cgtcacgcgc acacatgcgc ggaatcgtcc    1740
actcggccca aaggggcct tgcatccgat ggcaagcaaa aactacccag tccgtccgta    1800
ggcgggggt cgccagccct gtgggtgggc gcttccccc ggcccgcaag cgggcccgga     1860
atgggcattt tttgcctgcc ctaagatcat aagaagggca aaaaaacat cgtttcaaaa    1920
cagcgtgtta ccacccccct ataggacacc agagtccggg gtagaggact ctggtgtcct   1980
cttaggccat ttatgtccaa gaatgtgaca gccagccgag cggaggtaga ggactctggt   2040
gtcctatgct taggccattt atgtccaaaa acttgacaag gcccacattc ctgccaaatc   2100
tgtccagaat ttggaaaaat cgccggata gtagacagtg caaagcctc cccccattcc     2160
cgcaaagcgc ccgctcggca cttgggttca aactgaccgg gaagcccacg aggcgtgggc   2220
gatactggca aaaagcctg ctgccagcgc tgtgatgcac attctgtgcg ccaacctcgg    2280
tgagcataat gccgtggtca tcagccagga caccatcgcc aagctgtgcg gccttccac    2340
acggtccgtc aggcgcgcca tcgtcgatct ggccgaaggc cgatggatcg aggttcgcca   2400
acttggcgcg accagccaga ccaatgccta tgtcgtcaac gaccgggtgg catggcaggg   2460
atcacgggac ggactgcgct acagcctgtt tagtgcggct atagtcgtgt ccgaggagga   2520
gcaacccgac cgcgctgaac tcgaccagca agcccccctg cgacacctgc cacgcatcag   2580
cgaggggcag atacccaccg gccccggcct gccgccacct tcgcaaccgt ttctaaaaga   2640
catggagcca gacttgccca ccattgaccg ggcaacatca cccaactttg accagcagga   2700
acagggtga aaaggtgga caaactttcc atacgcgagg cggtaaaaca cttcgatgtt     2760
tcccggccaa ccctgcaaaa agcccttaaa tctggcaaga tttcaggtgt tcaggatgga   2820
caaggaacgt ggacaataga cccctcagag atggcaagag tttaccagcc aaggcaagat   2880
```

-continued

```
gaggtggtaa aggatggtgg ccaagaacat gaaaatttgt ccgccaagaa cacccctta    2940
catggtcaag ttgaggttct gaaagagcgg cttgcagatg ctgaaaaacg ggtggcgata    3000
gccgaggcac tggccgaaga acgtggaaaa cacatcgagg atctacgccg gatgctgcct    3060
gcaccggaag ccggtcagcc ccgccgccgc tggtggccat ggtaaggtca gctatgcggg    3120
accaagccgc agctcgcaag tgcggcaaca gaatcagacc cgcttcggac agagagctca    3180
agctggtgga aaaccgcctg tgaagctgct gggtggcagc cgctttactc agcgaagcag    3240
ccattcgggc ggatcgcagc gagattgccc catccagtcc taagggccgt gtaaacagca    3300
cttagtgcag cagcatcgca ggcgcggaaa tctgcctgcc cttcctcgcc acctctgagg    3360
cgtcagcgat ctgccccaaa cctgcctgcc actttggcgc agcatgttgc ttgagaacac    3420
ggagctgccg atctctgcgc taagcagaat ttcctgataa tacgcacaga tgcaaataat    3480
attgcggcat caatgcgttt ccgtttaccc ctaggcagtt gcctcatcat gctgtcgttc    3540
gctgtccaag ccgcaacgac ctgcgaccga accttcactg catcttactt tcggcccctg    3600
cgttcgcccg tgaccgcagc gcggcccaaa gcgcgaccgc cgccaaggcg ggtaggaaca    3660
gccccattgc catcgggaac gggctgtcgg tcccggccaa ggccacgcag gtcgaaatcg    3720
tgaaggccat cccgaactgc accgcaccca agagtgccga tccagttccg gcggcctcgg    3780
tcgcggcggc catggcaagc gaggtcgcat tggccgaaag cagcccgacc atgccgatcg    3840
cgatccagag cggaatgata acatccata ccgaacccgt ggcagaggcc aggacggctg     3900
ccagcgccg aagaccatag aacggcagtc cccggttcag catgtcccgg ggcgtaaagc     3960
ggtccaggag gcggctgttg atctgcgcga agacaaacag cgcggctgcg atgagcgcaa    4020
atatcaaccc gtagttgagt gcgctcatac cgaagaagcc ctggaacacc ccggacgatc    4080
cggtgatgaa ggcgaacatc ccgccctgga ccaaccctgc caccagcacg ggggcaaggt    4140
aggcgggctg tctgacaagc cgcaggccgt tccttgtcgc gcttcggaag ggctgcgcga    4200
cacggcgctc tggcgacagc gtctcgggca ccaccagttt cgacaggatg agggcaggca    4260
gaccgaccag caccattgtc acgaagatcg accgccagcc gaaggcctcg agcagcaggc    4320
tgccaagtgt cggcgcgatg accggaccta tggtcatcag catcaccagc aaggtcatca    4380
ccttggccgc cttttgcccc gagtagagat cggcgacgat ggccctgctg acgaccatcc    4440
ccacgcaggc cccgatcgcc tgcaaaaagc gcagcgcgtt gaagacaacg atattgtcga    4500
ccagcggcag cgcaattgat gtgacggtga agatgaagac gccgatcaga agcggccgct    4560
tgcgcccgta tccatcggtc agcggcccga cgatcagctg cccgaggcaa aggcccagaa    4620
agaacagcga cagtgaaagc tcggtcgccg catggctggt attcagatcc tcggcgagaa    4680
tgccgatggc cgagagatac atgtcggtcg ccagtggcgg aaagatcgac aaaagggcga    4740
gcacggcgat caaggcaccg gctcgggcag ggatgagggg gcggtccagc atgatatcct    4800
cttggcggga tggtgcgatt ccatttgtag atcgcagtct actaatgtaa aattatactc    4860
aagtctataa ttcaagtcgc ttggccggaa tcgcaggaga agacaggaat gcaggaggta    4920
cggagcggac cggacggcc aaaagacccc gtggttgccg aagcgatccg caaggcggcc    4980
ctgcggctgg tgcgcgaaag gggataccgg aacgtaagca tcggcgcgat cgcgcaagcc    5040
gctggagtgg cgcggcaaac gctttacaat cgctggcacg cgaaggccga cctcatcctt    5100
gatgccgttt tcgaagagac cgggcggcgc gccgacgatc aattaccgct ggaaacaggg    5160
gacgcgtccc gtgatcggct ggaacggctt cttataggtg tgttcaatca cctccgggcg    5220
gatggcgata cactgcgcgc attgatcgcc gccgcgcagg aggacagcga gtttcgtgag    5280
```

-continued

```
gccttccggg aacggttcgt cgcaccgcgg gaaaccatcg tcaccgacat tctggccgaa    5340
gccctgcgcc gtggcgagct ttcccgggaa gccgacccgg ataccttgtc gaccatgatc    5400
cacggcgcat tctggtatcg cctcctgaac ggacgcgagc tcgatcatga actcgcccga    5460
tcaatagcgc ggagcgtgtt tccctgagcc aagacgaaac ggaaacggac ccaaatcatc    5520
ggaatgtata aagtcgcgca tcgttaccat cctgaggggg tgatcgctgc ggagcgagac    5580
gaatggcagc taccgggaat gcggccacgc cgcattggtc gaggtcggcc agggcaaagg    5640
gctggccttc acctatacaa gcgacaggcc tgccatgcgg cgccctgccc aagtgtcagc    5700
gatgggctca aaccgtcgat aggccagccc cggcccgctc gttccatcgc gggctgtagg    5760 gtcgggctg gccggatcag tgagtaagcc cgccatcccg tcgtggtca cgggcttctc    5820 gctcccgcaa ccgttcctgc tgccgctctt gctccttcag gcgttcggcc tcctgcaccc    5880
gctggcgttc ctcggcctcc cggctttcct gcaaccgcgc tgccgcctcg gccagcgtgc    5940
cccggtcgat cccctgcgcc gcctcccgta gccgctcggc caggctgcgg gaggattccg    6000
gttccggggt ttgtccaggt gcagctatgg catcggacgc ggtgcggctc tggcgggcct    6060
cccatgcctc gcgcaaccgc gcggccaggt cctgcctccc ctcccggcca tcccgatccg    6120
cagcgccggc ataagccaga ccctgcgccg cccctcttg cgtcaacggc ccgaggcgat    6180
ccacagctcg cccgatccag tcgcgcacct gaccggccag aacctccgcc acacgcgcaa    6240
cctcggccgc ctgcgccttg acctcgcgcc acacccggac ggccccgacc tcgataccgc    6300
gttccttcat ctgccacgcc ccggcagaca gttgcggcaa cggatcccgg tccagttcca    6360
ccgcccgcac cgtttgacgc agcgcctcgg cctcgtcgcc gcgatcatgc gccgcgctgg    6420
cccgctcctg cgcctcgatc cgctgcgcct ctagcgtccg gtggtcgatc cgttcctcat    6480
ggccgcatcg ctcaagggcg cggttgctgt cccgcgccca tgcctcacgc catccttcca    6540
gcatctcgac gcgttccag tcccggttct tcgccccgaa cccctcgggg ccgatttcgc    6600
gggtggtcag caggatatgg gcatggtggt tgcgatcatc gccggtccgt cccggcgcat    6660
gaagggcaat gtcggccacc atgccacggg ccacgaactc gcgctggcag aattcgcgca    6720
ccagctccac gcgctgtccg tggtccagct cggcgggcag agccacccgg atttcgcggg    6780
cgacctgcga attcttccgg gtctctgccg cctcgaccgc gttccacagc gcctcccggt    6840
cctgcaccca tgcgggggcg ttggcagggg cgagggtttc gacgtgatcg acaccgccac    6900
gcgcacggta atcgaaggtc agcccggtgc ggtgatcctc gatccgttcg cccacgcggt    6960
aggccgcagc cgccgtggcg ctacgaccgg aagagcgaga tatcatcgtg gcccgaaggt    7020
gatagatcg                                                            7029
```

<210> SEQ ID NO 2
<211> LENGTH: 4005
<212> TYPE: DNA
<213> ORGANISM: Ketogulonigenium
<220> FEATURE:
<221> NAME/KEY: misc_feature
<223> OTHER INFORMATION: pADMX6L2

<400> SEQUENCE: 2

```
gcgtctgtgc gcatactatc ctccgtgttc atcaggctca cgcctgatct gattagggct      60
cttgtctctg cttgtatcgt cgccaaacta tactttaagc agcgtctaga gcctgatgaa     120
cgatctaaga agcccgcccc ctgaaaggcg ggcttttttg atctgtgcca gatgttgtta     180
catcggcgct caaaaatcaa gttttttctt gactttcaat aatttgcatt atgcacatta     240
```

```
ttatcgtttg ataataagag ccagaacagc acagaatagt tgtgcgatag ctatgaataa    300
tagcagatcc atccctgttt cctttcttac taaatacaat gcgaaactgc tcgcatctgt    360
tttatttagt tgaatcggaa actccaaatc ggccggattc aaaaaaaata tagactatct    420
ttaaagtagc aacgccgccg ctcgcgcgac ggcattgcgg gaaatgcgat agcaacaaaa    480
ccacttattg tcgtatatcc ccactttcaa gcgaagcgcc ccgcgaagcg atcaaaaaag    540
aaagaaagaa gggggcgctg cccccgtcat gcgcaagcgc atgactcccc cgcccctcac    600
tcaccaaagc agcagctacg aagcaggacg ggatcggcgc ttgtgcatca cgtgctcgca    660
tcaccaacac aaatagacgt atccccatga atggggcccc acgtcgattt tgttggcgc    720
tactgcgcgc gcaatgccct gcagcctcac ccgaccggct ccgaagcagc agcttttaag    780
acagtgagtg acacaagaaa acatgcgcaa gcgcatgtgt gcatcgcgtg cgcgcgatgc    840
acggaaggt tgccttcgtt gtatataata atatagcctg cacgctgtgc gcacagcgtg    900
catgagaggc aaaaacatgt caaaaatgtt gactactgca caagttgcac agcgctttgg    960
actgtcacga tcgacagtta gcagagcgct taaaaacggc gacttgcgtg catccgcga    1020
caatagaggc gtgtggaaaa ttgccgaaga tgatgcgcat aaatggcgca gcgacgccgt    1080
gcatgaacag cgtgcgcaca gcgtgcatga cagtgcatta cgcacacgtg ctgaagttgc    1140
ggaagctcgt gcaacagcgc tagaaatgca cgtgtctgac ttgcaaagcg agcgtgacga    1200
cttgcgaaag cagcgcgacg agctgcaagc gaagttagac ggtcggcccg tcgaaactgt    1260
cagtatcagc cagcttttcg ggcgccttt tcggcgctga catggcgcgt agaagcgcga    1320
cagtctcagc tttcgttcgc ttcatctgcg gcatgatctt cacagcatca gtgcgtgctg    1380
cgcgtgtctc ttcgacctct tttctagagc cgagccgcaa tgcaatctga atagatctgc    1440
gtattcgcgg caagctttta cgcacttctg aaatcgcttc atcgagcgac ttcaagcgct    1500
ctacaagaat gccgcgcaag ccagaaactc gcttgcgctc agccctgacg gcttcgacag    1560
cgacagactt tgacgctca aaatcgactt gtgcagcatc gagctttgca cgctctgcat    1620
cgagctgctc gcgttgtgtt ttaagctctg tgcgctctgt ctcgacagct taaaagcct    1680
cagtttctaa gcgatccggc gcgccgtccg acttctcacg cttaggctct agcttgatgt    1740
tattccgacg ctcgaaaaac gcagcaaact cgctttgcag cgcaataccg accgcgcgcg    1800
gcgcgctata gtttggcgct gccccagaat gccgccgctg gatctcttcg cgatgtttat    1860
cggccagctc gcgaccaaat tttgtggcgc tcgaccacat ttcgccaggc tgatccggcg    1920
gcgttctttt cgtgcgcttt tcataaactg gcgaagcaaa acatcgacg atgctctcgc    1980
ccgcctcgtc tctgtctagc ctcgctgcaa agacagcgtt accgccgtgc gtttcgttta    2040
taaactccac tgcttggcgc accatggcgc gctgcagctc ttctttgctt ctgttggttc    2100
ttctctcgtc aagaagctca ggcggaaacc gcactataaa gtgcagaaca ggcttcttcg    2160
ccgctttgtt ttgcctaacg ccttttgtgt gcgcgtcata tgccgaccga aggtctagcg    2220
tcttataaac gagcggagag gcatctctta cgacgcgttt cgcacttgtt ttgtcttgtc    2280
gtttcgcgtg ctttcggct gctgacaatc cagccatatc taacgcacta catctcaccg    2340
ctgctttcat tttcaatccc tcatatatta cctttttctgt tgtttttgcg aaaaacgcaa    2400
aactcgcttt gcgtttttg ttcggcacct gcggcacctc caaaaaacac gcttgctctc    2460
cgagggtctg gcaggagcct aagagggggc attctgcccc tgatcgaccc cattgaggct    2520
cgatctaaac agaccccca caggggcgtc tgtgggccgc tagtgcggcc ttccgccatc    2580
```

```
ttcgagccat ctgatctctg caattagaga tgcatggcgc atctcccatt ccagctcaga      2640
tatcccgtat ctgtcgatga cggtgtcata caattcgtcg agccttgctt cgcgctcttc      2700
ttttgtcatg ccagttgcat cgcgttcttc catctcctcg ttctcctcta tgatgaaatc      2760
attttcgtcc tcgtcgtttg gcccgctttc tgctgccttg accgcaacag cgcctccgcg      2820
ctctgcggcc tcgagcaagt tcacgcgttt agcgcgcact tgcttccacc cttcattgtc      2880
ccactccgcg acaatttcag ggccgctttg ctctgctgca tcaacttcag ccatagcttc      2940
atcgtcatcc agctcgacca aaccgcattc ttctttcaag ccttggctcc acaccaattg      3000
ccgcctacgc ttgccgctcg ttgcattgaa atattcgagc aaagcccgt catcgcccgc       3060 ctgaagtagc tgccttggcg tgcgtccttt gcgttttccg ctcttcgagc ttgaaagcgt      3120
caactcttcg gcagcgcccc acttcgctac gtagtcgccc gcattggcag ccccgcgaac      3180
gtcaaacgcc gcatcgttgc cccacatgcc ataccccttc agacatgcac gccacgcatc      3240
gcctagacgt tgcatcagat gcagcgcttc gctttcatcg ccagctctta gcaagacaat      3300
ttcgtgaaag tgcgggtgcc acccatttgc atagctatga gtaatttcag ttgatgtgac      3360
tgacccaaca aatggtaaat cgcgccactc gcggcgctga cgcaaccgct gtttcgcctt      3420
cttcatgttt tggagaagat caaaaagcga atcacctgct ttgtgctggg ctgtcagagt      3480
tatgagcacc ggcacaaacc cgttgtcgcg cgcccacgcg agcaagtgat tcatttcaga      3540
acggcgaatt tgcgcgatgc gagcgctaca aactgcgcag ccccacacat tccggcactg      3600
tgctagacct gaaaagaatg cccgacgccc gccatcctcg cccacgtttt gcacgtttag      3660
ctcaactgtc ggagacactt ttacgtgccg acatttcgca acttggtggg gcttgttttt      3720
gttcagattc aacagaatcc gagcggctga acgcagatct gcataaagct gccgcctact      3780
gaataacctg ttgttttctt tgttttttc attcggttga cccccattct ggtcaaccga      3840
tttacggtat ataccaaggg gggtctgccg acccctgaa aaagcgtcat cgccgcgcgc      3900
ctgcgcaccc gcgttcttct tcgatttctg aactgaatgt gatgctagtt tgtgagacat      3960
ggccgcaaac cccgacgggt gcggcgacta ttctcttgat tttct                    4005

<210> SEQ ID NO 3
<211> LENGTH: 19695
<212> TYPE: DNA
<213> ORGANISM: Ketogulonigenium
<220> FEATURE:
<221> NAME/KEY: misc_feature
<223> OTHER INFORMATION: pADMX6L3

<400> SEQUENCE: 3
cactttcgcc acaagatcag gcgcatgatc tttctcagcg ttcaacacac atttgagctc        60
ctgcgcctga tcgtcagtaa ggtaatatcg ttcttgcatc aatttctcct tagttggatt       120
ggttgcactg gatcttttgcc ctgacagcct catgcctcga ggcctcggcg atgtcgtggt      180
gcattgtatt ctcgcggcac tgcatcgact tcttctcggt ttccttttgt tcgcactggg       240
tacatggatg tcgttgctgg tcacacacac cagagcacac ctacagctct cccatgcgac       300
cgccttggcc gcaccgagat acatcgcctt gtgtggttcg cgacttcggc agcaatcgcc       360
gtggcagctg gattggagca tcatcaggca agggcttcgc tgcagcgtt cgtcgtgaac        420 gcctaggggc tgtaaaccta aaactgcccc cattgaccgc cgccagaaga atgatccatg       480
tctagggtgc cccatgaatt acccgcgata tccggtgtgc cgtcgcctgc aacagtaggc      540
agaccgctag caggattgat cgagtgtatg ccaccaaatg tgcccctga aatatccagg       600
```

-continued

```
gtgctcaatt catccattgt atgcgctcca gaggttggga ttgtgctaaa ggattgaaca      660
gtatggtctg gagtacccca ccagttcaga ttcaaaaaac ttcctatcat tttgaacatg      720
attggcttcc ttttcgatta agttttcaac aaacagaatt aatctacggg ccagttgtgt      780
gcagaagagc gacggcaaat tgctgttata gtatttacga aaatggtcgc caaaaaatat      840
ctgtcgatca agtgttttct gtaaccatct gaactttttg ataaatatca aggtgtgagt      900
ggtttatgcg atgctttaca tctgacatct ggtaaccgcc cctgttttct cagggtgtag      960
aatgcagatg acactgaaaa tacaatgaag tgaatgagag ccgttgccct gcccagccaa     1020
ggcgaagatt tcattatccg ctgagcaaat cttgtaccaa agagggcttg cgttcaatga     1080
gggccagtag gacttgagct ggcccttgag gcatacggcg cttttgctcc cagttgagaa     1140
gagtgcccct cgccacgccg atactacgtg caaactccgt ttgagatagg ccggtctggg     1200
cgcgaatgcg cgcgacatct atctcaggca agctgatctc atgcacagcg gcaccggcct     1260
tttgcccagt cgaaaaggcg cgagcttctt ccaagccctg catgatactg tcgaacgcgc     1320
tcattgtttg ttgctccaaa tggcgatgat ctctttgctc atttcgaccg cggccgcctg     1380
ttctgtcggg gttaggttcg cctttccgtt cttggcgaaa acggtgatca gaaatatcgg     1440
catgtggcgg ccgccaaaca cgtagatcgt tctgaacccc ccactcttgc cggcccctgc     1500
cctaggaatg cggacctttc tcaatccacc acccaaagcg atgccggcct ctggattttc     1560
tgcaatccaa gcaattgcag cgtcacgttc cgcatcggtc atgatcgatc gtgagcggcg     1620
ctggaactct ggcagttcaa ctacggtctg caggcttgtc atttaggtat acttcaatgg     1680
cgcataagtc aatggcgcac tacggcttct tgagctgctc aaggagcgca acagcgtgtt     1740
cgagggtttc accgaggccc caaccgttgg catctgctat tctgtaaaaa gattctatcg     1800
tttcaggcgt cgccttaatg ttgaactgcg cgtttcggcc agtcctacgg cgccgctgcg     1860
gcttggaaac aggggcgat ttaggctccc tgctcacgaa gccagacgcc tctgccgctt     1920
gttcagtgct gcggtcttta ggtgctatct tcggagcagg cgcgaagctg ctaagatcgt     1980
ttagtgcatc accaaaacca aggtttcgc gttgcttgct catcactgat cctcttggct     2040
acgcttcagc tttccaacca cttcgcccgc aaattgccgc gcgttctcga ttgccttatc     2100
gacgttgctg acctgcgacg gatcaaggtc agacaaggtt ccgccatagt cgaacaagtc     2160
acgataggcc gcacgctcga caatcgatgt ttcgcatata tcgatgccac cgctcatgag     2220
ctgctcgtga acgttttttca ggcgcgtga gcgaaccgcg gcacttgttc gggtcagcac     2280
aacgcagtgc ggtatggcac gccgcgccat cttcgcttgg ttgctgatca atcgaatggt     2340
ttttgcgcca cctctcgcat ccatagacga gccctgtatc gggatcagta ccaggtctga     2400
cataccgata gcgtttgcga ccatcaggct cgcagtcccc tctaagtcga cgatcacgaa     2460
ttgagacgtg ccggatgccg cctcaatctg gtcaacaatg ccgtcttctg tcacgccgct     2520
tacgatggaa ataattttcag gctttccggg taggctcgcc cattgggaga tccagcgttc     2580
tggatcggcg tcgatgattg tgacgcttgc cccgccctcc gaaagctgcg tggccaagat     2640
caaggctgat gttgtcttcc cagccccacc ctttggattg gcgaatgata tgacaggcat     2700
gtgtgatcgt ctccgcgctt ttaggtacaa tatcagatag ctaacagata tccatatata     2760
agttacagta tctagtagct atcggatatc atacaatact aaaatggtac tatttggtat     2820
catatgccaa atatcttgac ttcatgacca cttggttctg cggcaggtcc gacgaaagag     2880
cccggcgagg acgcttactt ttttctttggc tgccattttt ttgcgagctt taaaacgtta     2940
cgacggagct catcgccatc ggggatatgt gggtcgaatg gaccttctac ccattgggtg     3000
```

```
agttcctcgt gttcagggtg tgcggcgtcg ccgattgcct cgatgaagtt ttcatatccg    3060
ggcaggccgc cgacgtcctc aggcggacat ctaccgacaa catcgacaag ccgtgggtag    3120
aggttttcgg gaatcggatc gtcgacgctc tccgtctcaa tcagatgaac ccagtaatct    3180
ccgaaatcgt aaacatatcg gatcgggtcc gctacggcag tgttgatgat gtcagctagg    3240
atgtccgctt cggaggtatc ctcgtagacg cggatcagtg cgaaattggc cttgagcgcg    3300
gccttgtcct tcaacttgtc ccgttcaatc actttgcgcg cactggcgct gttttttgccg   3360 tggtggcccg gcccgtcata ttcgatgatg gcgcgcacaa agccgtcctt gctccaaatc    3420
acgaaatccg cgcgctttgc gacaaggccc cgccacagat tgccttgagc ttggatgaag    3480
gcaccgtatg gcacctgcgg cgagagaata agatcaggtc tgttctcgtg ccgccagcgg    3540
ttaagcaggt tatagagccg aaattcactc ttattcatca attgcttgct gctgtagagc    3600
gattttcgcc cttcaacgaa ccagtagaca ccccgacaa gggcgatgac caccagaaat    3660
ccaattatca ttgtgaaatt aatgtcggtc atgactgcac tccctcaagg ccgaagtcag    3720
agattgcatc ttgacgcaga gcgacgagtt caacgccgtc gatgcggttt tgggtggcgg    3780
tagccgggct ggcgcggata cgcctaccgt tggcacggtt tctaggcgac atactgaggc    3840
aaaccggatt tccagtgggc tgcgtgcttt gttgtaagcg cgccatttca tcccccgag    3900 ggcaggggaa cggctcacaa cttccaaagg ccccgaaaaa ttctcgcgat gaccccacca    3960
cgggatttgt gcaacacaat cggcgcgcgg gacaggctca tatcaacttg gataagcgcc    4020
gcgttttttg caaaatgcga gaaagtgctt atccgcatct ttcacgttga tggccttgtc    4080
atgcacccaa gaacgccact cttcttcaag ggagtaaaca tcccacccag gagcaagttc    4140
acgggcagta tcgcgtgtgt cgggatcgtt gaacggcaag gcctgaaaag tggttgatgc    4200 tatagttttcc accaccttgg gtcggaagac agcgttctct ccttcgatac tcatgctgta    4260
gtcagggaag tggtcgtgcg cggtgtcatc ctcaatgatc ttcgaaagca ggcgacggaa    4320 ctcttttta gttgagccgg aaccgcactt gtttcgcaag agctccaagc tacacatcca    4380
ttttgactgc gcgccacaat gctttcgccc tatctcatac aaccgccttt cgagggcttt   4440
tctgagcagg aaataccccc ggcttagagt gaggacatgg ttgttctcga tcgcatcaaa    4500
gacccagtca gagagcgtta tttcgacatc aagcattcgg ccgtcgcggg ttacgcgcac    4560
gatctcggct gattcaatca ggccaaatac cttgaagtat tctttcccac cttgacgaat    4620
attcgtttca atttgggttc cctgcagccg ccgaagggca tctttgagca gctgataacc    4680
ctgaccggat gtctgacggt tcgttgccac aagcagatca taagccttga aacgcatcga    4740
tctacttatt ttctgcccct cattaatggc cgccatgcac tggctgatgc agtagatcag    4800
cacatcacgg tcatgaacgg tagcaaggcc atagcgtgaa ggggaaacct cgatccaatt    4860
gtcgttgttc tgatagcggc gtggcttcat gtccggcttt gtagacaggg tgaacatagg    4920
gtgctccatc gaagccatat ccccctgggg aaccgcatca acgatgtcgc aaacgaaaag   4980
gtctttttgt ggatgacgat ccggcaaaag cggtgatcgt aggttcgtca tttcacacac    5040
tcccgcgcca agtaaaaatt cgtcatttca cacaccgtac aagactatcg tcatttcaca    5100
caccactcgt caaggctcgt catttcacac acccaaggag gctgtggata actcgagccg    5160
ctatcgtcat ttcacacacc atctttcgtc atttcacaca ccatctttcg tcatttcaca    5220
caccaggtgt tattttttttt atagttatat caattgatta cgagctgttt tcggagctgt    5280
aactctattc taactctatt ctaactctca tagcttgcca aaatggcacc tcatatcccg    5340
```

```
gatatccggt ttcattatga aaccaatcaa caacatttac ggtgtttttt gaggagcaac    5400
actgtcccaa cgcaggttca aaccgatcac gccgaatctg caaagaaagg ggcagtgcta    5460
tgttcatttg gtcactcgag gatcacccga accacaggta agccctcaca tgctatgttg    5520 ataccctccag ggaagtagca aaggtcctca cgaccaccac ctgcaggatc tccatcagcg    5580
aagacaactg tcgcattgaa cgctggcgcc ggcttgtacg tactcggtat gggtgagaag    5640
tcaggcatac ctgggagaac acgacgaagg acaccgtggt tctcgaggat cccgtagaag    5700
atatcgggcg tcccattatc cacataagcc gcaccatagc gatcctcccc gtagagatac    5760
tcacggaaag tttgcatatg ccgccagcga gagcgaaaaa ggggaacccg aatagcgaga    5820
tcctgatcgc ccaaccaaat gtcagccatg atgaacatgg aatattgatt gttccacgac    5880
gacaaagccg caaattccat gaaccgtctg accgcatgca ggtcagagcg ctttggctcc    5940
atacgatgaa gagggtttac atctcgttca acactgcgac gatccgcctt cttcaccgcg    6000
ctcacaaatg gactgcgatg taatcggccc tcaaggtagc cttcaagctg ttccgcatag    6060
gcctcatcac gcttagagac actctccaag aggcagtcag aaacgacctg acgccagtac    6120
ccattcccac gcgctgtgtc gtgacctatg acgggcctct gattgtatcg cagggagagg    6180
tgcgtaaccg gagactcgaa gctctgagac cattcccaga ggctctgagc catgggatcc    6240
cacgaaggaa ggtccgtctc tggttgctct atctcgccaa aacctaaatc ctgcagctgc    6300
acattcgcag gatagacttt gaacatcgtt cgcaccttgc cgaggtcatg aacaaagccc    6360
gcgataaaag ccgcaagatc gcccgcctct gaggggacgg ccttactgaa ctcactgttg    6420
aagaaatcta ccgcaagccc agctgtttcc agggagtgat agaatagccc accggctgtg    6480
cggtggtgat gtgtagatga agctgggagg cacagcatat agtcgtggcc tccgcgcaac    6540
atttgcctca ccaagagtgt ttctttgtga gagaggaagg ggagtttttt gagctgctcc    6600
ttgatcagct gctcatagct tccaaacgtc acatgcgggt gcaatatccg gaactgagcg    6660
ttgcgcaggt agcgcccgta agacaggatg atgcgatcgt cataaaacat tggcggtttc    6720
ctcaatcgat atttgctctt agttggtagg tgcccgtatg ggcgcggcac aggtttctca    6780
gctgtgccag gcggtcagtg cgatagcgga tccaggcgaa gttggcctcg cacagaagca    6840
gttctctacg gatggcgtct ggaaagcgcg cgaagatccg atcgctgtat ttgtactttc    6900
ctgacatgcg gatctgttcg gttggggtga acttgtcacc tcccatccgg tagcgggcct    6960
tgccttggaa tttgacccag taaatgcgcg ggcccaatgt gtcctcgcgg attcgaacga    7020
caatgcccaa attcagcgcc tcggcgcccg cgtccatttt gcgataggcc ttcagggctt    7080
cgacagcccg atcctgccaa tagcgcgccc atccttccaa gtcataaccc atcgctggaa    7140
tggatcgcaa aagctcaggc tcccaatcgg agtcgaaatc atgaaagcgc acttcgtgcg    7200
aacagctctc ttgggggtgt tcttcagaca tgctgtgctc cgaccaaatg gcgcgccgac    7260
caaaacaaga aggttgggtt caatgcccgg atgtttctgt ctgcgttcag ataaagccca    7320
tgtttcctaa tgtgacggga tggtagctcc gtcacattag ggggcgacgc attttgcgcg    7380
gcacatggcg cggagagccc gcaggcaggc ggctggacgg acgaaaatgg gcaggggccg    7440
cgctgagatc ccttgaaagc ccatgggcct aatgaatggc gctcacacag cctgtcatgc    7500
gtgtacttta cggggaggtc tcgcgatgag gtgagcgccc gcggtctctc gtcttggtcg    7560
tgtctgaccg tatgtgtccg tcgaataaac gtcatgatga ggtcctgaga taagaacgaa    7620
caggatcgtt gacggagggc atccgtctga ctgtcgtctg atgttgatgg aaagtcgccg    7680
gctctaggcg gccggtctca atttggtggt gagcagctct ttgcgctggg gggcattacg    7740
```

```
atgcagatca gccgtccagt ttaaatcggg aggggtgagg gaggtcgggg cggccgtgca   7800
caagacaatg gcatccgaaa gccggtcaat cattgggcgt atttgtccta cccatctgtg   7860
ccaattcata gcaaaaatcc cgaaccatcc gtttcgtcac acctattggc taggggagg    7920
tggggatggc cgtcaatgaa aaatatcagg gattgagttt tataattaac tgaaattgct   7980
aaatatttt ggaaggaata ttccttccgt agctcgtcta ctcatttatc ccttttcgaa    8040
aaaagactta acagcgggcc aactgtttcg catgatgcgg acaagaaaaa ttggctatca   8100
tgggagtgtt cgggtggcgc gtgggactaa gacagccaaa agcaaaaatg ctgatccaat   8160
tgtagcagaa tgcttaaaac tgattcgcga agacagtggg tatgagagag atgaattcgc   8220
cgaacttcta ggggtgcagc ataaaacgta tcgcaactac gaaggctgta tatatccgct   8280
accgttaaaa gtggtaaaga cgatacgtga gaagttgggc tatgatcttg cggatcctga   8340
tctgacttca gacgcgatca tcaccaaaat tgcagagcag cgacacgatg ttgcagccgc   8400
tcctgatctt gccgcgacag agcaagtagc gaagggcgtt agttgccctc agaggatacg   8460
tacctgcctt caagctttcc ggcaggaact cattggtgtc cagagcaagc gcaagcatga   8520
tattcgagac gcagttttg tcggagcagc tgcattgttt gctttctgct tggtggtact   8580
acgcactgaa ccgcaaaata taaggttaga gtctatctat acccttatgc tatccgtgtc   8640
cttcttggtt gcggcgtcaa ttgtcccgtt tcaggctata catatgatcc aagccgccta   8700
tcggtcgcga cgttgaccaa caatactagc cctccccgta tgcccgtctc acagggaggg   8760
ccaaagctac cttggcgaac gactgtcagt gcacgaaacg ggtgattaaa cgcaaagtgc   8820
tgactttttt tcccccgata ccgatggttc atcaaagata tatcgactga gcagatcggt   8880
gtccggggca cgcgtgtgca ttgcttctag gccagaaact gtgaagttct cttccacgtc   8940
ggattccggc acaaggaggt aatgccaggg cttctcaccg ctctttgcac cggcttgcgt   9000
cgcaatatgg caccacaggc ttgccgcatc tgctttacgc agaacctcgg tggcggtcat   9060
ttccgattgg cgttttacct cgatgatcag cttgcctgta tcggtttcga caacgaaatc   9120
gggctgatac ggcgcaccgt gattatcgaa aattttgaac tggttggggc caggtttcat   9180
ccaaaggcgg accgagctgt cttttttcaag gatgatcgcc agcttgcgtt ctggattaga   9240
gtcgaacttc gcatactgat agcagcccctt cacgaagcca gtgaagatat acttccggat   9300
ctcctgcttt tgatctggcg gtgttttgaa atcccggatg aagctcgtac cggcggtatc   9360
gaaggtctgc ggacgcagct cgccgaatgc agaggtcaga gaaacacggt agttcgtgtg   9420
ctcacgccac atattctgct ttatttgcga gaaaatgctt tcggccatcg ccttcgcatg   9480
ccccccggacg acactgcgag tttgctcatc gtcgtccgcg aagcggttgc gggtttgggt   9540
gactgcctgc ccagccagat catacaagat ggcagcatgg gcgtcatagt cgatctcagg   9600
gtagtcgatc agccgcgcga cgatgtaatt ctccagccgg tttgcggtgt ccccccttatc   9660
ctcgctggaa atacgcgatg tcttctctgt acgcagagct tggatcatga gctcattgga   9720
caacggctgg aagttccagc tcttcatgtc caggtcgaag cgcttgaagc cgaaggaaac   9780
ttgttgctgc ggagtgatcg tgagagcagg gatcgcaagg gtccgctcca cgaaattctt   9840
gcacagctcc tgagcgaccg cgacggcctt tccttcgtg atgctgggaa ggaaaccttc   9900
ttcgggtttc tgtgctgcaa tggctgcttc cgcgatgcgt tcgatcacct tggggtcgtt   9960
gagatcgcgg atcgaggaca cttccttgct gagctggggg atcacaacac tgagcaccgt  10020
gcgggcgacc ttcagctctt caggcgtgct gaagctgaaa ggcgcttggg tcggtgccgc  10080
```

-continued

```
agacgtcggc ttggcgacta gctgcacagg cgcgtccgaa gcttttcgt catccgcgac    10140 gacgactgtc ggctctgtct tggcctctgc ctgagcaagc atctggtcga ggatggaggg    10200
tgccgagacc gaaacaggct tcgagggcgg cacgtcacca ccctcaccaa tcgtcacctg    10260
cttcagcttg cgcgtgacgc cgttctcttc cttggctttc tcgatcagct cgttgaagcg    10320
ttcgtgggca atcacggtca gcgtgtcaac cacttcgacg ccggttcgct tgccataggg    10380
caggcgcaga ccgcgaccga cgtctgttc ggttaggatg tccgaggccg aggcgcgcag    10440
cggaacgatg gtgaacaggt tcgagacgtc ccagccttcc ttcagcttgt tgacgtggat    10500
gacgatgtcc gtgtcgccgg ccttctcgat attcagcaaa cgctgtgcgt tctcgtcgct    10560
ttcctcgccg gtcagcttgg agtggatctc ggccacgcgc ccttgtagc gtccgccgaa    10620 gaactcgtcc gactggacga actcattcac ctgccgggca tgggtcgtgt cctgggtaac    10680
aaccagcatg aagggccgca ccaccttcac gtcattctgg cgggcatagg tttccagcgc    10740
caccttgacg tgctcgtggt agtggatgcc gtcttccagc ttgatccgtt ccagcgtgtc    10800
ttcgtcgacg tcttcgggt tgaagttcgc gcgggtgccg acagccggtt ccttaacata    10860
gccgtcttcc atcgcgtccg gcagatcgta gcggtagacg acgttcttga agggctgcga    10920
gcgcgcgcca acggtcttcg gggtcgccgt cacctcaagg ccgaggatcg gtttcagctc    10980
ggcaatcgcc cgcgccccgg ccgaaccgcg atagcggtgc gcctcgtcca tcagcaggac    11040
caggtcatcc agttcggaga ggtaggagaa gtagctctcg ccgatatatt cctgaaggcg    11100
cttgatccgg ggggcgttgc cgccgcgtgc ttcggagttg atcttcgaga cgttgaagat    11160
gttgatgatc gcgccttctt ggccgaagag gtcggtgcca cgcacaccgc ggccttcctc    11220
gtagttctcg gcgttgacga tcagcggcgc gttatgggca aagacttcga tgccacggaa    11280
gacgtatttc gggctcgacg gctggaagtc ggacagcagc ttttcataga tcgtcaggtt    11340
cggggccaga acgaagaagt tccggctttt gccgatcatg tagaggtagc tgatgaaggc    11400
gcccatcagg cgcgtcttgc ccacgccggt cgccagcgca aagcagacgc tcgggaagtc    11460
gcgctcgaac tcctcgaagg tcgcgtcggc caggtcgcca tagacctcgc gcacggcggc    11520
gcgggccatg tcgatatcgg cttccttcgc ggggccgacg aggtcgacga tgtcatcgag    11580
ccgccgcagc gcctcggcct gcggcttgcg cagcgacagg cgttggttga tctgaaggac    11640
ggcgcgtttc gggtcggtcg tctgcatggc tcagttctcc tctgcgccaa acagatcggg    11700
tgtgtctgcg gcttttggcct tggccgattt cttcggcgcg ggggtgtctt cgatgtcgtc    11760
cggctcatcc tctgccatcg gcagggcgtt gatcttcaag gaatagtcat cctgcccca    11820 ttcgcagcgg tcaagcacca cgcgcgggat cttcttcagg gtcaggttgc tcaggctttc    11880
gccctgggcc tcataggcca tgcagcagat cagcaggctg cggtcctcgc ccacctcgtc    11940
cgagatggcg cggagctgtt cgatggtcag gctggccgtt gtcacataga tgaaggcgtt    12000
ctccgaagcc tgaccgtgca tccagtaggc ctcggttgag ggcgcgtaga catagttgaa    12060
atgcttgcac atggcctcgg ccagcatctc ggcattgtag tccttggaga tgacccagtt    12120
gccccagaca tccttctgaa gcagagatgg cgcaagacgg aagaaacggt agccgccgcc    12180
gcctctccag tttgtggcct cggtcacgcc gcccttatcg gtgccgttga tgactttttg    12240
cagccgaggc gcgacatggg ttttggcatg gtccccagc tcgaccatga tccagcggcg    12300
gcccatcttg tgggccactg cacctgtcgt gccagaacca gcgaacgagt ctatgacaag    12360
gtcgcccggt tgagttccta tctgtataat acgctccagc agttttttctg gcttcggtgt    12420 agcgaacgta gcgtctccca aaccaagaag cgtgcgcagg tcattggttg cttcacgggt    12480
```

```
tgtaccagct tcttcaccga accaaatgct ctcaggtacg cggccttctt gatcgcagag   12540
atagatcttc cgaagaacac gcgtgtcctc gtttaagaat gtaatttccc cggtctctac   12600
tttgctggca aaggtctcct ttgaccacct ccacccttc tctggcggcg gaatgatctt    12660
cccagaaggg gtagtaacat cgaacatgag attttctctg tagttcggac tacgtacatc   12720
tcctgctcgc caaggtcctt ttggatcttt gtctggatta ttatagtttt tgttgtgctc   12780
aggctttctg ggcagaaggt tgcgcgagaa cgcctctgtt ttccgatatg ctagaacgta   12840
attatgatgg agactgacgg tcttggcgtc atttttccct tgaacgctat gctgccagat   12900
gatcgagccg aagaagttcg atcggccgaa aatctcgtcg cacataacct tgaggtaatg   12960
cacttcgttg tcgtcaattg tcatccaaat ggagccgtct tcagaaagta ggttccgaag   13020
aatttctaac cgatctcgca tcattgtcag ccaaagcgag tgctccagcc cgtcatcata   13080
atgctcgaag gccgacccgg tgttataggc gggtcgatg aagatgcact taaccttgcc    13140
ccgcacggca gggtcggttt ccagcgcctt gagtgccagc aggttgtcgc cgtggatcag   13200
catgttgtcg aagatgtcgc cctcgcgccg cgtgctggcg tgatgcgaga attccggttc   13260
ttcgatcaga atgcggggct caagccgcgg gcggttgttc ttgccgatcc aggtcagttc   13320
aagtttggtt ttggcggcca tcaggcaagg gtccatctta cagtgaatag ggtcgtcatt   13380 tcggggtca ggttcagctg atctgcgatg tcatcaagca tccgctcgcg ctcagcgtcg    13440
atttcgcgca ggcgggtgta aagctggtgc tgaaggtcat ccacctgccg ctgcaaggcc   13500
ttggcctcgc gttgcagggt gaccttttct tccagcccga tcgtgcacg ggccagtttc    13560 ttcttctcgg tcgcttcctt gttcagcgcc ttgatctgct ggtcgaagga caccttggca   13620
tcctcgcgcc aggcatcgag ccgctcttcc tcctcgttga ggaaggagct gagccgatcc   13680
tgtgccatgc cgatgatcgc ggtctggcgc gcgttcaggg tttgggtcag gtcgctttcc   13740
ggcagggtgt ccgcgccaag gccctcggtc gtcgccggga catagagcat ccgagaggcc   13800
gtttccgggt cgatggctgt tccgccgtcg ctgaaggctg cgaagaccag ctcgtcatag   13860
accttggctg gggttttcag tcggaccgcg ccacgcgca tccagcccga ctgcccctg     13920 agctgggcca cgtcgcccat gttgccctga taggcgctat agtcgaggcg cagcatggca   13980
gggaccagat cgcgcgactt ggccttctgg accagctgat cggccagccc ctcgtcgcca   14040
aggcggaaga aacgccagcc gcgctcgtca gcctcgggcc attcgctgga ccaggtttcg   14100
cccccgtaat cgaagcgctg cgcatggtcg tcgtggaagc gggcctccgg cagctcggcc   14160
cgcgcgacac caaggagggc gcgcttgaag tcaccgatgg cggaatgcac ggcgtctttc   14220
cggccaagaa gccgctcgat caccttgtcg tccatctcgg ccagcagctg atctcggacg   14280
ttcttcttcg cctcgtcgat ctcgacgctg aactcttcct gaaggcggtc gaaggcggcg   14340
tcgatctggt ccgtggtgcg gcaggactgg acgatgtcga ggatgcgccg ctcgatgtcg   14400
acgccggatt caatgacgcc cagaacctcg tcggaggagc cgaacacacc ctcgaaaagc   14460
ttgaacttct gttccagaag ctggtggatg cgcgcttcag cgtggttctt ccggttcagg   14520
aagttgatga cggtcacgtc gatcttctgg ccgtagcgat ggcaccggcc aatgcgctgt   14580
tcgacccgct gcgggttcca gggcaggtcg taattgatca gcagggagca gaactggagg   14640
ttgatgccct cggcgccgga ctcggtcgcg atcagaatgg tgcgatcgtt gcggaaggca   14700
tcgacgatgg cggccttcat atcgcggtc ttggagcccg agaccacatt ggtgtcgccg    14760
tgcttgtcga gccaagcctt gtagagcgct ttgctgtctg cgtccgagtt ggagccattg   14820
```

-continued

```
aggacgacgg tctgtccctc gaagccgctt tgttcgagca gatcgcgcag ataggtttgc   14880
gtccgcacgg attccgtgaa gatcacggcc ttgcgctggc cgcccttgga gacgatctcg   14940
tcgagcacgt tcggcaggca gtccaggagc gccttgcctt ttgcgttgtc cgagatggat   15000
gcggccagat cgcggtactg ggtgagccgc ttgatttccg cttcgagctg agcgggatcg   15060
acgcgctcag catcttcggt gtcgtcttcg atcgcgtcgg cttccgaacc ggaatccgcc   15120
tcgcgccagt cctcggcttc gtcgctgaaa ccatcaaggt catcgagcgt gtctgccccg   15180
acaacacgct tcgcctcaag cctgcggatc atcttgtcga gggtctgcat cacggcgaag   15240
gaggaagatc cgaggatctt gcgcagcatg agcgtcacaa gatgacgccc gttctgcccc   15300
aaggcgatgg tgctggggtc ttggagatac tcggaaacct tttcgtagag atcggtttcc   15360
agtcgaccag gcgtgaagtc gaaggtcttg ggagacggt tggtatagtt gatcaggcca    15420
gcgcgttgga cttggcggcg cagggttcgt ttgcagatag gctcaagacg tttcgcgagc   15480
agggcctgag aggtcaggcc ttctcgtccg ccaaactcgc ttcggaaggc ttgttctgaa   15540
ccgaagtagg tttcgtcgat gatgctgatg agtccgtaca gctccatcag gttgttctga   15600
agcggagtcg ccgtcagaag gagtttctga cgcccagcca gtgcctttcg cagaaccgaa   15660
gcccgagagt tttcggcggc cttgtagacg ttacgcagct tatgagcttc gtcgaatacc   15720
acgaggctcc aaggcgtgcg tcgcagagtg tctgcaattc gtgcggcgta ctcgtaggag   15780
acgatgataa tgccttctcc gcgccctacc gggtgcggag tgccttcgtt ctcaaggtct   15840
ttgacgcgct tggcatcaag aatgaacgat ggcagcgaga attttcacg cagctcggtc    15900 gcccactgct tgcgcagaga agcagggacg atgaggagaa tgtttctctc acgttcccac   15960
cagcgctggc taatgaccag cgcagcttcg attgtcttcc ccaagcctac ttcatcggcc   16020
agaagaacgc ccttcgacaa tggtgagcgt agggcaaatg tcgcagcatc cacttggtga   16080
gggttgaggt ccaccttggc tgccgagagg gactgcgtca gagcgtcttc ttcctgaatg   16140
ccttcggatg tcaggtggtg cgcaaagaac tttgattgat attcagaaaa ctggaagagc   16200
aataggtcag gctccaaggc atattagtta agggaaggtt gttctaaatg ctgtcaagtt   16260
atggcctgcg gcttgatcgg ccagcacgaa ggactcccct ctgcccagga tattgggcct   16320
tctcgttatc acgccactga aatgtcacct gtactgcgat accatgcttg tcggctattc   16380
tggaaacttc cttccaagcc tcctgggctg attgcccttg gatagagatg ccgaggtcag   16440
ggtaatatcg gaatccttcc tcttcgtagc acgccgtctt ggtaggaatc tgtatgccct   16500
cagctaggtg atctccggat aggcccttag ccttaagaga actcactgcg ccgagaagaa   16560
ttgctgccca gtttggcttg tcgatcttct tgtgatcaac ctccgcagat aagacttttg   16620
taaatgaaag gcctggagtg gatttgaact ccatgaagct gctgatttcc gacgtgggat   16680
caatgctgat ctcgatgtca cgctctaggt caagcgctgc catcttctcc cgtaccagca   16740
gcatgatcgt ttctgatggg gtttctgtcc ccatccaagt cgagatgcac ttcagatcga   16800 caaagttgg gtcgttcagt ctgactacgg gcataggcgt catccttcta tattcatata    16860
gaatatgtta catattcaat attatggtgt caatgctagc gtttgattgg caacctgtcc   16920
taaaacggtc gttttttggc atagtgggat gaagtggtca aaatataggc cttgataatt   16980
ttgaacatgc ggctactttt ggacagggtt ttttgacacg gagggccata cattgacaga   17040
gcaaggccgt gttttttgcct atgtacgtgt ctcgacactc gggcagacag tcgctggaca   17100
gatgcaggaa attgcggcgg ctggctttca gcccccagcg tatcgtgtcg tttcggaaac   17160
catctctggc agtgtcccgg cgatgcggcg accagagttc gcgcgcctag ttgatcgctt   17220
```

```
ggaacctggc gacattctag tcgtgtcgaa gcttgaccgt ctcggacgcg acgcaatcga   17280
cgttacggag acagtcgctg cgctctcgca gatacctgtc cgagttcatt gcctcgcttt   17340
aggtggcacg gatttgacta gctcgtctgg acagttgacg atgaacgtcc tcagcgccgt   17400
tgcgcaattt gagcgcgatt tactccgtga gcggaccagt gcaggccttg cagctgcaaa   17460
agccaaggga aaacgactag gtcgtcctaa agtgctgacc gaggataacg agagcgaagc   17520
acgagcggct ctcgccagag gggaaactgt ttctgggatt gcaaagcgtt tcaacgtcag   17580
tcgggcgacg atcggccgcc taagagatag ttaggctatc ttgcctatgt cgtcgtgacg   17640
agtcctccaa atacacggat ggcttcacgc tcccatgcac gattaaacca gtaacatgg    17700
cggcttactt ggtccttaat ctcagggcat cccatgatgt ccgctgcctt gtaagcatac   17760
cgcaagaaat tcggcgtttt ccaagatgg gtataacgcg ccaggctttc tcgcttgaat    17820
acttcaaacg acggtacgtt tttcgccttt gcggcgatca tcttggcatg aatgccccgg   17880
cgcattttc ctcggtaggc atcgagtgac gaaggtcgga tcttcgtttt ctgcccgtcg    17940
aaggtgaaac ccaaatactg gataggtgtg gcagaggcca acagtccgtc cttgaagtcg   18000
gcagtgtctg ttttgtcgat ggacatggaa aggcaaaaat ctgccagcat tttctctact   18060
actgcaacca catgatgcac cttcgcgcct agaggcagag tgaccgcgat gtcatcagag   18120
tatcttcggt aagatccccc tgccctagag caccaagcga tcatttcacg gtcaaaagtt   18180
cgaagataga tatttgcata caggccggac accggggtgc cctgcgggat accgaacgtc   18240
tggtcatgct tccgaatgag gccatccttt cggcctcgga catgatccga aaagtctgaa   18300
ggtgagcata tccttccgtg cccatttcgc tttcgaccaa gaagtttgtc tagatcttca   18360
gtctcaaccc atgagtagcg ggtcacgttt ttccaaacgc ttgcatggtg cccttccagt   18420
cttgtttcgc ctatcaaatc ggcgatctca tcgcggagca aggtgtgatc gagacagtca   18480
aagaatccgg aaatgtccat tgcgaagacc gtgcaatctc cacgagactt aatctcgtcg   18540
aacaacgcct ttgcatggtg aatattagtg ccgcccccac ggcgataggc tagcacggag   18600
tctgatgtgc cgtcgcgcca tagcgcccgc tcgtacattc tattgagatg tcccgcgtag   18660
gcttgcaggt aggctgcatc ctcatgactg gcgaagcgga tcggtcgctc tttcacttt    18720
acctcacggg cgccatcctt gttcctgaca taccttctgt tgacgtcagt aaacccaagt   18780
aaaggtagaa atctgtgagg cttatcttcg accgagaagt caaacgacag ctcccgatcg   18840
actaacggaa gatcgaaatg cttgtatttg cgttccttgg atatggccgg aagcacaaag   18900
tcgtcggttg atggatcaaa ctcgttttca gacggcaggt aaaacccggg catagcgact   18960
ccgttcgtca aatgcccggg ctattgaacc tagctcccat caacaggcac cgaggtgccc   19020
tccggtacga gaaaacctgg cgtggtatgt tgtaaccacg atgtgcgaag gatgcgccat   19080
gaccgaaatc acgaccaccc ggtgccgctg ggcgcgggta gcgcttgcgg gccttaacac   19140
tggtcatccg ggtccacgcc ccggggcaaa atatcaatta ggtgctacct aattgaatgc   19200
aaggggacgc accaagaata aaaggacttt ttcagcttta gtggcgcctt atagtggtca   19260
tctggaacca ggacaaagag acaaccttct aggtaagatc ctcgtaagtt cgtatcagtt   19320
acggtgtcag atagtagcag ataacgcacg gcgttctgct ggcggagggc gagagaaatc   19380
tggttcgctg tgagcggtat ttcttgccca caacgcggcc cttattccag tctagtacag   19440
gcttggcagc caattccgc gactggcata gcatcgtgct ccttgattac atgctaaaga    19500
ggtactttga ggtcttagcg gtcattcgac gattttgctc agataacagc gtaagtaaac   19560
```

-continued

| | |
|---|---|
| gctgccccaa gtttcaggat ctagcgccca acgatcttat cacaagagac catgttaatg | 19620 |
| cgtctattac attaggatgg ttcaaagttg ggttcgggat catctggtat tggggttcca | 19680 |
| aagaccaatt cgtgc | 19695 |

<210> SEQ ID NO 4
<211> LENGTH: 4211
<212> TYPE: DNA
<213> ORGANISM: Ketogulonigenium
<220> FEATURE:
<221> NAME/KEY: misc_feature
<223> OTHER INFORMATION: pADMX6L4

<400> SEQUENCE: 4

| | |
|---|---|
| gcgtggccct tcccgccgag ctggacgccg aagcccaagc ccggcttgtc cgcacctggg | 60 |
| cacgggacca cctggccgcc gccggcatcg tcgcggacat cgccattcac gagccgagcc | 120 |
| gcgaaggcga cgaccgcaac acccatgccc acatcatgac caccctgcgg cgtttcgacg | 180 |
| gggcaaccgt ggacggatgg gcgaagggtg ccgcccgcga cctgaacgac aaggcgttcc | 240 |
| tcgagaacct gcgggcatcg tgggagaccc ccagaacgc cgcactggag gccgccgggt | 300 |
| caaccgcacg ggttgaccac cgcacccttg ccgcacagca tgaggacgcc ttggccgcag | 360 |
| gtgatgactt actggccgcc gtcctcaacc gccccccgga acctcacctg gcgtgtcgg | 420 |
| cccaagcgat tgaccgccgg gccggcgtc cggtcagcaa ccggggccgg gccttggcgg | 480 |
| aggtcaggga gacccgcacc cggctcatga cggcatacga cacggcacgg agggccgccg | 540 |
| tgttcatcgc aacgaccacc gccgggcttg ttgaccgggt gtccggtgcc cggtcagaga | 600 |
| ccggacaccc cattgcccga atgttcggcc ttggccgtca tgcggcaact gttgccgaca | 660 |
| ccgtgccaga accgtcccgc ccatcgccgg acgacgatac cccgtccccg tcctgacccg | 720 |
| cctcaaaccg tgccgatgca gcggcctctt taagcccact ctgtgcctct tcggcggccc | 780 |
| tgtgctgtct ggccatccag aaatccagaa tggccgcacc acgcatggct tcggcctcgg | 840 |
| cgtcccgtgc ctcgtccaga cctgcccgga ccaccaccgc tcagcggtt ccgtgcatgt | 900 |
| ccagatgtgc ggccaccatg tccaacacgg cggccctgac ttcctcgggc gacacctcgg | 960 |
| cccccatcca atcgtggccg aacttctcgg ccacgatgcg tgacaccgcc gccttgcaga | 1020 |
| aggtccgggc atactgctcc agaccgtatg cagccttgtc ctcgaccgtc cgagcgtcag | 1080 |
| gcgccttgat gaccctctga actgccattg atgcccttt ctcgacttcg attagtgccg | 1140 |
| caatttgctc gaccatgcta cgaacccaat ggacggtccc cagcagacgc cacgccccat | 1200 |
| tccgtgccag acctgcggcc ccggccttct tgtccgattt gggcgaaaac cggaactcaa | 1260 |
| cccgcacaag atgcgggtcc gcgtcctcga tggccaactt gccgtccgcc acccgttcaa | 1320 |
| ggtctttctg ataaaccttc acggacgcct caccccttgcc ccaatagaag gtccggcccg | 1380 |
| tgtcgctctc gatgacacgc ggggccgcca tcttggacgc cttggacatg cggcgggcat | 1440 |
| agtccagcaa ggcgtccatc aaaccctctt ggctatggtc catcgacacg tcagcacgag | 1500 |
| ccagcaggga gggaccaaag gcgttcaggg cctgcggggc cagcagcgca caacgaccat | 1560 |
| caccaccggg tatttcaagg ctcggcatgt ttctggcatg ccctgcccgc accgtagccc | 1620 |
| ggcgttcctc atcaatgggt gagtccgcgt aatgcaaggc acccgcgaaa ccgtccgtcc | 1680 |
| cgttgcccac gcgttgagtg tgcagaccag ccagcacaga ccagagacaa aaggcatccc | 1740 |
| gtgcctctct tgcctcttcc tcgcccatcc tgtcctcgta gtgaatgaca cgcatggcct | 1800 |
| caacgcgttc agtgccgtt aagcgggcag cctcggcaac ctccgacggg tcagccctgc | 1860 |

-continued

```
ggcgttcgcc cttgccgttc cgcccgttag gcaacgtgat tgtgagccag tcgaaaaacc     1920
acgccgtttg cagccatttt tccatgaccg ggctggtttt cttgcccttc cttcgcttct     1980
ccgaaggtgg ggggcacttt ggggcacaaa ccgccggttt tacgccgttc ggggcctgct     2040
tttcacattg aaaatcaggt gtttgccccg aactaccccc cctgttagca tgtgggggt     2100 tttgggcctt gcggcggacc tcatcgagag ccgcgaccgc ctgctgtgaa agggttttac     2160
cgccgtggac catcatcgcg tctcccgttg agggtggacg cggtctcaag catgttgatt     2220
cttgcgaatg acatggctat atctctccaa agttctgagg acgacgcggg gaccgcgaaa     2280
tcacagcgtt cgtccaggtt aagggctccg gttaatcccg gagccttcc atttcatatg      2340 aacgacatcc ggaaaaatca acatattgat gccgctggac gatgtgcggc caagatgtgc     2400
tgcagtattc ccggcgggcg gaaccgttcc gatatttgaa gtctccacgc ttccgcccgc     2460
ctaatgtcgt tctgtcgttg aactttcata aaggtgaaac cctgctggtt tcccccggcg     2520
gcgaagccgc ctcccccttc ctgcctcaca aaaaaggga aaaggcccgt tcaaccgat      2580 cgacgcaatc tccttcacg gtatccagat acctttctg gtgaagccat ccgaaacaaa      2640
ggccgcgagt cgtcacacct gggcttgacc gacgcgaatc actcggacag tgtccggtca     2700
tggaccacat gctgaccca aaacaggcgg cggcccgtgc gggctgcggg cgttcctcta     2760
tcatgagggc gttaaagtcc caatctttgc ccgctatacg cgataatgag aaccgctggc     2820
agattgaccc ggacgccctt gaccgttggg ccggtcacag gccggacaat gaccggtcta     2880
tgaccgaaca cggaccggcc acaccttcgg acacccaaac ggacacccg gagaccttgg      2940 cacggctcgc cgttgccgag gcccggttga gtgatgccct gtcccgcgtc gaagatttgc     3000
agagagaacg ggatgaatgg cgggcacagg cacaagcctt gacccgtcag cccggttggc     3060
tggaccgcct actgggtcga acctgacccc ccatcgtcac ctttggcctc accagcggat     3120
tgcttgtgaa ccaaggccag cagttccttg acctgttcca cgctaccgc ttcggcttca      3180 atatcgccca tcttgacgcg gacctttcgg ccttgtctcg cagccaccca tccaccgata     3240
gcaccaatca cagccggacc gagggttgtg gccatcatcg tgaactcacc caaaaaagtg     3300
atgccaccag agccagccga gtccctgatg aacgctcgct ccgaatattt tatgtcctgt     3360 tcttcagga tggtgcggaa ctccccggca tcttctttcg ggaaaaccgc gatttctaaa      3420
tcactcatgg aatgctcctt tgcccatga ggtaataatg ccctgccaat gagcaccgag      3480
caaatcagcc gggttgctct ttcgaaacgg tctcgggctt tggaagtgtc cacccctcga     3540
acagtgcccg gtctctctct ggcatcgagg caatcgccat ccgcagcacc ttgacccatt     3600
gaggatcttt tgcagcttgc ccgataaccg caccgcccag gacgattttc gccgtgcgt      3660 cctttttcg gtcctctgcc cgaagttttg ccccggcttg tcgtatctgg gcctctgccc      3720
tcgccttggc ctctttggcc cgctctaact gcctttctac tgaagttctt gccatttccc      3780
gtcctccttc atagggccta tatgaacgga gagggaacga agcaagaagt tctcaagaac      3840
ccgaagggcg cacttacaca aactctgggg agtttgtttc gggcgcccta ccggggggtca    3900 tctcgccgat ggggcgtctc cgacggtaaa aagaggaggg gccgccgtgg cgatatatca    3960
cctgtccgcg tccattatcg ggcgaagcga tggccggtca gccgttgccg cgtcagcata    4020
tcgggccggg gccgacatga ccgacccgga caccgggacg cggcacgact acacccgaaa    4080
gcgaggcgtc cgggcaacct tcatggagtt gcccgaaggt gccccgatt gggccaccga     4140 ccgcccgagc ctctggaacg ccgtccacgc gaaggagacg cggaagaact cgcggctttc    4200
gcgtgagatc c                                                          4211
```

<210> SEQ ID NO 5
<211> LENGTH: 1458
<212> TYPE: DNA
<213> ORGANISM: Ketogulonigenium
<220> FEATURE:
<221> NAME/KEY: misc_feature
<223> OTHER INFORMATION: replicon pADMX6L1

<400> SEQUENCE: 5

| | | | | | |
|---|---|---|---|---|---|
| abgggccttg | catccgatgg | caagcaaaaa | ctacccagtc | cgtccgtagg | cgggggtcg | 60 |
| ccagccctgt | gggtgggcgc | ttcccccgg | cccgcaagcg | ggcccggaat | gggcattttt | 120 |
| tgcctgccct | aagatcataa | gaagggcaaa | aaaaacatcg | tttcaaaaca | gcgtgttacc | 180 |
| accccctat | aggacaccag | agtccggggt | agaggactct | ggtgtcctct | taggccattt | 240 |
| atgtccaaga | atgtgacagc | cagccgagcg | gaggtagagg | actctggtgt | cctatgctta | 300 |
| ggccatttat | gtccaaaaac | ttgacaaggg | ccacattcct | gccaaatctg | tccagaattt | 360 |
| ggaaaattc | gccggatagt | agacagtggc | aaagcctccc | cccattcccg | caaagcgccc | 420 |
| gctcggcact | tgggttcaaa | ctgaccggga | agcccacgag | gcgtgggcga | tactggcaaa | 480 |
| aaagcctgct | gccagcgctg | tgatgcacat | tctgtgcgcc | aacctcggtg | agcataatgc | 540 |
| cgtggtcatc | agccaggaca | ccatcgccaa | gctgtgcggc | cttccacac | ggtccgtcag | 600 |
| gcgcgccatc | gtcgatctgg | ccgaaggccg | atggatcgag | gttcgccaac | ttggcgcgac | 660 |
| cagccagacc | aatgcctatg | tcgtcaacga | ccgggtggca | tggcagggat | cacgggacgg | 720 |
| actgcgctac | agcctgttta | gtgcggctat | agtcgtgtcc | gaggaggagc | aacccgaccg | 780 |
| cgctgaactc | gaccagcaag | cccccctgcg | cacctgcca | cgcatcagcg | aggggcagat | 840 |
| acccaccggc | cccggcctgc | cgccaccttc | gcaaccgttt | ctaaaagaca | tggagccaga | 900 |
| cttgcccacc | attgaccggg | caacatcacc | caactttgac | cagcaggaac | aggggtgaaa | 960 |
| aaggtggaca | aactttccat | acgcgaggcg | gtaaaacact | tcgatgtttc | ccggccaacc | 1020 |
| ctgcaaaaag | cccttaaatc | tggcaagatt | tcaggtgttc | aggatggaca | aggaacgtgg | 1080 |
| acaatagacc | cctcagagat | ggcaagagtt | taccagccaa | gcaagatga | ggtggtaaag | 1140 |
| gatggtggcc | aagaacatga | aaatttgtcc | gccaagaaca | cccctttaca | tggtcaagtt | 1200 |
| gaggttctga | aagagcggct | tgcagatgct | gaaaaacggg | tggcgatagc | cgaggcactg | 1260 |
| gccgaagaac | gtggaaaaca | catcgaggat | ctacgccgga | tgctgcctgc | accggaagcc | 1320 |
| ggtcagcccc | gccgccgctg | gtggccatgg | taaggtcagc | tatgcgggac | caagccgcag | 1380 |
| ctcgcaagtg | cggcaacaga | atcagacccg | cttcggacag | agagctcaag | ctggtggaaa | 1440 |
| accgcctgtg | aagctgct | | | | | 1458 |

<210> SEQ ID NO 6
<211> LENGTH: 2401
<212> TYPE: DNA
<213> ORGANISM: Ketogulonigenium

<400> SEQUENCE: 6

| | | | | | |
|---|---|---|---|---|---|
| caccatggcg | cgctgcagct | cttctttgct | tctgttggtt | cttctctcgt | caagaagctc | 60 |
| aggcggaaac | cgcactataa | agtgcagaac | aggcttcttc | gccgctttgt | tttgcctaac | 120 |
| gccttttgtg | tgcgcgtcat | atgccgaccg | aaggtctagc | gtcttataaa | cgagcggaga | 180 |
| ggcatctctt | acgacgcgtt | tcgcacttgt | tttgtcttgt | cgtttcgcgt | gcttttcggc | 240 |
| tgctgacaat | ccagccatat | ctaacgcact | acatctcacc | gctgctttca | ttttcaatcc | 300 |

```
ctcatatatt  acctttttctg  ttgttttttgc  gaaaaacgca  aaactcgctt  tgcgtttttt    360
gttcggcacc  tgcggcacct  ccaaaaaaca  cgcttgctct  ccgagggtct  ggcaggagcc    420
taagaggggg  cattctgccc  ctgatcgacc  ccattgaggc  tcgatctaaa  cagaccccc    480
acagggcgt  ctgtgggccg  ctagtgcggc  cttccgccat  cttcgagcca  tctgatctct    540
gcaattagag  atgcatggcg  catctcccat  tccagctcag  atatcccgta  tctgtcgatg    600
acggtgtcat  acaattcgtc  gagccttgct  tcgcgctctt  cttttgtcat  gccagttgca    660
tcgcgttctt  ccatctcctc  gttctcctct  atgatgaaat  cattttcgtc  ctcgtcgttt    720
ggcccgcttt  ctgctgcctt  gaccgcaaca  cgcctccgc  gctctgcggc  ctcgagcaag    780
ttcacgcgtt  tagcgcgcac  ttgcttccac  ccttcattgt  cccactccgc  gacaatttca    840
gggccgcttt  gctctgctgc  atcaacttca  gccatagctt  catcgtcatc  cagctcgacc    900
aaaccgcatt  cttctttcaa  gccttggctc  cacaccaatt  gccgcctacg  cttgccgctc    960
gttgcattga  aatattcgag  ccaaagcccg  tcatcgcccg  cctgaagtag  ctgccttggc   1020
gtgcgtcctt  tgcgttttcc  gctcttcgag  cttgaaagcg  tcaactcttc  ggcagcgccc   1080
cacttcgcta  cgtagtcgcc  cgcattggca  gccccgcgaa  cgtcaaacgc  cgcatcgttg   1140
ccccacatgc  cataccccctt  cagacatgca  cgccacgcat  cgcctagacg  ttgcatcaga   1200
tgcagcgctt  cgctttcatc  gccagctctt  agcaagacaa  tttcgtgaaa  gtgcgggtgc   1260
cacccatttg  catagctatg  agtaatttca  gttgatgtga  ctgacccaac  aaatggtaaa   1320
tcgcgccact  cgcggcgctg  acgcaaccgc  tgtttcgcct  tcttcatgtt  ttggagaaga   1380
tcaaaaagcg  aatcacctgc  tttgtgctgg  gctgtcagag  ttatgagcac  cggcacaaac   1440
ccgttgtcgc  gcgcccacgc  gagcaagtga  ttcatttcag  aacggcgaat  ttgcgcgatg   1500
cgagcgctac  aaactgcgca  gccccacaca  ttccggcact  gtgctagacc  tgaaaagaat   1560
gcccgacgcc  cgccatcctc  gcccacgttt  tgcacgttta  gctcaactgt  cggagacact   1620
tttacgtgcc  gacatttcgc  aacttggtgg  ggcttgtttt  tgttcagatt  caacagaatc   1680
cgagcggctg  aacgcagatc  tgcataaagc  tgccgcctac  tgaataacct  gttgttttct   1740
ttgttttttt  cattcggttg  accccccattc  tggtcaaccg  atttacggta  tataccaagg   1800
ggggtctgcc  gaccccctga  aaaagcgtca  tcgccgcgcg  cctgcgcacc  cgcgttcttc   1860
ttcgatttct  gaactgaatg  tgatgctagt  ttgtgagaca  tggccgcaaa  ccccgacggg   1920
tgcggcgact  attctcttga  ttttctgcgt  ctgtgcgcat  actatcctcc  gtgttcatca   1980
ggctcacgcc  tgatctgatt  agggctcttg  tctctgcttg  tatcgtcgcc  aaactatact   2040
ttaagcagcg  tctagagcct  gatgaacgat  ctaagaagcc  cgcccctga  aaggcgggct   2100
tttttgatct  gtgccagatg  ttgttacatc  ggcgctcaaa  aatcaagttt  tttcttgact   2160
ttcaataatt  tgcattatgc  acattattat  cgtttgataa  taagagccag  aacagcacag   2220
aatagttgtg  cgatagctat  gaataatagc  agatccatcc  ctgtttcctt  tcttactaaa   2280
tacaatgcga  aactgctcgc  atctgtttta  tttagttgaa  tcggaaactc  caaatcggcc   2340
ggattcaaaa  aaaatataga  ctatctttaa  agtagcaacg  ccgccgctcg  cgcgacggca   2400
t                                                                        2401

<210> SEQ ID NO 7
<211> LENGTH: 2029
<212> TYPE: DNA
<213> ORGANISM: Ketogulonigenium
<220> FEATURE:
```

<221> NAME/KEY: misc_feature
<223> OTHER INFORMATION: replicon pADMX6L3

<400> SEQUENCE: 7

```
agagaataag atcaggtctg ttctcgtgcc gccagcggtt aagcaggtta tagagccgaa      60
attcactctt attcatcaat tgcttgctgc tgtagagcga ttttcgccct tcaacgaacc     120
agtagacacc cccgacaagg gcgatgacca ccagaaatcc aattatcatt gtgaaattaa     180
tgtcggtcat gactgcactc cctcaaggcc gaagtcagag attgcatctt gacgcagagc     240
gacgagttca acgccgtcga tgcggttttg ggtggcggta gccgggctgg cgcggatacg     300
cctaccgttg gcacggtttc taggcgacat actgaggcaa accggatttc cagtgggctg     360
cgtgctttgt tgtaagcgcg ccatttcatc ccccgaggg caggggaacg gctcacaact      420
tccaaaggcc ccgaaaaatt ctcgcgatga ccccaccacg ggatttgtgc aacacaatcg     480
gcgcgcggga caggctcata tcaacttgga taagcgccgc gttttttgca aaatgcgaga     540
aagtgcttat ccgcatcttt cacgttgatg gccttgtcat gcacccaaga acgccactct     600
tcttcaaggg agtaaacatc ccacccagga gcaagttcac gggcagtatc gcgtgtgtcg     660
ggatcgttga acggcaaggc ctgaaaagtg gttgatgcta tagtttccac caccttgggt     720
cggaagacag cgttctctcc ttcgatactc atgctgtagt cagggaagtg gtcgtgcgcg     780
gtgtcatcct caatgatctt cgaaagcagg cgacggaact ctttttttagt tgagccggaa     840
ccgcacttgt ttcgcaagag ctccaagcta cacatccatt ttgactgcgc gccacaatgc     900
tttcgcccta tctcatacaa ccgcctttcg aggggctttc tgagcaggaa ataccccgg      960
cttagagtga ggacatggtt gttctcgatc gcatcaaaga cccagtcaga gagcgttatt    1020
tcgacatcaa gcattcggcc gtcgcgggtt acgcgcacga tctcggctga ttcaatcagg    1080
ccaaatacct tgaagtattc tttcccacct tgacgaatat tcgtttcaat ttgggttccc    1140
tgcagccgcc gaagggcatc tttgagcagc tgataaccct gaccggatgt ctgacggttc    1200
gttgccacaa gcagatcata agccttgaaa cgcatcgatc tacttatttt ctgcccctca    1260
ttaatggccg ccatgcactg gctgatgcag tagatcagca catcacggtc atgaacggta    1320
gcaaggccat agcgtgaagg ggaaaacctcg atccaattgt cgttgttctg atagcggcgt    1380
ggcttcatgt ccggctttgt agacagggtg aacataggt gctccatcga agccatatcc     1440
cccttgggaa ccgcatcaac gatgtcgcaa acgaaaaggt cttttttgtgg atgacgatcc    1500
ggcaaaagcg gtgatcgtag gttcgtcatt tcacacactc ccgcgccaag taaaaattcg    1560
tcatttcaca caccgtacaa gactatcgtc atttcacaca ccactcgtca aggctcgtca    1620
tttcacacac ccaaggaggc tgtggataac tcgagccgct atcgtcattt cacacaccat    1680
ctttcgtcat ttcacacacc atctttcgtc atttcacaca ccaggtgtta ttttttttat    1740
agttatatca attgattacg agctgttttc ggagctgtaa ctctattcta actctattct    1800
aactctcata gcttgccaaa atggcacctc atatcccgga tatccggttt cattatgaaa    1860
ccaatcaaca acatttacgg tgttttttga ggagcaacac tgtcccaacg caggttcaaa    1920
ccgatcacgc cgaatctgca aagaaagggg cagtgctatg ttcatttggt cactcgagga    1980
tcacccgaac cacaggtaag ccctcacatg ctatgttgat acctccagg             2029
```

<210> SEQ ID NO 8
<211> LENGTH: 151
<212> TYPE: PRT
<213> ORGANISM: Ketogulonigenium -continued

```
<400> SEQUENCE: 8

Met His Ile Leu Cys Ala Asn Leu Gly Glu His Asn Ala Val Val Ile
1               5                   10                  15

Ser Gln Asp Thr Ile Ala Lys Leu Cys Gly Leu Ser Thr Arg Ser Val
            20                  25                  30

Arg Arg Ala Ile Val Asp Leu Ala Glu Gly Arg Trp Ile Glu Val Arg
        35                  40                  45

Gln Leu Gly Ala Thr Ser Gln Thr Asn Ala Tyr Val Val Asn Asp Arg
    50                  55                  60

Val Ala Trp Gln Gly Ser Arg Asp Gly Leu Arg Tyr Ser Leu Phe Ser
65                  70                  75                  80

Ala Ala Ile Val Val Ser Glu Glu Gln Pro Asp Arg Ala Glu Leu
                85                  90                  95

Asp Gln Gln Ala Pro Leu Arg His Leu Pro Arg Ile Ser Glu Gly Gln
            100                 105                 110

Ile Pro Thr Gly Pro Gly Leu Pro Pro Ser Gln Pro Phe Leu Lys
        115                 120                 125

Asp Met Glu Pro Asp Leu Pro Thr Ile Asp Arg Ala Thr Ser Pro Asn
    130                 135                 140

Phe Asp Gln Gln Glu Gln Gly
145                 150

<210> SEQ ID NO 9
<211> LENGTH: 466
<212> TYPE: PRT
<213> ORGANISM: Ketogulonigenium

<400> SEQUENCE: 9

Met Ser His Lys Leu Ala Ser His Ser Val Gln Lys Ser Lys Lys Asn
1               5                   10                  15

Ala Gly Ala Gln Ala Arg Gly Asp Asp Ala Phe Ser Gly Gly Arg Gln
            20                  25                  30

Thr Pro Leu Gly Ile Tyr Arg Lys Ser Val Asp Gln Asn Gly Gly Gln
        35                  40                  45

Pro Asn Glu Lys Asn Lys Glu Asn Asn Arg Leu Phe Ser Arg Arg Gln
    50                  55                  60

Leu Tyr Ala Asp Leu Arg Ser Ala Ala Arg Ile Leu Leu Asn Leu Asn
65                  70                  75                  80

Lys Asn Lys Pro His Gln Val Ala Lys Cys Arg His Val Lys Val Ser
                85                  90                  95

Pro Thr Val Glu Leu Asn Val Gln Asn Val Gly Glu Asp Gly Gly Arg
            100                 105                 110

Arg Ala Phe Phe Ser Gly Leu Ala Gln Cys Arg Asn Val Trp Gly Cys
        115                 120                 125

Ala Val Cys Ser Ala Arg Ile Ala Gln Ile Arg Arg Ser Glu Met Asn
    130                 135                 140

His Leu Leu Ala Trp Ala Arg Asp Asn Gly Phe Val Pro Val Leu Ile
145                 150                 155                 160

Thr Leu Thr Ala Gln His Lys Ala Gly Asp Ser Leu Phe Asp Leu Leu
                165                 170                 175

Gln Asn Met Lys Lys Ala Lys Gln Arg Leu Arg Gln Arg Glu Trp
            180                 185                 190

Arg Asp Leu Pro Phe Val Gly Ser Val Thr Ser Thr Glu Ile Thr His
        195                 200                 205
```

```
Ser Tyr Ala Asn Gly Trp His Pro His Phe His Glu Ile Val Leu Leu
    210                 215                 220

Arg Ala Gly Asp Glu Ser Glu Ala Leu His Leu Met Gln Arg Leu Gly
225                 230                 235                 240

Asp Ala Trp Arg Ala Cys Leu Lys Gly Tyr Gly Met Trp Gly Asn Asp
            245                 250                 255

Ala Ala Phe Asp Val Arg Gly Ala Ala Asn Ala Gly Asp Tyr Val Ala
        260                 265                 270

Lys Trp Gly Ala Ala Glu Glu Leu Thr Leu Ser Ser Lys Ser Gly
    275                 280                 285

Lys Arg Lys Gly Arg Thr Pro Arg Gln Leu Leu Gln Ala Gly Asp Asp
290                 295                 300

Gly Leu Trp Leu Glu Tyr Phe Asn Ala Thr Ser Gly Lys Arg Arg Arg
305                 310                 315                 320

Gln Leu Val Trp Ser Gln Gly Leu Lys Glu Glu Cys Gly Leu Val Glu
            325                 330                 335

Leu Asp Asp Asp Glu Ala Met Ala Glu Val Asp Ala Ala Glu Gln Ser
        340                 345                 350

Gly Pro Glu Ile Val Ala Glu Trp Asp Asn Gly Trp Lys Gln Val
    355                 360                 365

Arg Ala Lys Arg Val Asn Leu Leu Glu Ala Ala Glu Arg Gly Gly Ala
370                 375                 380

Val Ala Val Lys Ala Ala Glu Ser Gly Pro Asn Asp Glu Asp Glu Asn
385                 390                 395                 400

Asp Phe Ile Ile Glu Glu Asn Glu Glu Met Glu Glu Arg Asp Ala Thr
            405                 410                 415

Gly Met Thr Lys Glu Glu Arg Glu Ala Arg Leu Asp Glu Leu Tyr Asp
        420                 425                 430

Thr Val Ile Asp Arg Tyr Gly Ile Ser Glu Leu Glu Trp Glu Met Arg
    435                 440                 445

His Ala Ser Leu Ile Ala Glu Ile Arg Trp Leu Glu Asp Gly Gly Arg
450                 455                 460

Pro His
465

<210> SEQ ID NO 10
<211> LENGTH: 342
<212> TYPE: PRT
<213> ORGANISM: Ketogulonigenium

<400> SEQUENCE: 10

Met Thr Asn Leu Arg Ser Pro Leu Pro Asp Arg His Pro Gln Lys
1               5                   10                  15

Asp Leu Phe Val Cys Asp Ile Val Asp Ala Val Pro Lys Gly Asp Met
            20                  25                  30

Ala Ser Met Glu His Pro Met Phe Thr Leu Ser Thr Lys Pro Asp Met
        35                  40                  45

Lys Pro Arg Arg Tyr Gln Asn Asn Asp Asn Trp Ile Glu Val Ser Pro
    50                  55                  60

Ser Arg Tyr Gly Leu Ala Thr Val His Asp Arg Asp Val Leu Ile Tyr
65                  70                  75                  80

Cys Ile Ser Gln Cys Met Ala Ala Ile Asn Glu Gly Gln Lys Ile Ser
                85                  90                  95

Arg Ser Met Arg Phe Lys Ala Tyr Asp Leu Leu Val Ala Thr Asn Arg
            100                 105                 110
```

```
Gln Thr Ser Gly Gln Gly Tyr Gln Leu Leu Lys Asp Ala Leu Arg Arg
            115                 120                 125

Leu Gln Gly Thr Gln Ile Glu Thr Asn Ile Arg Gln Gly Gly Lys Glu
        130                 135                 140

Tyr Phe Lys Val Phe Gly Leu Ile Glu Ser Ala Glu Ile Val Arg Val
145                 150                 155                 160

Thr Arg Asp Gly Arg Met Leu Asp Val Glu Ile Thr Leu Ser Asp Trp
            165                 170                 175

Val Phe Asp Ala Ile Glu Asn Asn His Val Leu Thr Leu Ser Arg Gly
            180                 185                 190

Tyr Phe Leu Leu Arg Lys Pro Leu Glu Arg Arg Leu Tyr Glu Ile Gly
            195                 200                 205

Arg Lys His Cys Gly Ala Gln Ser Lys Trp Met Cys Ser Leu Glu Leu
            210                 215                 220

Leu Arg Asn Lys Cys Gly Ser Gly Ser Thr Lys Lys Glu Phe Arg Arg
225                 230                 235                 240

Leu Leu Ser Lys Ile Ile Glu Asp Asp Thr Ala His Asp His Phe Pro
            245                 250                 255

Asp Tyr Ser Met Ser Ile Glu Gly Glu Asn Ala Val Phe Arg Pro Lys
            260                 265                 270

Val Val Glu Thr Ile Ala Ser Thr Thr Phe Gln Ala Leu Pro Phe Asn
            275                 280                 285

Asp Pro Asp Thr Arg Asp Thr Ala Arg Glu Leu Ala Pro Gly Trp Asp
        290                 295                 300

Val Tyr Ser Leu Glu Glu Glu Trp Arg Ser Trp Val His Asp Lys Ala
305                 310                 315                 320

Ile Asn Val Lys Asp Ala Asp Lys His Phe Leu Ala Phe Cys Lys Lys
                325                 330                 335

Arg Gly Ala Tyr Pro Ser
                340
```

KETOGULONIGENIUM ENDOGENEOUS PLASMIDS

CROSS-REFERENCE TO RELATED APPLICATIONS

This non-provisional application is a divisional application of U.S. Application No. 09/826,191, filed Apr. 5, 2001, now abandoned, which claims the benefit of U.S. Provisional Application No. 60/194,627, filed Apr. 5, 2000, the contents of each of which are incorporated herein by reference.

BACKGROUND OF THE INVENTION

1. Field of the Invention

The present invention relates, in general, to a novel genus of bacteria known as *Ketogulonigenium*. The present invention further relates to transformed *Ketogulonigenium*, and methods of transforming *Ketogulonigenium*. The present invention also relates to nucleic acid molecules, and vectors.

2. Background Art

The exploitation of microorganisms to synthesize vitamin C or its chemical pathway intermediates has both economic and ecological advantages. One key intermediate in vitamin C synthesis is 2-keto-L-gulonic acid (2-KLG), which is easily converted chemically to L-ascorbic acid (vitamin C) by esterification followed by lactonization (Delic, V. et al., "Microbial reactions for the synthesis of vitamin C (L-ascorbic acid)," in *Biotechnology of Vitamins, Pigments and Growth Factors*, Vandamme, E. J., ed., Elsevier Applied Science (London & New York) pp. 299–336 (1989)). Members of a number of bacterial genera have been identified that produce 2-KLG from the oxidation of L-sorbose or sorbitol. Such 2-KLG producing genera include the acidogenic, alpha-proteobacteria *Gluconobacter* and *Acetobacter*, the gamma-proteobacteria *Pseudomonas, Escherichia, Klebsiella, Serratia* and *Xanthmonas* and the Gram positive *Bacillus, Micrococcus* and *Pseudogluconobacter* (Imai, K. et al., U.S. Pat. No. 4,933,289 (1990), Sugisawa, H. et al., "Microbial production of 2-keto-L-gulonic acid from L-sorbose and D-sorbitol by *Gluconobacter melanogenus*," *Agric. Biol. Chem.* 54:1201–1209 (1990), Yin, G. et al., U.S. Pat. No. 4,935,359 (1990), Shirafuji, et al., U.S. Pat. No. 4,876,195 (1989) and Nogami, I. et al., U.S. Pat. No. 5,474,924 (1995)).

To aid in increasing the yield of bacterial products, attempts have been made to exploit endogenous plasmids within microorganism strains. (Beppu, T. et al., U.S. Pat. No. 5,580,782 (1996), Fujiwara, A. et al., U.S. Pat. No. 5,399,496 (1995); Tonouchi et al, U.S. Pat. No. 6,127,174 (2000), Hoshino, T. et at., U.S. Pat. No. 6,127,156 (2000)).

BRIEF SUMMARY OF THE INVENTION

One aspect of the present invention provides an isolated or purified nucleic acid molecule comprising a polynucleotide having a nucleotide sequence at least 95% identical to a nucleotide sequence of a *Ketogulonigenium* plasmid replicon found on the endogenous plasmid contained in NRRL Deposit No. B-21627 and at least one exogenous nucleotide sequence.

Further embodiments of the invention include an isolated or purified nucleic acid molecule comprising a polynucleotide having a nucleotide sequence at least 90% identical, and more preferably at least 95%, 97%, 98% or 99% identical, to any of the above nucleotide sequences, or a polynucleotide which hybridizes under stringent hybridization conditions to a polynucleotide having a nucleotide sequence as in the above. The polynucleotide which hybridizes does not hybridize under stringent hybridization conditions to a polynucleotide having a nucleotide sequence consisting of only A residues or of only T residues.

The present invention relates, in general, to a novel genus of bacteria known as *Ketogulonigenium*. The present invention further relates to *Ketogulonigenium* comprising a transgene (recombinant DNA), comprising an endogenous plasmid. The invention also relates to a method for transforming *Ketogulonigenium* comprising conjugative transfer of a vector from *E. coli* to *Ketogulonigenium*, and to a method for transforming *Ketogulonigenium* comprising electroporation.

The invention provides a nucleic acid molecule comprising a nucleotide sequence at least 95% identical to a *Ketogulonigenium* endogenous plasmid contained in NRRL Deposit No. B-21627. The invention also provides a nucleic acid molecule comprising a polynucleotide having a sequence at least 95% identical to a *Ketogulonigenium* replicon found on an endogenous plasmid contained in NRRL Deposit No. B-21627. The invention further provides a vector comprising a nucleic acid molecule comprising a nucleotide sequence of a *Ketogulonigenium* replicon found on an endogenous plasmid contained in NRRL Deposit No. B-21627.

Further advantages of the present invention will be clear from the description that follows.

BRIEF DESCRIPTION OF THE FIGURES

FIGS. 1A–1E show the nucleotide (SEQ ID NO:1) sequence of an endogenous plasmid, determined by sequencing of the endogenous plasmid (pADMX6L1), contained in NRRL Deposit No. B-21627. The nucleotide has a sequence of about 7029 nucleic acid residues.

FIGS. 2A–2C show the nucleotide (SEQ ID NO:2) sequence of an endogenous plasmid, determined by sequencing of the endogenous plasmid (pADMX6L2), contained in NRRL Deposit No. B-21627. The nucleotide has a sequence of about 4005 nucleic acid residues.

FIGS. 3A–3N show the nucleotide (SEQ ID NO:3) sequence of an endogenous plasmid, determined by sequencing of the endogenous plasmid (pADMX6L3), contained in NRRL Deposit No. B-21627. The nucleotide has a sequence of about 19,695 nucleic acid residues.

FIGS. 4A–4C show the nucleotide (SEQ ID NO:4) sequence of an endogenous plasmid, determined by sequencing of the endogenous plasmid (pADMX6L4), contained in NRRL Deposit No. B-21627. The nucleotide has a sequence of about 4211 nucleic acid residues.

FIGS. 5A–5B show the nucleotide (SEQ ID NO:5) sequence of the replicon on an endogenous plasmid (pADMX6L1), determined by homology of amino acid sequences encoded by the endogenous plasmid to known replication proteins, contained in NRRL Deposit No. B-21627. The nucleotide has a sequence of about 1456 nucleic acid residues.

FIGS. 6A–6B show the nucleotide (SEQ ID NO:6) sequence of the the replicon on an endogenous plasmid (pADMX6L2), determined by homology of amino acid sequences encoded by the endogenous plasmid to known replication proteins, contained in NRRL Deposit No. B-21627. The nucleotide has a sequence of about 2401 nucleic acid residues.

FIGS. 7A–7B show the nucleotide (SEQ ID NO:7) sequence of the the replicon on an endogenous plasmid (pADMX6L3), determined by homology of amino acid sequences encoded by the endogenous plasmid to known replication proteins, contained in NRRL Deposit No. B-21627. The nucleotide has a sequence of about 2029 nucleic acid residues.

FIG. 8 shows the amino acid sequence (SEQ ID NO:8) of a replication protein encoded by an endogenous plasmid (pADMX6L1) determined from the nucleotide sequence of pADMX6 μl contained in NRRL B-21627. The polypeptide has a sequence of about 151 amino acids in length.

FIG. 9 shows the amino acid sequence (SEQ ID NO:9) of a replication protein encoded by an endogenous plasmid (pADMX6L2) determined from the nucleotide sequence of pADMX6L2 contained in NRRL B-21627. The polypeptide has a sequence of about 466 amino acids in length.

FIG. 10 shows the amino acid sequence (SEQ ID NO:10) of a replication protein encoded by an endogenous plasmid (pADMX6L3) determined from the nucleotide sequence of pADMX6L3 contained in NRRL B-21627. The polypeptide has a sequence of about 342 amino acids in length.

DETAILED DESCRIPTION OF THE INVENTION

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence in is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

In another aspect, the invention provides an isolated nucleic acid molecule comprising a polynucleotide which hybridizes under stringent hybridization conditions to a portion of the polynucleotide in a nucleic acid molecule of the invention described above, for instance, in the endogenous plasmids contained in NRRL Deposit No. B-21627. By "stringent hybridization conditions" is intended overnight incubation at 42° C. in a solution comprising: 50% formamide, 5×SSC (150 mM NaCl, 15 mM trisodium citrate), 50 mM sodium phosphate (pH7.6), 5× Denhardt's solution, 10% dextran sulfate, and 20 μg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotide (e.g., the deposited endogenous plasmid), for instance, a portion 50–750 nt in length, or even to the entire length of the reference polynucleotide, also useful as probes according to the present invention, as are polynucleotides corresponding to most, if not all, of the nucleotide sequence of the deposited DNA or the nucleotide sequence as shown in FIG. 1 (SEQ ID NO:1). By a portion of a polynucleotide of "at least 20 nt in length," for example, is intended 20 or more contiguous nucleotides from the nucleotide sequence of the reference polynucleotide, (e.g., the deposited DNA or the nucleotide sequence as shown in FIG. 1 (SEQ ID NO:1)). As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, edited by Sambrook, J., Fritsch, E. F. and Maniatis, T., (1989), Cold Spring Harbor Laboratory Press, the entire disclosure of which is hereby incorporated herein by reference.

By a polynucleotide having a nucleotide sequence at least, for example, 95% "identical" to a reference nucleotide sequence is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequence shown in FIG. 1 or to the nucleotide sequence of the deposited endogenous plasmid can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present invention provides *Ketogulonigenium*, comprising a transgene (recombinant DNA) comprising an endogenous *Ketogulonigenium* plasmid. Preferably, the endogenous *Ketogulonigenium* plasmid is contained in Deposit No. NRRL B-21627. As used herein, a transgene is defined as a transplanted nucleotide sequence which is exogenous, or non-native, to the host. An exogenous nucleotide sequence, as used in the current context, is a nucleotide sequence which is not found in Deposit No. NRRL B-21627. Thus, the term exogenous nucleotide sequence is meant to encompass a nucleotide sequence that is foreign to Deposit No. NRRL B-21627, as well as a nucleotide sequence endogenous, or native, to Deposit No. NRRL B-21627 that has been modified. Modification of the endogenous nucleotide sequence may include, for instance, mutation of the native nucleotide sequence or any of its regulatory elements. As used herein, mutation is defined as any change in the wild-type sequence of genomic or plasmid DNA. An additional form of modification may also include fusion of the endogenous nucleotide sequence to a nucleotide sequence that is normally not present, in relation to the endogenous nucleotide sequence. The transgene may be regulated by its normal promoter, or more commonly, by a promoter that normally regulates a different gene. The invention also provides a method for producing transformed *Ketogulonigenium*, comprising transforming *Ketogulonigenium* with a transgene, comprising, part or all of an endogenous *Ketogulonigenium* plasmid. Preferably, the endogenous *Ketogulonigenium* plasmid is contained in Deposit No. NRRL B-21627.

The term replicon as used herein is meant to encompass a DNA sequence comprising those genes and gene expression control elements such as promoters and terminators, other DNA sequence features such as short sequence repeats (iterons), origins of plasmid replication (ori or oriV sites), or other DNA sequence features that are required to support the autonomous replication of a circular DNA molecule in a bacterial host (Chapter 122, pp. 2295–2324, in *Escherichia coli and Salmonella: Cellular and Molecular Biology*, $2^{nd}$ Edition, Frederick C. Neidhardt, Ed., ASM Press (1996)). The requirements of a replicon can vary from as little as a short ori sequence in the case of plasmids that do not require their own replication proteins, to larger sequences containing one or more plasmid-borne replication genes.

The definition of a transformed cell, as used herein, is a cell where DNA has been inserted into a bacterial cell. The transformation of Ketogulonigenium may be transient or stable. Preferably, the invention provides a method for producing stably transformed *Ketogulonigenium*. As used herein, a stably transformed cell is a cell wherein a transgene is transmitted to every successive generation. A preferred embodiment of the present invention is that *Ketogulonigenium* is transformed via electroporation. An additional preferred embodiment of the present invention is that *Ketogulonigenium* is transformed by the process of conjugation, including, for instance, bi-parental and tri-parental conjugation. Conjugation, as used herein, is the process by which bacteria transfer DNA from a donor cell to a recipient cell through cell-to cell contact.

The present invention relates to a novel genus of bacteria, comprising the ADMX6L strain, designated as *Ketogulonigenium*. The present inventors have discovered novel strains of bacteria, not belonging to any known genera, that produce 2-keto-L-gulonic acid from sorbitol.

*Ketogulonigenium* (Ke.to.gu.lo.ni.gen'.i.um. M.L. n. acidum *ketogulonicum* ketogulonic acid; Gr. V. gennaio to produce; M.L. n. *ketogulonigenium* ketogulonic acid producing) is gram negative, facultatively anaerobic, motile or non-motile, has ovoid to rod-shaped cells, 0.8–1.3 µm long, 0.5–0.7 µm in diameter, with tapered ends, occurring as single cells, pairs and occasionally short chains. Some strains form elongated cells (up to 30 µm in length) on TSB. Flagella and fimbrae have been observed. Colonies are tan colored, smooth, circular, entire, raised to convex, 1–2 mm in diameter with a diffusable brown pigment after 48 hrs incubation. Oxidase and catalase reactions are positive. Optimum temperature range is 27 to 31°C., optimum pH range is 7.2 to 8.5 and optimum $Na^+$ concentration is 117–459 mM. Chemoorganotrophic. Carbon sources utilized include arabinose, cellobiose, fructose, glucose, glycerol, inositol, lactose, maltose, mannitol, mannose, rhamnose, sorbitol, sorbose, sucrose, trehalose, pyruvate and succinate. Favored carbon sources are inositol, mannitol, glycerol, sorbitol, lactose and arabinose. All strains examined produce 2-keto-L-gulonic acid from L-sorbose. Major cellular fatty acids are 16:0 and 18:1 ω7c/ω9t/ω12t and the mol % DNA G+C is 52.1 to 54.0 percent. Small subunit rDNA sequence analysis place this genus in the alpha subgroup of the Proteobacteria. All strains isolated in the present study group originated in soil. DNA reassociation studies divide the genus into two species. *K. vulgarae* and *K. robustum*, of which *K. vulgarae* is the designated type species. A group of bacteria having the above-mentioned properties does not belong to any known genera as described in Bergey's Manual of Systematic Bacteriology, and therefore belongs to a new genus.

Strain ADMX6L of *Ketogulonigenium* was isolated and deposited at the Agricultural Research Service Culture Collection (NRRL), 1815 North University Street, Peoria, Ill. 61604, USA, on Oct. 1, 1996, under the provisions of the Budapest Treaty, and assigned accession numbers NRRL B-21627.

The present invention provides a method for conjugative transfer of a vector from *E. coli* to *Ketogulonigenium* comprising culturing the *E. coli* with the *Ketogulonigenium* under such conditions such that the *E. coli* transfers the vector to the *Ketogulonigenium*. The method of conjugative transfer relies on the ability of the vector to replicate in both organisms, and thus requires that the vector contain replicons that are functional in both organisms. A replicon is a nucleotide sequence, typically several hundred to several thousand base pairs long, that is vital to plasmid DNA replication. Preferably, the method comprises using any vector that contains a replicon that is functional in *E. coli*, as well a replicon that is functional in *Ketogulonigenium*. More preferably, the method of the invention comprises the vectors pDELIA8 and pXH2/K5. Given that the preferred method comprises using any vector that contains a replicon that is functional in *E. coli*, as well as a replicon that is functional in *Ketogulonigenium*, it would also be possible to transfer a vector, via conjugation, from *Ketogulonigenium* to *E. coli*.

The present invention also provides a method for transforming *Ketogulonigenium* comprising inserting a vector into the Ketogulonigenium through the process of electroporation. Preferably, the vector used in electroporation of *Ketogulonigenium* is pMF1014-α.

The present invention provides isolated or purified nucleic acid molecules comprising the polynucleotides, or their complements, of endogenous plasmids that have been isolated and purified from a strain, NRRL Deposit No. B-21627 (ADMX6L), of this novel genus. Four endogenous plasmids have been isolated from strain NRRL Deposit No. B-21627. The nucleotide sequence shown in FIG. 1 (SEQ ID NO:1) is the nucleotide sequence of plasmid pADMX6L1 as determined by automated sequencing. The nucleotide sequence shown in FIG. 2 (SEQ ID NO:2) is the nucleotide sequence of plasmid pADMX6L2 as determined by automated sequencing. The nucleotide sequence shown in FIG. 3 (SEQ ID NO:3) is the nucleotide sequence of plasmid pADMX6L3 as determined by automated sequencing. The nucleotide sequence shown in FIG. 4 (SEQ ID NO:4) is the nucleotide sequence of plasmid pADMX6L4 as determined by automated sequencing.

The endogenous plasmids contained within NRRL B-21627 (ADMX6L) have been isolated and ligated into pUC19 or pJND1000. Specifically, plasmid pADMX6L1, corresponding to SEQ ID NO:1, and pJND 1000 are digested with BamHI and ligated to each other using T4 ligase. The pXB1 plasmid construct was then introduced into *E. coli* DH5αMCR and the culture collection was deposited at the Agricultural Research Service Culture Collection (NRRL), 1815 North University Street, Peoria, Ill. 61604, USA, on Feb. 23, 2001, under the provisions of the Budapest Treaty, and assigned accession numbers NRRL B-30418. Plasmid pADMX6L2, corresponding to SEQ ID NO:2, and pUC19 were digested with HinDIII and ligated to one another using T4 ligase. The pXH2 plasmid construct was then introduced into *E. coli* DH5αMCR and the culture collection was deposited at the Agricultural Research Service Culture Collection (NRRL), 1815 North University Street, Peoria, Ill. 61604, USA, on Feb. 23, 2001, under the provisions of the Budapest Treaty, and assigned accession numbers NRRL B-30419. Plasmid pADMX6L4, corresponding to SEQ ID NO:4, and pUC19 are digested with SspI and SmaI, respectively, and ligated to one another using T4 ligase. The pXB4 plasmid construct was then introduced into *E. coli* DH5αMCR and the culture collection is deposited at the Agricultural Research Service Culture Collection (NRRL), 1815 North University Street, Peoria, Ill. 61604, USA, on Mar. 12, 2001, under the provisions of the Budapest Treaty, and assigned accession number NRRL B-30435.

Unless otherwise indicated, all nucleotide sequences determined by sequencing a DNA molecule herein were determined using an automated DNA sequencer (such as the ABI Prism 3700). Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U) where each thymidine deoxynucleotide (T) in the specified deoxynucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxynucleotide A, G or C of SEQ ID NO:1 has been replaced by the corresponding ribonucleotide A, G or C, and each deoxynucleotide T has been replaced by a ribonucleotide U.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

One aspect of the invention provides an isolated or purified nucleic acid molecule comprising a polynucleotide having a nucleotide sequence selected from the group consisting of: (a) a nucleotide sequence in SEQ ID NO:1, SEQ ID NO:2, SEQ ID NO:3, SEQ ID NO:4, SEQ ID NO:5, SEQ ID NO:6, and SEQ ID NO:7; (b) a nucleotide sequence of a plasmid contained in NRRL Deposit No. B-30418, NRRL Deposit No. B-30419, and NRRL Deposit No. B-30435; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 97%, 98% or 99% identical, to any of the *Ketogulonigenium* nucleotide sequences in (a), (b) or (c) above, or a polynucleotide which hybridizes under stringent hybridization conditions to a polynucleotide having a nucleotide sequence identical to the *Ketogulonigenium* portion of a nucleotide sequence in (a), (b) or (c), above. The polynucleotide which hybridizes does not hybridize under stringent hybridization conditions to a polynucleotide having a nucleotide sequence consisting of only A residues or of only T residues.

A polynucleotide having a nucleotide sequence at least, for example, 95% "identical" to a reference nucleotide sequence is intended to mean that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule is at least 90%, 95%, 97%, 98% or 99% identical to, for instance, the nucleotide sequences shown in FIGS. 1, 2, 3, 4, 5, 6, or 7, or to the nucleotide sequences of the deposited plasmids can be determined conventionally using known computer programs such as the FastA program. FastA does a Pearson and Lipman search for similarity between a query sequence and a group of sequences of the same type nucleic acid. Professor William Pearson of the University of Virginia Department of Biochemistry wrote the FASTA program family (FastA, TFastA, FastX, TFastX and SSearch). In collaboration with Dr. Pearson, the programs were modified and documented for distribution with GCG Version 6.1 by Mary Schultz and Irv Edelman, and for Versions 8 through 10 by Sue Olson.

The present application is directed to nucleic acid molecules at least 95%, 97%, 98% or 99% identical to the nucleic acid sequences shown in FIG. 1 (SEQ ID NO:1), FIG. 2 (SEQ ID NO:2), FIG. 3 (SEQ ID NO:3), and FIG. 4 (SEQ ID NO:4); or to the *Ketogulonigenium* portion of the nucleic acid sequence of the deposited plasmids.

The present application is also directed to nucleic acid molecules at least 95%, 97%, 98% or 99% identical to the nucleic acid sequences shown in FIG. 5 (SEQ ID NO:5), FIG. 6 (SEQ ID NO:6), and FIG. 7 (SEQ ID NO:7).

One aspect of the invention provides an isolated nucleic acid molecule comprising a polynucleotide which hybridizes under stringent hybridization conditions to a portion of the polynucleotide of a nucleic acid molecule of the invention described above, for instance, in the plasmid contained in NRRL B- 30418, NRRL B-30419, or NRRL B-30435, or in SEQ ID NO:1, SEQ ID NO:2, SEQ ID NO:3, SEQ ID NO:4, SEQ ID NO:5, SEQ ID NO:6, or SEQ ID NO:7. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers.

Of course, polynucleotides hybridizing to a larger portion of the reference polynucleotides (e.g., the deposited endogenous plasmids), for instance, a portion 15–750 nt in length, or even to the entire length of the reference polynucleotide, are also useful as probes according to the present invention, as are polynucleotides corresponding to most, if not all, of the Ketogulonigenium portion of the nucleotide sequence of the deposited DNA or the nucleotide sequence as shown in FIGS. 1 (SEQ ID NO:1), 2 (SEQ ID NO:2), 3 (SEQ ID NO:3), 4 (SEQ ID NO:4), 5 (SEQ ID NO:5), 6 (SEQ ID NO:6), and 7 (SEQ ID NO:7). A portion of a polynucleotide of, at least 15 nt in length, for example, is intended to mean 15 or more contiguous nucleotides from the nucleotide sequence of the reference polynucleotide, (e.g., the deposited DNA or the nucleotide sequences as shown in FIGS. 1 (SEQ ID NO:1), 2 (SEQ ID NO:2), 3 (SEQ ID NO:3), 4 (SEQ ID NO:4), 5 (SEQ ID NO:5), 6 (SEQ ID NO:6), 7 (SEQ ID NO:7)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, edited by Sambrook, J., Fritsch, E. F. and Maniatis, T., (1989), Cold Spring Harbor Laboratory Press, the entire disclosure of which is hereby incorporated herein by reference.

One embodiment of the present invention is a vector comprising the nucleic acid molecules contained in the group consisting of SEQ ID NO:1, SEQ ID NO:2, SEQ ID NO:3 and SEQ ID NO:4, corresponding to endogenous plasmids contained in Deposit No. NRRL B-21627 (ADMX6L). A preferred embodiment of the present invention is that polynucleotides of interest can be joined to the nucleic acid molecules of the present invention, which may contain a selectable marker. An additional preferred embodiment is that the vectors comprising the nucleic acid molecules also contain a transcription terminator, a promoter and a polylinker site. As used herein, a polylinker site is defined to be a discrete series of restriction endonuclease sites that occur between the promoter and the terminator. The vector can optionally contain its native expression vector and/or expression vectors which include chromosomal-, and episomal-derived vectors, e.g., vectors derived from bacterial exogenous plasmids, bacteriophage, and vectors derived from combinations thereof, such as cosmids and phagemids.

A DNA insert of interest should be operatively linked to an appropriate promoter, such as its native promoter or a host-derived promoter, the phage lambda $P_L$ promoter, the phage lambda $P_R$ promoter, the *E. coli* lac promoters, such as the lacI and lacZ promoters, trp and tac promoters, the T3 and T7 promoters and the gpt promoter to name a few. Other suitable promoters will be known to the skilled artisan.

The expression constructs will preferably contain sites for transcription initiation, termination and, in the transcribed region, a ribosome binding site for translation. The coding portion of the mature transcripts expressed by the constructs can include a translation initiating codon at the beginning and a termination codon appropriately positioned at the end of the coding sequence to be translated.

As indicated, the expression vectors will preferably include at least one marker capable of being selected or screened for. Preferably the selectable marker comprises a nucleotide sequence which confers antibiotic resistance in a host cell population. Such markers include amikacin, ampicillin, chloramphenicol, erythromycin, gentamicin, kanamycin, penicillin, spectinomycin, streptomycin, or tetracycline resistance genes. Other suitable markers will be readily apparent to the skilled artisan.

The translated polypeptide encoded by the DNA in the vector may be expressed in a modified form, such as a fusion protein, and may include not only secretion signals, but also additional heterologous functional regions. Thus, for instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification.

The translated protein encoded by the DNA contained in the vector can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The present invention also provides vectors comprising nucleic acid molecules comprising a nucleotide sequence of a replicon found on an endogenous plasmid contained in Deposit No. NRRL B-21627. Preferably, the vector of the present invention comprises a replicon selected from the group of nucleotide sequences comprising SEQ ID NO:5, SEQ ID NO:6 and SEQ ID NO:7. The replicon is a nucleotide sequence that is typically several hundred to several thousand base pairs long and encodes functions controlling the replication of plasmid DNA. The nucleotide sequence in FIG. 5 (SEQ ID NO:5) is the nucleotide sequence comprising a replicon on plasmid pADMX6L1. The nucleotide sequence in FIG. 6 (SEQ ID NO:6) is the nucleotide sequence comprising a replicon on plasmid pADMX6L2. The nucleotide sequence in FIG. 7 (SEQ ID NO:7) is the nucleotide sequence comprising a replicon on plasmid pADMX6L3.

The present invention further provides a vector which has an replicon that is functional in *Escherichia coli* (*E. coli*) as well as a replicon that is functional in *Ketogulonigenium*. The present invention also provides a vector which has a replicon that is functional in *Ketogulonigenium*, as well as a replicon that is functional in any of the genera comprising the group consisting of *Acetobacter, Corynebacterium, Rhodobacter, Paracoccus, Roseobacter, Pseudomonas, Pseudogluconobacter, Gluconobacter, Serratia, Mycobacterium, Streptomyces* and *Bacillus*. Utilizing the fact that the vector comprises *Ketogulonigenium*, and preferably also comprises a replicon functional in *E. coli*, the present invention provides for a transformed cell of the genus *Ketogulonigenium*, comprising the vector. The present invention also provides for a transformed *E. coli*, comprising the vector. *E. coli* is known to be an efficient host for amplification of a vector DNA and manipulation of recombinant DNA by simple and rapid methods. On the other hand, *Ketogulonigenium* can be used as a host for expression of *Ketogulonigenium* genes. Since the vectors of the present invention are such functional constructs, they enable cloning of certain genes of *Ketogulonigenium* in *E. coli* and thereafter the effective expression of the genes in *Ketogulonigenium*. Furthermore, it is favorable that such functional constructs also contain a DNA region necessary for conjugal transfer (mob site). Hence the vectors of the present invention can first be assembled in *E. coli* and then directly introduced into *Ketogulonigenium* by conjugal mating without isolation of plasmid DNA from *E. coli*.

The present invention further relates to (a) nucleic acid sequences comprising at least 95% functional homology with those encoding polypeptides derived from the four endogenous plasmids from *Ketogulonigenium* strain ADMX6L, and (b) to amino acid sequences comprising at least 95% functional homology with those encoded within the plasmids. The invention also relates to nucleic acid sequences comprising at least 95% functional homology with, pADMX6L1 rep ORF (bases 2255–2710 of FIG. 1 (SEQ ID NO:1), pADMX6L2 rep ORF (reverse compliment of bases 3960–2562 of FIG. 2 (SEQ ID NO:2), and pADMX6L3 rep ORF (reverse compliment of bases 5031–4003 of FIG. 3 (SEQ ID NO:3)). The invention further relates to amino acid sequences comprising at least 95% functional homology with those set forth in FIGS. 8, 9 or 10.

Methods used and described herein are well known in the art and are more particularly described, for example, in R. F. Schleif and P. C. Wensink, *Practical Methods in Molecular Biology*, Springer-Verlag (1981); J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); P. F. Smith-Keary, *Molecular Genetics of Escherichia coli*, The Guilford Press, New York, N.Y. (1989); *Plasmids: A Practical Approach*, 2nd Edition, Hardy, K. D., ed., Oxford University Press, New York, N.Y. (1993); *Vectors: Essential Data*, Gacesa, P., and Ramji, D. P., eds., John Wiley & Sons Pub., New York, N.Y. (1994); *Guide to Electroporation and electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of Plasmids*, Summers, D. K., Blackwell Science, Cambridge, Mass. (1996); *Understanding DNA and Gene Cloning: A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al., eds., Butterworth, Boston, Mass. (1988); *Bacterial Conjugation*, Clewell, D. B., ed., Plenum Press, New York, N.Y. (1993); Del Solar, G., et al., "Replication and control of circular bacterial plasmids," *Microbiol. Mol. Biol. Rev.* 62:434–464 (1998); Meijer, W. J., et al., "Rolling-circle plasmids from *Bacillus subtilis*: complete nucleotide sequences and analyses of genes of pTA1015, pTA1040, pTA1050 and pTA1060, and comparisons with related plasmids from gram-positive bacteria," *FEMS Microbiol. Rev.* 21:337–368 (1998); Khan, S. A., "Rolling-circle replication of bacterial plasmids," *Microbiol. Mol. Biol. Rev.* 61:442–455 (1997); Baker, R. L., "Protein expression using ubiquitin fusion and cleavage," *Curr. Opin. Biotechnol.* 7:541–546 (1996); Makrides, S. C., "Strategies for achieving high-level expression of genes in *Escherichia coli*," *Microbiol. Rev.* 60:512–538 (1996); Alonso, J. C., et al., "Site-specific recombination in gram-positive theta-replicating plasmids," *FEMS Microbiol. Lett.* 142:1–10 (1996); Miroux, B., et al., "Over-production of protein in *Escherichia coli*: mutant hosts that allow synthesis of some membrane protein and globular protein at high levels," *J. Mol. Biol.* 260:289–298 (1996); Kurland, C. G., and Dong, H., "Bacterial growth inhibited by overproduction of protein," *Mol. Microbiol.* 21:1–4 (1996); Saki, H., and Komano, T., "DNA replication of IncQ broad-host-range plasmids in gram-negative bacteria," *Biosci. Biotechnol. Biochem.* 60:377–382 (1996); Deb, J. K., and Nath, N., "Plasmids of corynebacteria," *FEMS Microbiol. Lett.* 175:11–20 (1999); Smith, G. P., "Filamentous phages as cloning vectors," *Biotechnol.* 10:61–83 (1988); Espinosa, M., et al., "Plasmid rolling cicle replication and its control," *FEMS Microbiol. Lett.* 130:111–120 (1995); Lanka, E., and Wilkins, B. M., "DNA processing reaction in bacterial conjugation," *Ann. Rev. Biochem.* 64:141–169 (!995); Dreiseikelmann, B., "Translocation of DNA across bacterial membranes," *Microbiol. Rev.* 58:293–316 (1994); Nordstrom, K., and Wagner, E. G., "Kinetic aspects of control of plasmid replication by antisense RNA," *Trends Biochem. Sci.* 19:294–300 (1994); Frost, L. S., et al., "Analysis of the sequence gene products of the transfer region of the F sex factor," *Microbiol. Rev.* 58:162–210 (1994); Drury, L., "Transformation of bacteria by electroporation," *Methods Mol. Biol.* 58:249–256 (1996); Dower, W. J., "Electroporation of bacteria: a general approach to genetic transformation," *Genet. Eng.* 12:275–295 (1990); Na, S., et al., "The factors affecting transformation efficiency of coryneform bacteria by electroporation," *Chin. J. Biotechnol.*

11:193–198 (1995); Pansegrau, W., "Covalent association of the traI gene product of plasmid RP4 with the 5'-terminal nucleotide at the relaxation nick site," *J. Biol. Chem.* 265: 10637–10644 (1990); and Bailey, J. E., "Host-vector interactions in *Escherichia coli*," *Adv. Biochem. Eng. Biotechnol.* 48:29–52 (1993).

EXAMPLES

The following examples are illustrative only and are not intended to limit the scope of the invention as defined by the appended claims.

Example 1

Preparation of plasmid DNA from *Ketogulonigenium* and *E. coli* Strains.

A portion of a frozen culture of *Ketogulonigenium robustum* ADMX6L (NRRL B-12627) was seeded into 10 ml X6L medium (2% mannitol, 1% yeast extract, 1% soytone, 0.5% malt extract, 0.5% NaCl, 0.25% $K_2HPO_4$, pH 7.8) and grown overnight at 30° C. A portion of a frozen culture of *Escherichia coli* transformed with pJND1000 was seeded into 10 ml of Luria Broth (1% tryptone, 0.5% yeast extract, 0.5% NaCl) and grown overnight at 37° C. Both cultures were used to prepare plasmid DNA.

DNA was isolated using the Promega Wizard Plus Midipreps DNA Purification System (Madison, Wis.). The culture was centrifuged at 10,000× g for 10 minutes at 4° C. in a Sorval RC-5B centrifuge using the SS-34 rotor. The pellet was suspend in 3 ml of 50 mM Tris-HCl, pH 7.5, 10 mM EDTA, 100 μg/ml RnaseA. Three ml of cell lysis solution (0.2M NaOH, 1% SDS) was added and mixed by inverting the tube, then three ml of neutralization solution (1.32M potassium acetate, pH 4.8) was added and mixed by inverting the tube. The lysate was centrifuged at 14,000× g for 15 minutes at 4° C. in a SS-34 rotor, then the supernatant was carefully decanted to a new centrifuge tube. Ten ml of resuspension resin (40% isopropanol, 4.2M guanidine hydrochloride) was added to the supernatant fluid and mixed by swirling, then the mixture was transferred into the Promega Wizard Midicolumn, which was connected a vacuum manifold. Vacuum was applied to pull the resin/DNA mixture completely into the midicolumn. The column was washed twice with 15 ml of column wash solution (95% ethanol, 80 mM potassium acetate, 8.3 mM Tris-HCl, pH 7.5, 40 μM EDTA. The reservoir was removed from the midicolumn with a scissors, then the column was placed in a microcentrifuge tube and centrifuged at 10,000× g for 2 minutes to remove any residual solution. The midicolumn was transferred to a new microcentrifuge tube and 300 μl of sterile $dH_2O$ was applied. The tube was microcentrifuged at 10,000× g for 20 seconds to elute to the DNA into solution. A similar procedure would be employed for other plasmids from *Ketogulonigenium* or *E. coli*, except that choice and concentration of selective antibiotics would be altered as suitable for the plasmid being isolated.

Example 2

Transformation of a *Ketogulonigenium* Host with a Plasmid Using Electroporation

*Ketoguonigenium robustum* strain ADMX6L (NRRL B-21627) was transformed with plasmid pMF1014-α using the electroporation method. Plasmid pMF1014-α was described in a Ph.D. thesis at MIT (M. T. Follettie, "DNA Technology for *Corynebacterium glutamicum*: Isolation and Characterization of Amino Acid Biosynthetic Genes," Ph.D. Dissertation, Massachusetts Institute of Technology, Cambridge, Mass. (1989)). pMF1014α encodes kanamycin resistance and can replicate and be maintained in both *E. coli* and in *Ketogulonigenium*.

Competent *Ketogulonigenium* cells were prepared by seeding a single colony of ADMX6L into 10 ml of X6L medium (1% soytone, 1% yeast extract, 0.5% malt extract, 0.5% NaCl, 0.25% $K_2HPO_4$, 2% mannitol, pH 7.8). The culture was shaken at 300 rpm at 30 C until reaching an optical density of 0.8 units at 600 nm wavelength. Five ml of this culture was used to seed 500 ml of fresh X6L medium in a 2 L baffled erlenmeyer flask, which was shaken at 300 rpm at 30° C. until reaching an optical density of 0.8 units. The culture was chilled in an ice-water bath 10 minutes, then transferred to a pre-chilled centrifuge bottle and centrifuged at 5,000 rpm in a Sorvall 5C-RB Refrigerated Centrifuge for 15 minutes at 4° C. Cells were maintained at 2–4° C. for all steps to follow. The supernatent was decanted and the cell pellet suspended in 5 ml ice-cold Milli-Q water, then additional cold Milli-Q water was was added to a volume of 500 ml. The cells were centrifuged as before, then rewashed in 500 ml of Milli-Q water as before and recentrifuged. The twice-washed cell pellet was suspended in 40 ml of ice-cold 10% glycerol then centrifuged again as before. The supernatent was decanted, then the cells were suspended in a volume of chilled 10% glycerol approximately equal to the volume of the cell pellet. The competent *Ketogulonigenium* cells were aliquoted to microcentrifuge tubes (40 μl per tube) and stored at −80° C.

A BioRad "Gene Pulser II" electroporator device was set to 1.5 kV, 25 uF. The pulse controller was set to 200 Ohms. One μl of pMF1014-α DNA prepared as in Example 1 was added to 40 μl of thawed chilled competent *Ketogulonigenium* cells on ice. The cell-DNA mixture was transferred to a pre-chilled electroporation cuvette, which was then transferred to the electroporation device and the pulse was applied. One ml of X6L medium was added to the cuvette, then the mixture was removed, transferred to a 10-ml test tube, and incubated for 2 hours with orbital shaking at 300 rpm and 30° C. The incubated cells (approximately 1.4 ml) were placed in a microcentrifuge tube and spun at 13,000 rpm for 2 minutes, after which 0.9 ml of clear supernatent was carefully removed. The cell pellet was suspended in the remaining supernatent, then the cells were spread onto the surface of an X6L medium agar plate (1.2% Difco Bacto Agar) containing 50 μg/ml of kanamycin, and the plate was incubated for 2–3 days at 30° C. Colonies that formed on this plate were *Ketogulonigenium* transformed with plasmid vector pMF1014-α.

Example 3

Transfer of Plasmids from *E. coli* to *Ketogulonigenium*, Deposit No. NRRL B-21627 by Bi-Parental or Tri-Parental Mating (A) Bi-Parental Mating Plasmid pDELIA8 was transferred into *Ketogulonigenium* from *E. coli* by conjugation. To make pDELIA8, the AflIII-SphI fragment from plasmid pFD288 (GenBank Accession No. U30830), which contains the cloned mob region of plasmid RK2 (GenBank Accession No. L27758), was isolated from agarose gels and ligated to the large AflIII-SphI fragment from plasmid pUC19 (GenBank Accession No. M77789) to make the intermediate plasmid pUC19/oriT. pUC19/oriT DNA was digested with SspI and DraI and the large (2527 bp) fragment was purified from an agarose gel. Plasmid pMF1014-α (M. T. Follettie, "DNA Technology for *Corynebacterium glutamicum*: Isolation and Characterization of Amino Acid Biosynthetic Genes", Ph.D. Dissertation, Massachusetts Institute of Technology, Cambridge, Mass. (1989)) was digested with BamHI and PstI, made blunt ended with Klenow fragment, and the large fragment was isolated from an agarose gel. The gel purified, blunt-ended fragments from pUC19/oriT and pMF1014-α were ligated together to make pDELIA8. pDELIA8 carries a gene for kanamycin resistance, a plasmid replication gene, the replicon that is functional in *E. coli* and in *Ketogulonigenium*, lacZα and a polylinker.

A 5 ml culture of *E. coli* S17-1 (ATCC 47055) was transformed with pDELIA8 using calcium chloride mediated transformation. The S17-7/pDELIA8 strain was grown in Luria Broth containing 50 μg/ml kanamycin at 37° C. overnight. *Ketogulonigenium robustum* strain ADMX6L01 was grown in X6L medium containing 50 μg/ml of nalidixic acid at 30° C. overnight. ADMX6L01 is a nalidixic acid resistant mutant of strain ADMX6L, derived by conventional mutagenesis of ADMX6L followed by selection of strains showing resistance to 50 μg/ml of nalidixic acid.

Fifty microliters of the fresh S17-1/pDELIA8 culture was transferred into 3 ml of Luria Broth containing 50 μg/ml of kanamycin and 5 μg/ml of tetracycline and grown at 37° C. until reaching an $OD_{600}$ of 0.2 to 0.4 absorption units at 600 nm. Two hundred microliters of the fresh ADMX6L01 culture was transferred into 3 ml of X6L medium containing nalidixic acid and grown at 30° C. until reaching an $OD_{600}$ of 0.8 absorption units. 400 μl of S17-1/pDELIA8 culture was placed in a 1.5 ml microcentrifuge tube and microcentrifuged for 2 minutes. The pellet was resuspended in X6L medium without antibiotics and spun down again. This pellet was resuspended in 1 ml of the fresh ADMX6L01 culture to achieve a suspension of mixed cells. The mixed cells were centrifuged to a pellet, resuspended in 1 ml of fresh X6L medium without antibiotics, then pelleted and washed once again in 1 ml of X6L medium. The final pellet of mixed cells was then resuspended in 100 μl of X6L medium without antibiotics and spotted onto a a sterilized GN-6 metrical 0.45 μm×25 mm filter (Gelman Sciences, Product No. 63068) resting on the surface of an X6L agar medium plate without antibiotics, which was then incubated overnight at 30° C. The cell biomass on the filter was resuspended in 3 ml of X6L medium and 50 μl of this suspension was plated onto X6L agar medium containing kanamycin and nalidixic acid at concentration 50 μg/ml each. Colonies that formed on this plate after 2–3 days incubation at 30° C. were *Ketogulonigenium* transconjugants transformed with pDELIA8.

(B) Tri-Parental Mating

A 5 ml culture of *E. coli* HB101 (ATCC33694) harboring plasmid pDELIA8 was grown in Luria Broth (LB) containing 50 μg/ml of kanamycin at 37 degrees overnight. A 5 ml culture of *E. coli* HB101 harboring plasmid RP1 (GenBank Accession No. L27758) was grown in Luria Broth containing 5 μg/ml of tetracycline at 37 degrees overnight. A 5 ml culture of *Ketogulonigenium robustum* ADMX6L01 was grown in X6L medium containing 50 μg/ml of nalidixic acid at 30 degrees overnight. Fifty microliters each of the fresh *E. coli* HB101/pDELIA8 and HB101/RP1 cultures were transferred to 3 ml of LB with 50 μg/ml of kanamycin or 5 μg/ml of tetracycline, respectively, and were grown to an $OD_{600nm}$ of 0.2 to 0.4. Two hundred microliters of the fresh *Ketogulonigenium robustum* ADMX6L01 culture was transferred to 3 ml of X6L medium containing 50 μg/ml of nalidixic acid and grown to an $OD_{600nm}$ of 0.8. Four hundred microliters each of the *E. coli* cultures was combined and pelleted in a 1.5 ml microfuge tube, then decanted, resuspended in 1 ml of X6L medium without antibiotics and spun down again. The supernatant was removed and the *E. coli* pellet was resuspended in 1 ml of the fresh ADMX6L01 culture. The three-strain mixture was centrifuged to a pellet, then resuspended again 1 ml of X6L medium without antibiotics and recentrifuged. The pellet from this wash was resuspended in 100 μl of X6L medium without antibiotics and spotted onto a sterilized GN-6 metrical 0.45 μm×25 mm filter (Gelman Sciences, Product No. 63068) resting on the surface of an X6L agar medium plate without antibiotics, which was then incubated overnight at 30° C. The cell biomass on the filter was resuspended in 3 ml of X6L medium and 50 μl of this suspension was plated onto X6L agar medium containing kanamycin and nalidixic acid at concentration 50 μg/ml each. Colonies that formed on this plate after 2–3 days incubation at 30° C. were *Ketogulonigenium* transconjugants transformed with plasmid pDELIA8.

Example 4

Construction of Plasmid Vector pJND1000 pJND1000 was constructed from segments of plasmids pUC19 (GenBank Accession No. M77789), pUC4K (GenBank Accession No. X06404), pFD288 (GenBank Accession No. U30830), and pFC5 (David M. Lonsdale et.al., "pFC1 to pFC7: A novel family of combinatorial cloning vectors.", *Plant Molecular Biology Reporter* 13(4):343–345 (1995)).

The ampicillin resistance gene ($amp^R$) was removed from pUC19 by digesting pUC19 DNA with restriction enzymes DraI and SspI, separating the 1748 bp vector fragment from the smaller $amp^R$ fragment and other fragments by gel electrophoresis, then recovering the 1748 bp fragment from a gel slice. A kanamycin resistance gene ($kan^R$) fragment from pUC4K was prepared by digesting pUC4K with restriction enzyme PstI, treating the mixture with Klenow Fragment to produce blunt ends, separating the fragments by gel electrophoresis, then purifying the 1240 bp $kan^R$ fragment from a gel slice. The isolated fragments from pUC19 and pUC4K were mixed and ligated with T4 ligase following the protocol of GibcoBRL technical bulletin 15244-2 (Rockville, Md.) to produce "intermediate p1", an intermediate plasmid carrying pUC19 features and a $kan^R$ gene. Strain *E. coli* DH5αMCR was transformed with the ligation mixture following an established protocol ("Fresh Competent *E. coli* prepared using $CaCl_2$", pp. 1.82–1.84, in J. Sambrook, E. F. Fritsch and T. Maniatis, *Molecular Cloning: A Laboratory Manual*, 2nd Ed. (1989)). Transformants were selected on Luria Broth plates containing 50 μg/ml of kanamycin.

An oriT site for conjugative transfer was obtained from plasmid pFD288 by restricting it with HaeII, converting the single stranded ends to blunt ends by treating the mixture with Klenow Fragment, separating the fragments by agarose gel electrophoresis, then purifying the 778 bp oriT fragment from a gel slice. The intermediate p1 plasmid was opened at a single site with restriction enzyme SapI, then treated with Klenow Fragment to convert the single stranded ends to blunt ends. The SapI digested, blunt ended p1 intermediate was mixed with the purified oriT fragment, then treated with T4 ligase as above to create "intermediate p2", a plasmid which carries oriT in addition to $kan^R$ and other pUC19-derived features. Strain *E. coli* DH5αMCR was transformed with the ligation mixture as above. Intermediate p2 was confirmed by restriction digestion analysis.

The polylinker in intermediate plasmid p2 was replaced with the polylinker from pFC5. To do this the two plasmids were separately restricted with PvuII, the fragments from each digestion reaction were separated by gel electrophoresis, then the pFC5-derived polylinker fragment (531 bp), and the larger non-polylinker fragment from intermediate p2 were purified from gel slices. The recovered p2 fragment and the pFC5-derived polylinker fragment were mixed and joined using T4 ligase as above to make plasmid pJND1000. The structure of pJND1000 was confirmed by restriction digestion analysis. PJND1000 replicates in E. coli, has a functioning kanamycin resistance gene, an RK2-derived oriT site to permit conjugative transfer into Ketogulonigenium and other hosts, a polylinker for DNA cloning, forward and reverse M13 primers to facilitate DNA sequencing reactions into the polylinker, and permits screening for cloned inserts by inactivation of lacZα using Xgal indicator plates.

Example 5

Isolation of Plasmid pXB1 Containing Linearized Ketogulonigenium Plasmid pADMX6L1

The DNA sequence of plasmid pADMX6L1 (SEQ ID NO:1) is about 7029 bp long and contains a single BamHI restriction site. The BamHI site was utilized to clone the pADMX6L1 sequence into the E. coli vector pJND1000. A DNA prep containing a mixture of the endogenous plasmids from Ketogulonigenium robustum ADMX6L, and purified pJND1000 DNA from E. coli, were made as in Example A and separately digested with restriction enzyme BamHI. A Wizard DNA Clean-Up kit was used to separate the digested DNA from enzyme and salts in preparation for the next step, with a final DNA suspension volume of 50 µl. DNA from the two digestions (3 µl of pJND1000 DNA and 10 µl of Ketogulonigenium plasmid DNA) was mixed and ligated overnight at room temperature using T4 ligase with the protocol of GibcoBRL technical bulletin 15244–2 (Rockville, Md.). Strain E. coli DH5αMCR was transformed with the ligation mixture following an established protocol ("Fresh Competent E. coli prepared using $CaCl_2$", pp. 1.82–1.84, in J. Sambrook, E. F. Fritsch and T. Maniatis, Molecular Cloning: A Laboratory Manual, 2nd Ed. (1989)). Transformants were spread on Luria Broth agar plates containing 50 µg/ml of kanamycin and 40 µg/ml of Xgal and grown at 37 deg C. Colonies that were white, indicating insertion of DNA into the pJND1000 BamHI site, were picked and cultured for further processing. Digestion of plasmid DNA from transformants using BamHI, EcoRV, and XhoI separately, yielded the expected fragment sizes for sucessful clioning of pADMX6L1 into the pJND1000 E. coli vector. The identity of the pADMX6L1 insert was further confirmed by partial DNA sequencing into the pADMX6L1 DNA region using the M13 sequencing primer regions, of the pJND1000 vector. The chimeric plasmid containing linearized pADMX6L1 cloned into pJND1000 was named pXB1. An E. coli host transformed with pXB1 was deposited in the patent collection of the National Regional Research Laboratories in Peoria, Ill., U.S.A. under the terms of the Budapest Treaty as NRRL B-30418.

Example 6

Isolation of Plasmid pXH2 Containing Linearized Ketogulonigenium Plasmid pADMX6L2

The DNA sequence of plasmid pADMX6L2 (SEQ ID NO:2) is about 4005 bp long and contains a single HinDIII restriction site. The HinDIII site was utilized to clone the pADMX6L2 sequence into the E. coli vector pUC19. The procedure was the same as in Example 5, except that prior to the ligation step the plasmid DNAs were digested with HinDIII instead of with BamHI, and transformants were plated on LB agar plates containing Xgal and 100 µg/ml of ampicillin instead of the kanamycin. Plasmid DNA from transformants giving white colonies was isolated and digested with HinDIII and NdeI, giving the expected fragment sizes for correct insertion of linearized pADMX6L2 DNA into the pUC19 vector. The identity of the pADMX6L2 insert was further confirmed by partial DNA sequencing into the pADMX6L2 region using the M13 primer regions of pUC19. The chimeric plasmid containing linearized pADMX6L2 cloned into pUC19 was named pXH2. An E. coli host transformed with pXH2 was deposited in the patent collection of the National Regional Research Laboratories in Peoria, Ill., U.S.A. under the terms of the Budapest Treaty as NRRL B-30419.

Example 7

Construction of E. coli/Ketogulonigenium Shuttle Plasmid pXH2/K5

Since kanamycin resistance can be expressed in Ketogulonigenium, it was desireable to replace the ampR resistance gene in pXH2 with a kanamycin resistance gene, thereby allowing the selective isolation of Ketogulonigenium strains transformed with a plasmid. In vitro transposition was used to move a kanamycin resistance gene into pXH2 and simultaneously inactivate ampicillin resistance. Insertion of a kanamycin resistance gene into the ampicillin resistance gene of pXH2 was achieved using Epicentre technologies EZ::TN Insertion System (Madison, Wis.). 0.05 pmoles of pXH2 was combined with 0.05 pmoles of the <KAN-1> Transposon, 1 µl of EZ::TN 10×Reaction Buffer, 1 µl of EZ::TN Transposase, and 4 ul of sterile water giving a total volume of 10 µl in the transposition reaction. This mixture was incubated at 37° C. for 2 hours, then stopped by adding 1 µl of EZ::TN 10×Stop Solution, mixing, and incubation at 70° C. in a heat block for 10 minutes. E. coli DH5αMCR was transformed with the DNA mixture and transformants were selected on Luria Broth agar plates containing 50 µg/ml of kanamycin. Colonies recovered from these plates were patched onto two LB agar plates, one with 50 µg/ml of kanamycin and the other with 100 µg/ml of ampicillin. Only those that grew on the kanamycin plates were saved. Plasmid DNA from an ampicillin sensitive, kanamycin resistant colony was isolated as "pXH2/K5". The proper insertion of the kanamycin resistance transposon into the vector ampicillin resistance gene was confirmed by analyzing pXH2/K2 DNA with various restriction endonucleases. To demonstrate the viability of pXH2/K5 as an E. coli/Ketogulonigenium yshuttle vector, Ketogulonigenium robustum strain ADMX6L was transfromed with pXH2/K5 DNA using the electroporation technique of Example 2. Stable, kanamycin resistant transformants were obtained from which pXH2/K5 DNA can be reisolated.

Example 8

Isolation of Plasmid pXB4 Containing Linearized Ketogulonigenium Plasmid pADMX6L4

The DNA sequence of plasmid pADMX6L4 (SEQ ID NO:4) is about 4211 bp long and contains a single SspI restriction site. The SspI site was utilized to clone the pADMX6L4 plasmid into the E. coli vector pUC19. The procedure was the same as in Example 6, except that prior to the ligation step the plasmid DNA from strain ADMX6L was digested with SspI and pUC19 was digested with SmaI.

Plasmid DNA from transformants giving white colonies was isolated and double digested with EcoRI and BamHI, and separately with PstI and SphI, in each case giving the expected fragment sizes for correct insertion of linearized pADMX6L4 DNA into pUC19. Partial DNA sequencing into the pADMX6L4 region using the M13 primers of pUC19 further confirmed the identity of the pADMX6L4 insert. The chimeric plasmid containing linearized pADMX6L4 cloned into pUC19 was named pXB4. An *E. coli* host transformed with pXB4 was deposited in the patent collection of the National Regional Research Laboratories in Peoria, Ill., U.S.A. under the terms of the Budapest Treaty as NRRL B-30435.

Example 9

Definition of DNA Sequences Comprising Replication Functions of *Ketogulonigenium* Plasmids Various programs of the Wisconsin Package version 10.1 (Genetics Computer Group, Inc. Madison, Wis.) were used to analyze the DNA sequences of the four endogenous plasmids from *Ketogulonigenium* strain ADMX6L. The analysis revealed multiple open reading frames (ORFs), nucleotide sequences having protein-encoding potential, on each plasmid. The predicted amino acid sequences of these ORFs was obtained, and a similarity search against PIR and SWISS-PROT protein databases was conducted using the GCG implementations of the FASTA (*Proc. Natl. Acad. Sci. USA* 85:2444–2448 (1988)) and BLAST (Altschul et al., *Nucleic Acids Research* 25:3389–3402 (1997)) methods. Based on sequence similarity to known plasmid-encoded replication proteins, plasmids pADMX6L1, pADMX6L2, and pADMX6L3 were found to encode potential plasmid replication proteins. The genes (ORFs) for these functions have the following endpoints:

| | |
|---|---|
| pADMX6L1 rep ORF: | bases 2255–2710 of FIG. 1 (SEQ ID NO:1) |
| pADMX6L2 rep ORF: | reverse compliment of bases 3960–2562 of FIG. 2 (SEQ ID NO:2) |
| pADMX6L3 rep ORF: | reverse compliment of bases 5031–4003 of FIG. 3 (SEQ ID NO:3). |

A region of DNA sequence upstream and downstream of the regions defined by these ORFs, perhaps 500 bp in each direction, is likely to contain transcriptional promoters, terminators, and other sequences required for proper expression of the replication proteins and control of plasmid replication. Therefore a region comprising part or all of the plasmid replicon for these three plasmids could be defined by the following DNA sequences:

| | |
|---|---|
| pADMX6L1 replicon: | bases 1755–3210 of the FIG. 1 sequence, also represented by SEQ ID NO:5 |
| pADMX6L2 replicon: | bases 455–2060 of the FIG. 2 sequence, also represented by SEQ ID NO:6 |
| pADMX6L3 replicon: | bases 3503–5531 of the FIG. 3 sequence, also represented by SEQ ID NO:7 |

All publications mentioned herein above are hereby incorporated in their entirety by reference. All publications cited in the annotations to the Genbank accession numbers or in ATCC strain descriptions cited herein are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated or purified nucleic acid molecule comprising a polynucleotide comprising a replicon functional in *Ketogulonigenium*, the polynucleotide having a nucleotide sequence at least 95% identical to a sequence selected from the group consisting of:
   (a) the nucleotide sequence of SEQ ID NO: 3; and
   (b) the nucleotide sequence that is the complement to SEQ ID NO: 3.

2. The isolated or purified nucleic acid molecule of claim 1, wherein said isolated or purified nucleic acid molecule has a nucleotide sequence that is at least 95% identical to that of part (a).

3. The isolated or purified nucleic acid molecule of claim 1, wherein said isolated or purified nucleic acid molecule has a nucleotide sequence that is that of part (a).

4. The isolated or purified nucleic acid molecule of claim 1, wherein said isolated or purified nucleic acid molecule has a nucleotide sequence that is at least 95% identical to that of part (b).

5. The isolated or purified nucleic acid molecule of claim 1, wherein said isolated or purified nucleic acid molecule has a nucleotide sequence that is that of part (b).

6. A vector comprising the nucleic acid molecule of claim 1 and at least one marker gene.

7. A vector comprising:
   (a) the nucleic acid molecule of claim 1;
   (b) a terminator of transcription;
   (c) a promoter; and
   (d) a discrete series of restriction endonuclease recognition sites, said series being between said promoter and said terminator.

8. An isolated nucleic acid molecule comprising a polynucleotide comprising a replicon functional in *Ketogulonigenium*, wherein the polynucleotide hybridizes under stringent hybridization conditions to a sequence selected from the group consisting of:
   (a) the nucleotide sequence of SEQ ID NO: 3; and
   (b) the nucleotide sequence that is the complement to SEQ ID NO: 3;
   wherein said polynucleotide which hybridizes, does not hybridize under stringent hybridization conditions to a polynucleotide having a nucleotide sequence consisting of only A residues or of only T residues.

9. An isolated or purified nucleic acid molecule comprising a polynucleotide comprising a replicon functional in *Ketogulonigenium*, the polynucleotide having a nucleotide sequence at least 95% identical to a *Ketogulonigenium* replicon sequence selected from the group consisting of:
(a) the nucleotide sequence of SEQ ID NO: 7; and
(b) the nucleotide sequence that is the complement to SEQ ID NO: 7.

10. The isolated or purified nucleic acid molecule of claim 9, wherein said isolated or purified nucleic acid molecule has a nucleotide sequence that is at least 95% identical to that of part (a).

11. The isolated or purified nucleic acid molecule of claim 9, wherein said isolated or purified nucleic acid molecule has a nucleotide sequence that is that of part (a).

12. The isolated or purified nucleic acid molecule of claim 9, wherein said isolated or purified nucleic acid molecule has a nucleotide sequence that is at least 95% identical to that of part (b).

13. The isolated or purified nucleic acid molecule of claim 9, wherein said isolated or purified nucleic acid molecule has a nucleotide sequence that is that of part (b).

14. An isolated or purified vector comprising the nucleic acid molecule of claim 9.

15. The vector of claim 14, comprising a replicon functional in an organism of the genus selected from the group consisting of *Acetobacter, Corynebacterium, Rhodobacter, Paracoccus, Roseobacter, Pseudomonas, Pseudoglucono bacter, Gluconobacter, Serratia, Mycobacterium, Streptomyces* and *Bacillus*.

16. The vector of claim 14, comprising a replicon functional in *Escherichia coli*.

17. A transformed cell of *Escherichia coil* comprising the vector of claim 16.

18. A transformed cell of the genus *Ketogulonigenium* comprising the vector of claim 16.

19. The vector of claim 16, wherein said *Ketogulonigenium* replicon is SEQ ID NO:7.

20. An isolated nucleic acid molecule comprising a polynucleotide comprising a replicon functional in *Ketogulonigenium*, wherein the polynucleotide hybridizes under stringent hybridization conditions to a sequence selected from the group consisting of:
(a) the nucleotide sequence of SEQ ID NO: 7; and
(b) the nucleotide sequence that is the complement to SEQ ID NO: 7; wherein said polynucleotide which hybridizes, does not hybridize under stringent hybridization conditions to a polynucleotide having a nucleotide sequence consisting of only A residues or of only T residues.

* * * * *

UNITED STATES PATENT AND TRADEMARK OFFICE
CERTIFICATE OF CORRECTION

PATENT NO. : 7,030,233 B2
APPLICATION NO. : 10/261481
DATED : April 18, 2006
INVENTOR(S) : John D'Elia and Steven F. Stoddard It is certified that error appears in the above-identified patent and that said Letters Patent is hereby corrected as shown below:

On The Title page, item 56 Other Publications – 2d reference, Delete "trasnport" and replace therewith --transport--

Title page, Page 2, item 56 Other Publications – Col. 2 – 1st reference, delete "2-Keo-L-glonic" and substitute therefor --2-Keto-L-gulonic--

Title page, Page 2, item 56 Other Publications – Col. 2 – 1st reference, after "*Microbiol*" insert a --.--

Title page, Page 2, item 56 Other Publications – Col. 2 – 6th reference, delete "Welshengwu" and substitute therefor --Weishengwu--

Column 1, line 52, delete "et at." And substitute therefor --et al.--

Column 2, line 67, Delete the second occurrence of "the"

Column 3, line 9, delete "pADMX6 µl" and substitute therefor --pADMX6L1--

Column 3, lines 37-44, delete "in" before -- is--.

Column 4, line 29, insert --are-- before "also".

Column 5, line 41, delete "ori or oriV" and substitute therefor --*ori* or *ori*V--

Column 5, line 48, delete "ori" and substituted therefor --*ori*--

Column 10, line 27, delete "*E. coli* lac" and substitute therefor --*E. coli lac*--

Column 10, line 28, delete "lacl and lacZ promoters, trp and tac promoters" and substitute therefor --*lac*l and *lac*Z promoters, *trp* and *tac* promoters--

Column 10, line 29, delete "gpt" and substitute therefor --*gpt*--

Column 11, lines 27-28, delete "Utilizing the fact that the vector comprises *Ketogulonigenium*" and substitute therefor --Utilizing the fact that the vector comprises a functional replicon in *Ketogulonigenium*--

Column 14, line 20, delete second occurrence of "was"

Column 14, line 64, delete "pUC19/oriT" and substitute therefor --pUC19/*ori*T--

UNITED STATES PATENT AND TRADEMARK OFFICE
CERTIFICATE OF CORRECTION

PATENT NO.        : 7,030,233 B2
APPLICATION NO. : 10/261481
DATED             : April 18, 2006
INVENTOR(S)       : John D'Elia and Steven F. Stoddard It is certified that error appears in the above-identified patent and that said Letters Patent is hereby corrected as shown below:

Column 16, line 31, delete "$amp^R$" and substitute therefor --$amp^R$--

Column 16, line 34, delete "$amp^R$" and substitute therefor --$amp^R$--

Column 16, line 36, delete "$kan^R$" and substitute therefor --$kan^R$--

Column 16, line 40, delete "$kan^R$" and substitute therefor --$kan^R$--

Column 16, line 45, delete "$kan^R$" and substitute therefor --$kan^R$--

Column 16, line 52, delete "oriT" and substitute therefor --$oriT$--

Column 16, line 56, delete "oriT" and substitute therefor --$oriT$--

Column 16, line 61, delete "oriT" and substitute therefor --$oriT$--

Column 16, line 63, delete "$kan^R$" and substitute therefor --$kan^R$--

Column 16, line 63, delete "oriT" and substitute therefor --$oriT$--

Column 17, line 11, delete "oriT" and substitute therefor --$oriT$--

Column 18, line 24, delete "$amp^R$" and substitute therefor --$amp^R$--

Column 64, line 5, delete "*Escherichia coiI*" and substitute therefor --*Escherichia coli*--

Signed and Sealed this

Eleventh Day of December, 2007

JON W. DUDAS
*Director of the United States Patent and Trademark Office*